(12) United States Patent
Haldar et al.

(10) Patent No.: US 9,783,490 B2
(45) Date of Patent: Oct. 10, 2017

(54) ANTIMICROBIAL COMPOUNDS, THEIR SYNTHESIS AND APPLICATIONS THEREOF

(71) Applicants: The Secretary of State for Health, London (GB); Jawaharlal Nehru Center for Advanced Scientific Research, Jakkur, Bangalore, Karnataka (IN)

(72) Inventors: Jayanta Haldar, Bangalore (IN); Chandradhish Ghosh, Bangalore (IN); Goutham Belagula Manjunath, Bangalore (IN); Padma Akkapeddi, Bangalore (IN)

(73) Assignees: The Secretary of State for Health, London (GB); Jawaharlal Nehru Centre for Advanced Scientific Research, Bangalore (IN)

( * ) Notice: Subject to any disclaimer, the term of this patent is extended or adjusted under 35 U.S.C. 154(b) by 0 days.

(21) Appl. No.: 14/652,714

(22) PCT Filed: Dec. 18, 2013

(86) PCT No.: PCT/IB2013/061090
§ 371 (c)(1),
(2) Date: Jun. 16, 2015

(87) PCT Pub. No.: WO2014/097178
PCT Pub. Date: Jun. 26, 2014

(65) Prior Publication Data
US 2015/0329478 A1    Nov. 19, 2015

(30) Foreign Application Priority Data
Dec. 18, 2012  (IN) ............................ 5299/CHE/2012

(51) Int. Cl.
| | | |
|---|---|---|
| C07D 215/00 | (2006.01) |
| C07C 237/06 | (2006.01) |
| C07C 231/12 | (2006.01) |
| A61K 38/05 | (2006.01) |
| C07D 215/12 | (2006.01) |

(52) U.S. Cl.
CPC ............ *C07C 237/06* (2013.01); *A61K 38/05* (2013.01); *C07C 231/12* (2013.01); *C07D 215/12* (2013.01)

(58) Field of Classification Search
None
See application file for complete search history.

(56) References Cited

U.S. PATENT DOCUMENTS

| | | | |
|---|---|---|---|
| 5,596,000 A | 1/1997 | Esser |
| 5,663,148 A | 9/1997 | Or |
| 5,883,121 A | 3/1999 | Yamashita |
| 2006/0009400 A1 | 1/2006 | Eckhardt |

FOREIGN PATENT DOCUMENTS

| | | |
|---|---|---|
| WO | 95/17888 A1 | 7/1995 |
| WO | 2007/129952 A1 | 11/2007 |

OTHER PUBLICATIONS

International Preliminary Report on Patentability mailed May 5, 2015, issued in corresponding International Application No. PCT/IB2013/061090, filed Dec. 18, 2013, 4 pages.
International Search Report mailed May 21, 2014, issued in corresponding International Application No. PCT/IB2013/061090, filed Dec. 18, 2013, 2 pages.
Extended European Search Report mailed Jul. 19, 2016, issued in Application No. EP 13865950.3, filed Dec. 18, 2013, 7 pages
Svenson, J., et al., "Albumin Binding of Short Cationic Antimicrobial Micropeptides and Its Influence on the In Vitro Bactericidal Effect," Journal of Medicinal Chemistry 50(14):3334-3339, Jul. 2007.

*Primary Examiner* — Heidi Reese
(74) *Attorney, Agent, or Firm* — Christensen O'Connor Johnson Kindness PLLC

(57) ABSTRACT

The present disclosure relates to the field of medicinal chemistry and more particularly to the development of antimicrobial compounds. The disclosure relates to the synthesis and characterization of compounds comprising aromatic radical or an aliphatic radical, an alkyl amine and amino acid moiety wherein said compounds exhibit antimicrobial activity against various drug-sensitive and drug-resistant pathogenic 10 microorganisms.

13 Claims, 8 Drawing Sheets

ANTIMICROBIAL COMPOUNDS, THEIR SYNTHESIS AND APPLICATIONS THEREOF

FIELD OF DISCLOSURE

The present disclosure relates to the field of medicinal chemistry and more particularly to the development of antimicrobial compounds. The disclosure relates to the synthesis and characterization of compounds comprising an aromatic radical and/or an aliphatic radical, an alkyl amine and amino acid moiety wherein said compounds exhibit antimicrobial activity against various drug-sensitive and drug-resistant pathogenic microorganisms.

BACKGROUND OF THE DISCLOSURE

Bacterial infections are a major global health hazard affecting millions of people worldwide. Many antibacterial drugs and articles have been developed over the years for better treatment or prevention of bacterial infections. Bacterial resistance to conventional antibiotics is one of the most serious problems facing world health today. Thus research towards development of newer antibiotics is imperative. In the recent past only Antimicrobial Peptides (AMPs) have shown some promise as potential antibiotics and several of them are undergoing clinical trials. AMPs are sentinels of innate immune system of most species and are usually the first line of defense against any infection. Naturally occurring AMPs are found to have a variety of medicinal properties e.g. antibacterial, antifungal, antiviral, anticancer, antiplasmodial activities. While most of the conventional antibiotics act by targeting intracellular organelles of bacteria, AMPs are known to act primarily by causing lysis of the bacterial cell membrane. Consequently, unlike in the case of conventional antibiotics, where even point mutations can render them inactive, bacteria are slow to develop resistance against antimicrobial peptides.

Despite the advantages, no AMP has been approved for clinical use, although some are undergoing clinical trials. The main reasons for these are their high in vivo toxicity, liability towards proteases and their high cost of manufacture. Although most of the natural AMPs are similar in their design, allowing facial amphiphilicity during antimicrobial action, their major limitations lie in the complexity of their synthesis. Consequently, substantial effort has been directed towards development of designs and strategies to counter the problems faced by AMPs.

In consideration to the aforementioned limitations, the applicants of the instant disclosure aim to arrive at antimicrobial compounds which are not only effective towards wild-type bacteria, but also, towards multi drug-resistant bacteria, less toxic and cost effective. The description herein will in detail illustrate the disclosure evidently describing the noted features of the invention.

SUMMARY OF THE DISCLOSURE

Accordingly, the present disclosure relates to a compound of formula I:

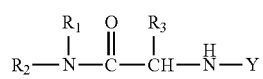

Formula-I wherein,
R$_1$ is an aromatic radical or aliphatic radical
R$_2$ is an aliphatic radical
R$_3$ is a side chain of an amino acid; and
Y is selected from a group consisting of hydrogen,

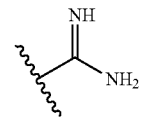 and 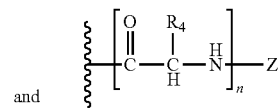

wherein 'n' ranges from 1 to 5,
Z is hydrogen or

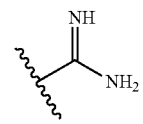

R$_4$ is a side chain of an amino acid.

A method of preparing a compound of formula I as mentioned above, said method comprising acts of: a) reacting aldehyde of aromatic radical or aliphatic radical with an alkyl amine to obtain a Schiff's base, b) reducing the Schiff's base to obtain a secondary amine, c) reacting the secondary amine with a free acid group of tert-butoxy carbamate protected amino acid or carboxylic acid group of the C-terminal of a peptide in which other reactive functional groups are protected, d) followed by deprotection of the protecting groups of the amino acid or the peptide to obtain the compound of formula I; a pharmaceutically accepted salt of the compound as mentioned above; and a composition comprising: the compound or the pharmaceutically acceptable salt as mentioned above and a pharmaceutically acceptable excipient.

BRIEF DESCRIPTION OF ACCOMPANYING FIGURES

The features of the present disclosure will become more fully apparent from the following description taken in conjunction with the accompanying drawings. It is to be understood that the drawings depict only several embodiments in accordance with the disclosure, and is therefore, not to be considered limiting in its scope. The disclosure will be described with additional specificity and detail through use of the accompanying drawing.

DETAILED DESCRIPTION OF THE DISCLOSURE

Figure 1:
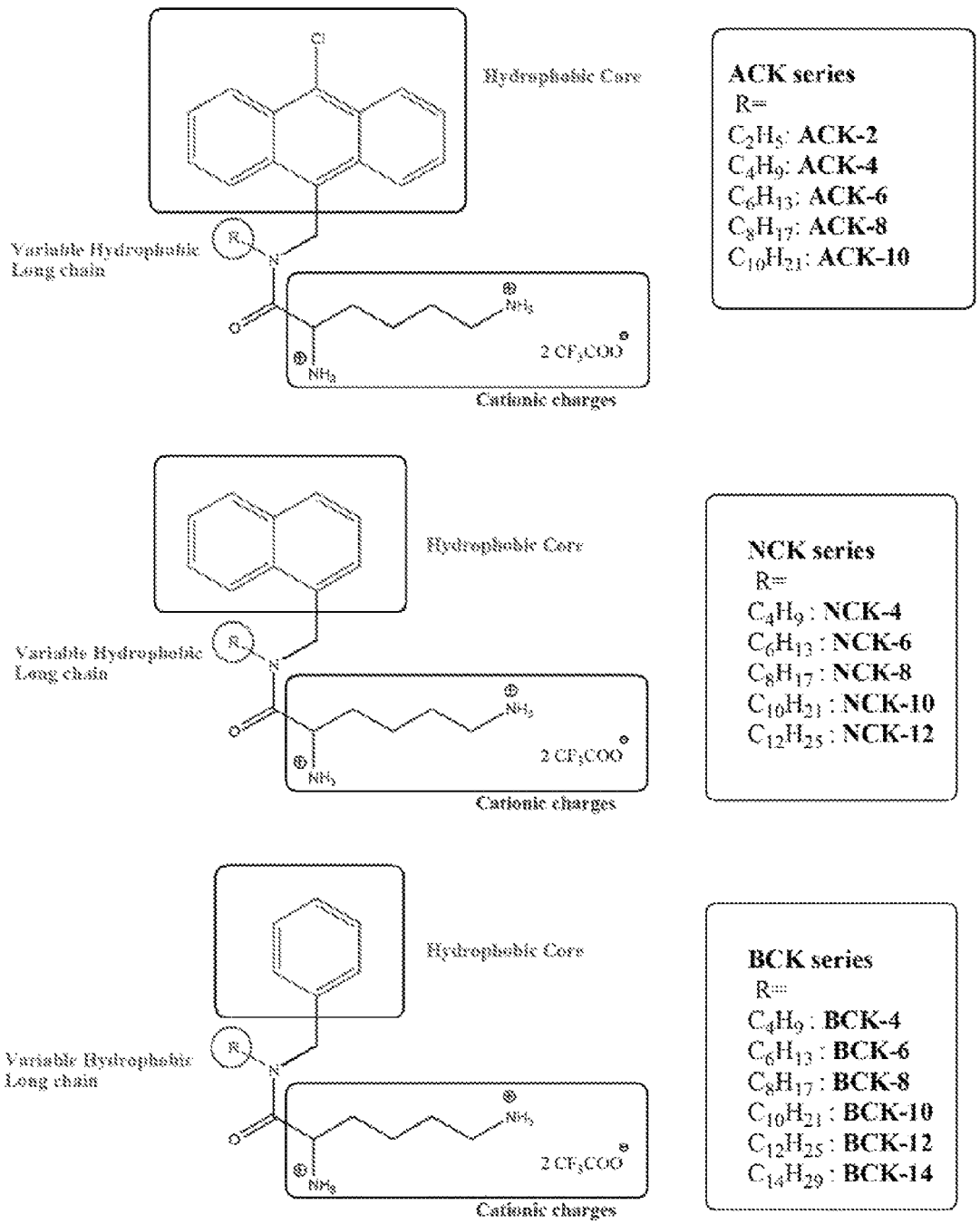
FIG. 1 represents Design and structure of compounds of Chloro-anthracene derivatives (ACK series), Naphthalene derivatives (NCK series) and benzene derivatives (BCK series).

The present disclosure relates to a compound of formula I:

Formula-I

wherein,
$R_1$ is an aromatic radical or aliphatic radical
$R_2$ is an aliphatic radical
$R_3$ is a side chain of an amino acid; and
Y is selected from a group consisting of hydrogen,

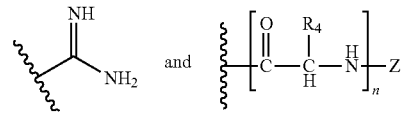

wherein 'n' ranges from 1 to 5.
Z is hydrogen or

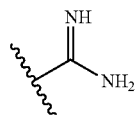

$R_4$ is a side chain of an amino acid.
In an embodiment of the disclosure the aromatic radical of $R_1$ is selected from a group consisting of but not limited to:

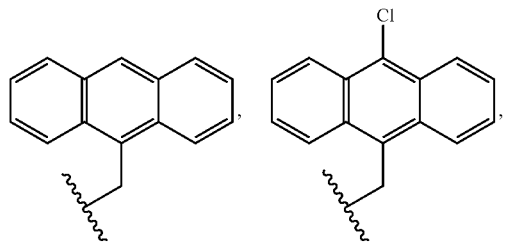

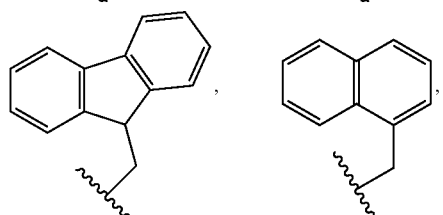

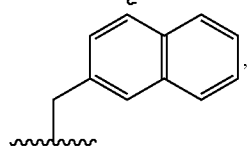

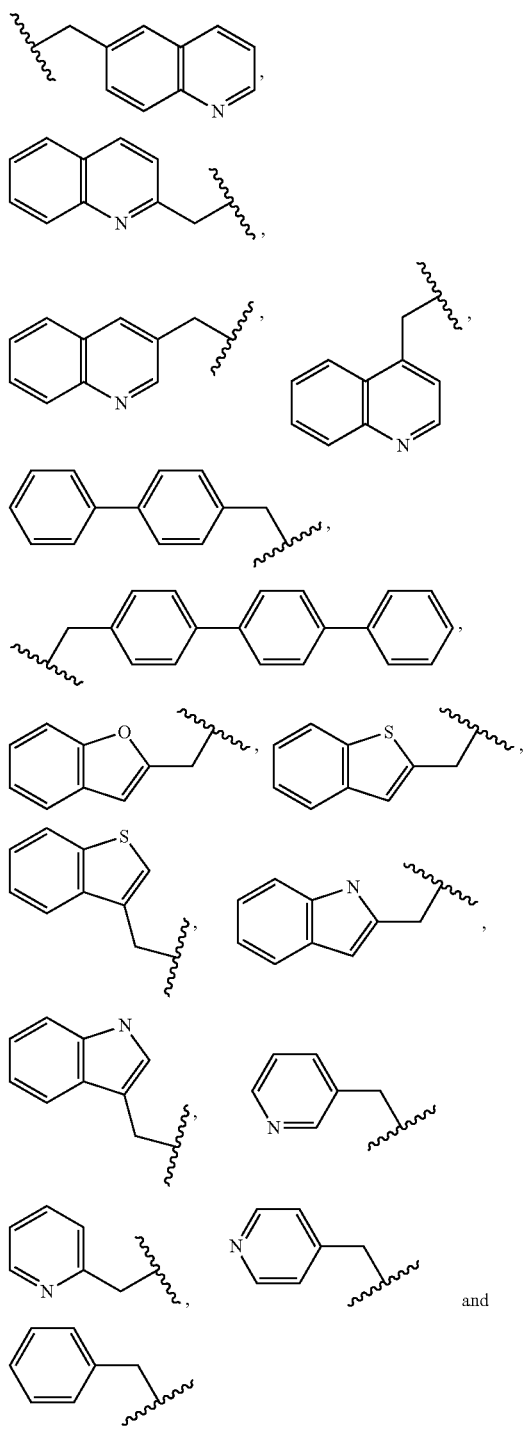

In another embodiment of the disclosure the aliphatic radical of $R_1$ is selected from a group consisting of but not limited to the following:

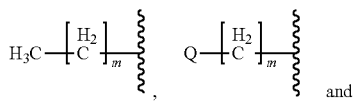

and

-continued

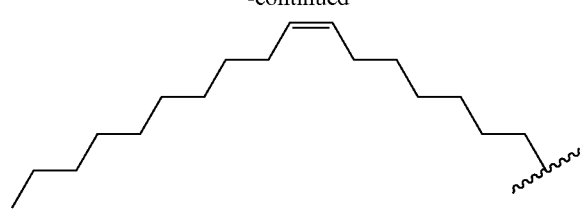

wherein,

Q can be halogen; cyano; nitro; amino; hydroxyl; or alkoxy;

m is an integer ranging from 1 to 20,

In yet another embodiment of the disclosure the aliphatic radical of $R_2$ is selected from a group consisting of but not limited the following:

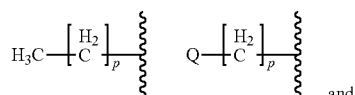 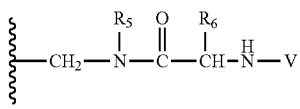 and

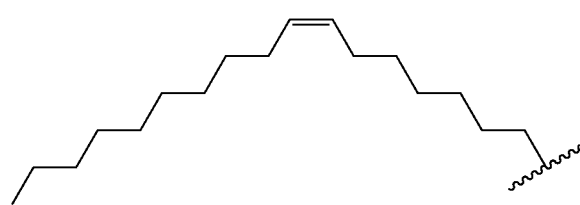

wherein,

Q is halogen; cyano; nitro; amino; hydroxyl; or alkoxy;

p is an integer ranging from 1 to 20,

In still another embodiment of the disclosure the aromatic radical of $R_1$ is selected from a group consisting of but not limited to the following:

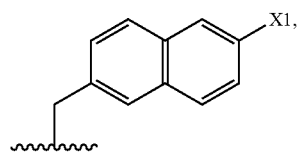

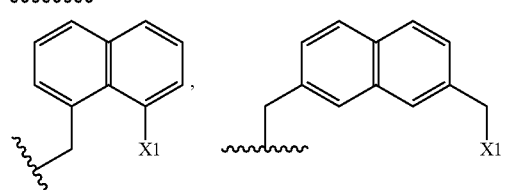

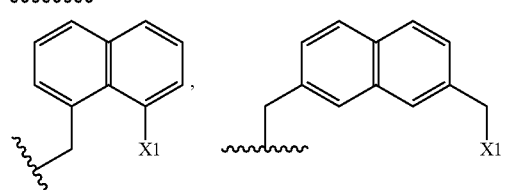

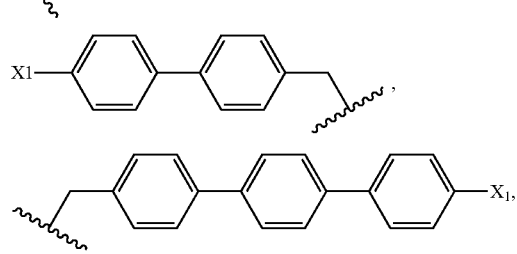

-continued

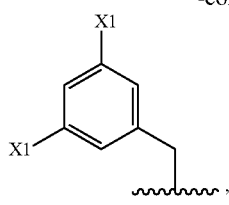

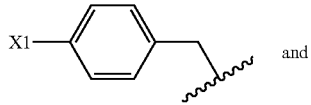 and 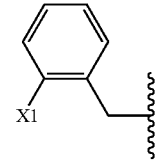

Wherein, $X_1$ is

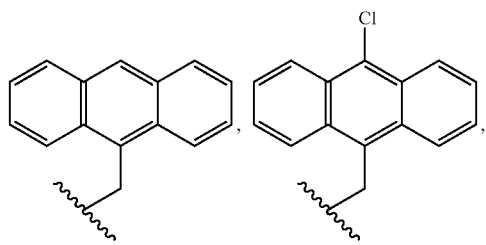

wherein, $R_5$ is selected from a group consisting of but not limited to the following:

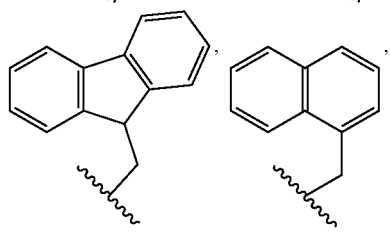

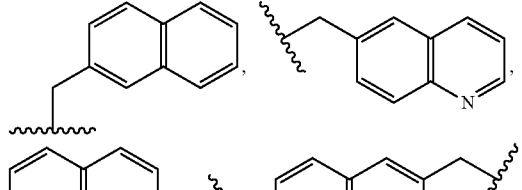

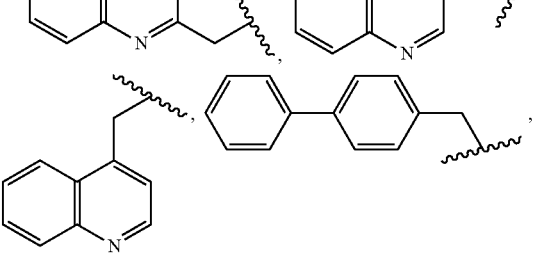

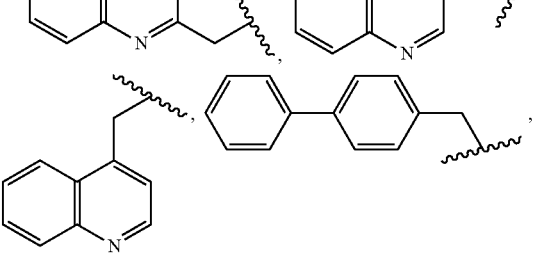

-continued

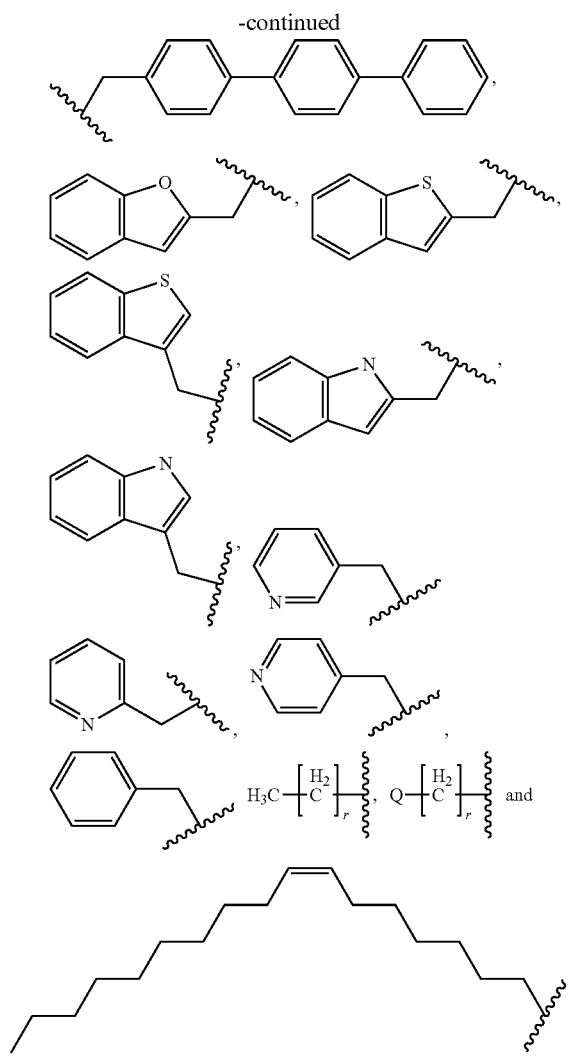

wherein,
'r' is an integer ranging from 1 to 20,
$R_6$ is a side chain of an amino acid; and
'V' is selected from a group consisting of hydrogen,

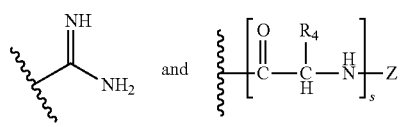

wherein, 's' ranges from 1 to 5
wherein, Z is hydrogen or

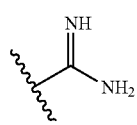

In still another embodiment of the disclosure the aliphatic radical of $R_1$ is:

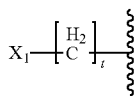

Wherein,
't' ranges from 1 to 20
$X_1$ is

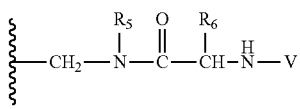

wherein,
$R_5$ is selected from a group consisting of but not limited to the following:

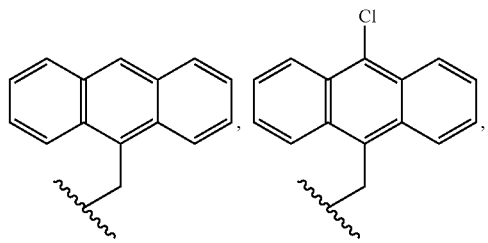

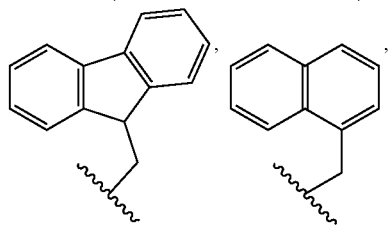

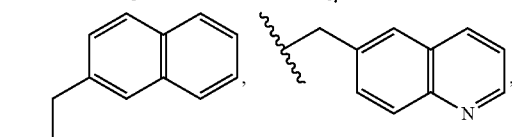

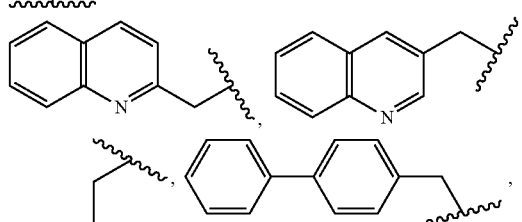

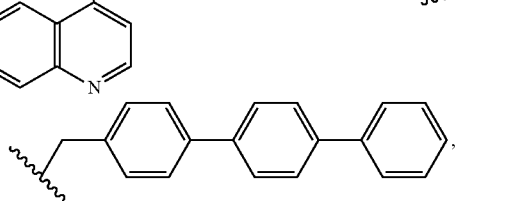

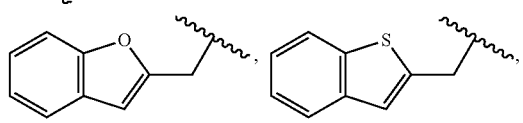

-continued

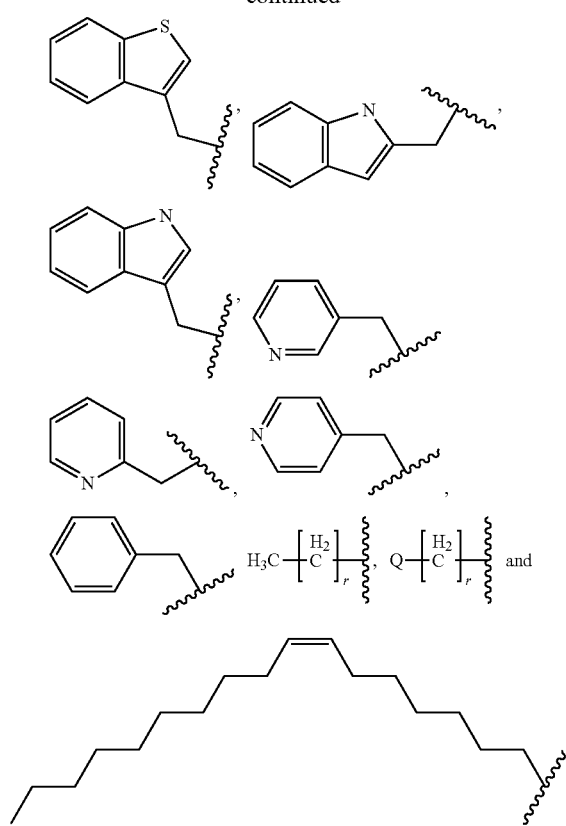

wherein,
Q can be halogen, cyano, nitro, amino, hydroxyl or alkoxy;
r is an integer ranging from 1 to 20,
$R_6$ is a side chain of an amino acid; and
V is selected from a group consisting of hydrogen,

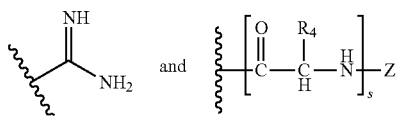

wherein 's' ranges from 1 to 5
wherein, Z is hydrogen or

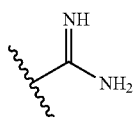

In still another embodiment of the disclosure $R_1$ is selected from a group consisting of:

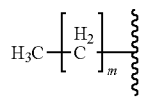

$R_2$ is

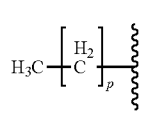

wherein 'p' ranges from 1 to 13;
$R_3$ is the side chain of L-lysine
Y is hydrogen.
In still another embodiment of the disclosure $R_1$ is selected from a group consisting of:

$$H_3C-\left[\begin{array}{c}H_2\\C\end{array}\right]_m$$

wherein 'm' ranges from 1-11.
$R_2$ is selected from a group consisting of:

$$H_3C-\left[\begin{array}{c}H_2\\C\end{array}\right]_p$$

wherein 'p' ranges from 1-11.
$R_3$ is the side chain of L-lysine
Y is hydrogen.
In still another embodiment of the disclosure $R_1$ is

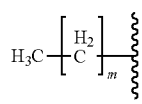

wherein 'm' is 9.

R$_2$ is

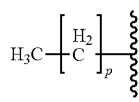

wherein 'p' is 7.

The disclosure further relates to a method of preparing a compound of formula I, wherein, said method comprises acts of:
a. reacting aldehyde of aromatic radical or aliphatic radical with an alkyl amine to obtain a schiff's base;
b. reducing the schiff's base to obtain a secondary amine; and
c. reacting the secondary amine with a free acid group of tert-butoxy carbamate protected amino acid or carboxylic acid group of the C-terminal of a peptide in which other reactive functional groups are protected, followed by deprotection of protecting groups of the amino acid or of the peptide to obtain the compound of formula I.

In still another embodiment of the disclosure in the method as mentioned above, wherein in the said method alkyl amine is $C_1$-$C_{20}$ aliphatic amine preferably $C_2$-$C_{14}$ aliphatic amine.

The disclosure further relates to a pharmaceutically accepted salt of the compounds as mentioned above.

The disclosure further relates to a composition comprising: the compounds as mentioned above or the pharmaceutically acceptable salt of the compounds as mentioned above and a pharmaceutically acceptable excipient.

In an embodiment of the disclosure, in the composition as mentioned above, the pharmaceutically acceptable excipient is selected from the group consisting of sugar, starch, cellulose, malt, gelatine, talc, cocoa butter, suppository wax, oil, glycol, ester, agar, buffering agent, alginic acid, pyrogen-free water, isotonic saline, Ringer's solution, alcohol, lipid, surfactant, coloring agent, releasing agent, coating agent, sweetening agent, flavouring agent, perfuming agent, preservatives, antioxidants and their derivatives, or any combination thereof.

In yet another embodiment of the disclosure, the compounds, the pharmaceutically accepted salt or the composition as mentioned above is used in treatment of disease caused by pathogenic microorganism.

In still another embodiment of the disclosure the compound, the pharmaceutically accepted salt or the composition as mentioned above is used in treatment of disease caused by pathogenic microorganism, wherein the pathogenic microorganism is a bacteria.

In still another embodiment of the disclosure the compound, the pharmaceutically accepted salt or the composition as mentioned above is used in treatment of disease caused by bacteria, wherein the bacteria is a gram positive bacterium or a gram negative bacterium, or a combination thereof.

In still another embodiment of the disclosure the compound, the pharmaceutically accepted salt or the composition as mentioned above is used in treatment of disease caused by bacteria, wherein the bacteria is a drug sensitive bacterium or a drug resistant bacterium, or a combination thereof.

In still another embodiment of the disclosure the compound, the pharmaceutically accepted salt or the composition as mentioned above is used in treatment of disease caused by a drug-sensitive bacterium, wherein the drug sensitive bacterium is selected from a group consisting of *S. aureus*, *E. faecium*, *E. coli* and *P. aeruginosa*, or any combination thereof.

In still another embodiment of the disclosure the compound, the pharmaceutically accepted salt or the composition as mentioned above is used in treatment of disease caused by drug-resistant bacteria, wherein the drug-resistant bacterium is selected from a group consisting of vancomycin-resistant *E. faecium*, methicillin-resistant *S. aureus* and *K. pneumoniae*, or any combination thereof.

The present disclosure relates to the development of antimicrobial compounds which are potent against various drug-sensitive and drug-resistant pathogenic microorganisms. The disclosure further relates to the preparation of said antimicrobial compounds which mimic the properties of antimicrobial peptides and are also non-toxic.

The antimicrobial compounds of the present disclosure comprises an aromatic radical and/or an aliphatic radical, an alkyl amine and an amino acid group, wherein the aliphatic radical or alkyl amine comprises varying alkyl chain length.

In a preferred embodiment of the present disclosure, the antimicrobial compounds comprise an aromatic radical, alkyl amine and an amino acid group, wherein said alkyl amine has a varying alkyl chain length.

In an embodiment of the present disclosure, the amino acid is selected from a group comprising cationic, anionic, polar uncharged, hydrophobic and aromatic amino acids, or any combination of amino acids thereof.

In another embodiment of the present disclosure, the cationic amino acid is selected from lysine arginine, histidine or a combination thereof.

In another embodiment of the present disclosure, the anionic amino acid is selected from aspartic acid or glutamic acid, or a combination thereof.

In another embodiment of the present disclosure, the polar uncharged amino acid is selected from a group consisting of serine, threonine, cysteine, asparagine and glutamine, or any combination thereof.

In another embodiment of the present disclosure, the hydrophobic amino acid is selected from a group consisting of alanine, valine, leucine, isoleucine and methionine, or any combination thereof.

In another embodiment of the present disclosure, the aromatic amino acid is selected from a group consisting of phenylalanine, tyrosine, tryptophan and histidine, or any combination thereof.

In another embodiment of the present disclosure, the amino acid is cationic, preferably L-lysine.

In yet another embodiment of the present disclosure, the antimicrobial compounds comprise an aromatic radical and/or aliphatic radical, alkyl amine and a peptide, wherein the aliphatic radical or alkyl amine comprises varying alkyl chain length.

In another embodiment of the present disclosure, the peptide is a dipeptide, a tripeptide or a polypeptide.

In an embodiment of the present disclosure, the aromatic radical is preferably selected from a group comprising but not limited to phenyl, benzyl, naphthalenyl, anthracenyl, pyridyl, quinoyl, isoquinoyl, pyrazinyl, quinoxalinyl, acridinyl, pyrimidinyl, quinazolinyl, pyhdazinyl, cinnolinyl, imidazolyl, benzimidazolyl, purinyl, indolyl, furanyl, benzofuranyl, isobenzofuranyl, pyrrolyl, indolyl, isoindolyl, thiophenyl, benzothiophenyl, pyrazolyl, indazolyl, oxazolyl, benzoxazolyl, isoxazolyl, benzisoxazolyl, thiaxolyl, quanidino, benzothiazolyl radicals or any combination thereof, wherein the aromatic radical is linked to an alkyl radical at either ortho or meta or para position or any combination of positions thereof, and wherein said alkyl radical is either a methyl or an ethyl moiety. The structural representation of the said aromatic radicals is illustrated as follows:

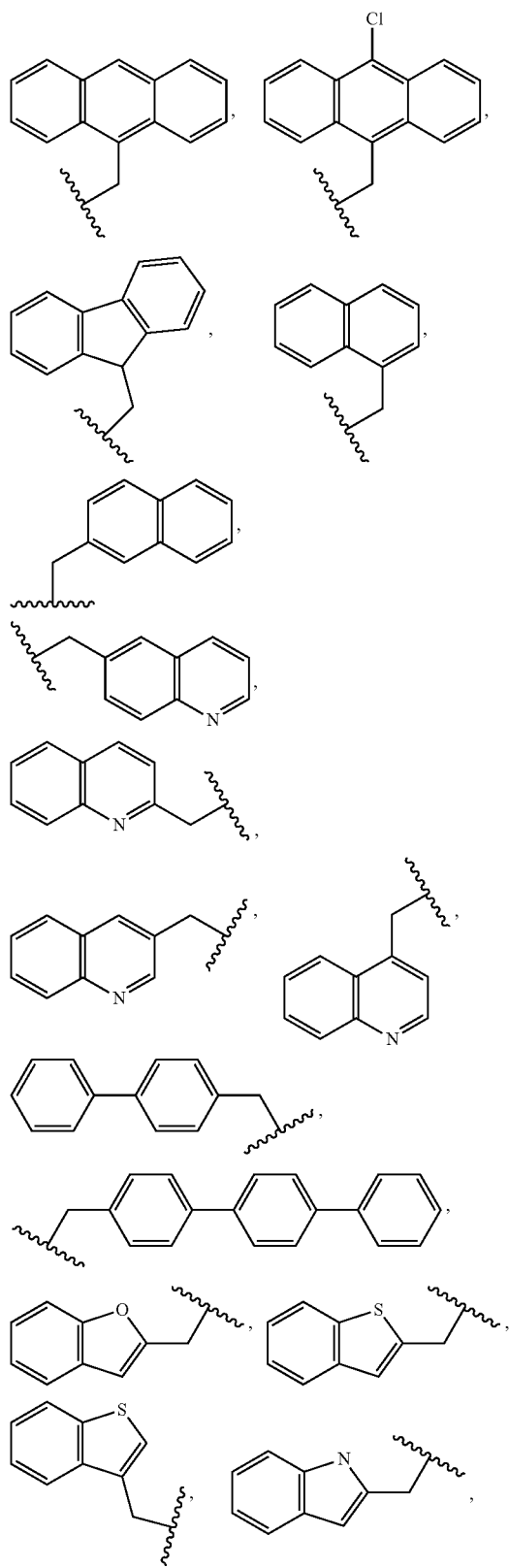

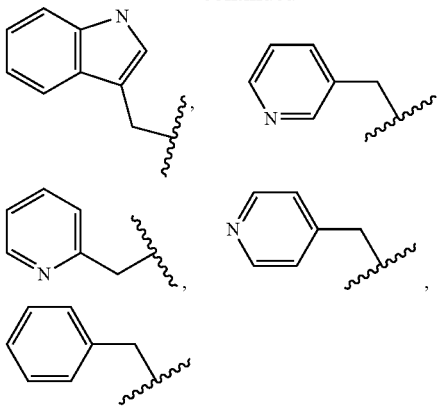

In an embodiment of the present disclosure, the aliphatic radical is an alkyl chain of varying length, wherein the length of alkyl chain ranges from about $C_1$ to about $C_{20}$. In a preferred embodiment, the length of the alkyl chain ranges from about $C_4$ to about $C_{14}$. In a more preferred embodiment, the length of the alkyl chain ranges from about $C_5$ to $C_{19}$. The general representation of the said aliphatic radical is illustrated as follows.

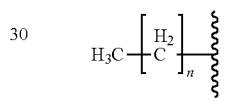

wherein, 'n' ranges from $C_1$ to $C_{20}$, preferably from $C_4$ to $C_{20}$, more preferably from $C_5$ to $C_{19}$.

In an embodiment of the present disclosure, the amino acid can be selected from a group consisting of but not limited to alanine (Ala), arginine (Arg), asparagine (Asn), aspartic acid (Asp), cysteine (Cys), glutamic acid (Glu), glutamine (Gln), glycine (Gly), histidine (His), homocysteine (Hey), homoserine (Hse), isoleucine (Ile), leucine (Leu), lysine (Lys), methionine (Met), norleucine (Nle), norvaline (Nva), ornithine (Orn), penicillamine (Pen), phenylalanine (Phe), proline (Pro), serine (Ser), tyrosine (Thr), threonine (Trp), tryptophan (Tyr), valine (Val), pyroglutamic acid (pGLU), dinitrobenzylated lysine (dnp-LYS), phosphorylated threonine (pTHR), phosphorylated serine (pSER), phosphorylated tyrosine (pTYR), citrulline (CIT), N-methylated alanine (nme-ALA), N-methylated isoleucine (nme-ILE), N-methylated leucine (nme-LEU), N-methylated phenylalanine (nme-PHE). N-methylated valine (nme-VAL), N-methylated serine (nme-SER), N-methylated threonine (nme-THR), N-methylated tyrosine (nme-TYR), alpha amino-butyhc acid (alpha-ABA), iso-aspartic acid (iso-ASP), acetylated lysine (Ac-LYS), 2-methyl alanine (2-Me-ALA) and oxamic Acid (OXA).

In another embodiment of the present disclosure the side chain of the amino acid mentioned above can be selected from H—, $CH_3$, $HN=C(NH_2)$—NH—$(CH_2)_3$—, $H_2N$—CO—$CH_2$—, HOOC—$CH_2$—, HS—$CH_2$—, $H_2N$—CO—$(CH_2)_2$—, HS—$(CH_2J_2$-, HOOC—$(CHz)_2$-, $CH_3$—$CH_2$—$CH(CH_3)$—, $(CH_3)_2CH$—$CH_2$—, $H_2N$—$(CH_2)_4$—, $CH_3$—S—$(CH_2)$—, Phenyl-$CH_2$—, HO—$CH_2$—, $CH_3$—CH(OH)—, 4-OH-Phenyl-$CH_2$—, $CH_3$—$CH(CH_3)$—,

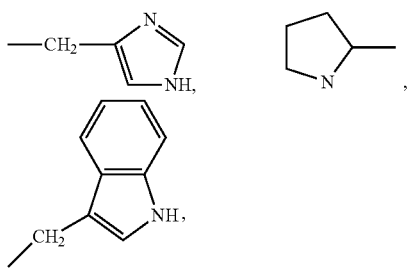

and derivatives thereof.

In an exemplary embodiment of the present disclosure, the side chain of the compounds as mentioned above, is —$CH_2$—$CH_2$—$CH_2$—$CH_2$—$NH_2$, the said amino acid is L-Lysine.

In an exemplary embodiment of the present disclosure, for compounds comprising anthracene or chloroanthracene as an aromatic radical, the alkyl chain length of the alkyl amine ranges from about $C_2$-$C_{10}$.

In another exemplary embodiment of the present disclosure, for compounds comprising naphthalene as an aromatic radical, the alkyl chain length of the alkyl amine ranges from about $C_4$-$C_{12}$.

In yet another exemplary embodiment of the present disclosure, for compounds comprising benzene as an aromatic radical, the alkyl chain length of the alkyl amine ranges from about $C_4$-$C_{14}$.

In an embodiment of the present disclosure, the compounds with 9-Chloroanthracene as an aromatic radical is referred herein as ACK, wherein 10-Aminomethyl-9-chloroanthracene moiety in the compound forms the hydrophobic core, having attached thereto, through the N atom, an L-lysine moiety and an alkyl chain comprising 2-10 carbon atoms (illustrated in FIG. 1). Further, the ACK with a varying alkyl chain carbon length is designated a number with respect to the length of the carbon in the alkyl chain. For instance, ACK comprising ethyl as alkyl chain is referred as ACK-2. Similarly, ACK comprising butyl chain is referred as ACK-4, ACK comprising hexyl chain is referred as ACK-6, ACK comprising octyl chain is referred as ACK-8 and ACK comprising decyl chain is referred as ACK-10. Further, all the said compounds with varying alkyl chain length are evidently illustrated in FIG. 1.

In another embodiment of the present disclosure, compounds with naphthalene as an aromatic radical is referred herein as NCK, wherein Aminomethyl naphthalene moiety in the compound forms the hydrophobic core, having attached thereto, through the N atom, an L-lysine moiety and an alkyl chain comprising 4-12 carbon atoms (illustrated in FIG. 1). Further, the NCK with a varying alkyl chain carbon length is designated a number with respect to the length of the carbon in the alkyl chain. For instance, NCK comprising butyl as alkyl chain is referred as NCK-4. Similarly, NCK comprising hexyl chain is referred as NCK-6, NCK comprising octyl chain is referred as NCK-8, NCK comprising decyl chain is referred as NCK-10 and NCK comprising dodecyl chain is referred as NCK-12. Further, all the compounds with varying alkyl chain length are evidently illustrated in FIG. 1.

In yet another embodiment of the present disclosure, compounds with benzene as an aromatic core is referred herein as BCK, wherein Aminomethyl benzene moiety in the compound forms the hydrophobic core, having attached thereto, through the N atom, an L-lysine moiety and an alkyl chain comprising 4-14 carbon atoms (illustrated in FIG. 1). Further, the BCK with a varying alkyl chain carbon length is designated a number with respect to the length of the carbon in the alkyl chain. For instance, BCK comprising butyl as alkyl chain is referred as BCK-4. Similarly, BCK comprising hexyl chain is referred as BCK-6, BCK comprising octyl chain is referred as BCK-8, BCK comprising decyl chain is referred as BCK-10, BCK comprising dodecyl chain is referred as BCK-12 and BCK comprising tetradecyl chain is referred as BCK-14. Further, all the compounds with varying alkyl chain length are evidently illustrated in FIG. 1.

The present disclosure addresses some of the problems of the prior art without compromising on the antimicrobial efficacy of the naturally occurring AMPs. The compounds disclosed herein involve simple design, facile synthetic methodology and cheap starting materials.

In an embodiment, one significant feature of the compounds of the instant disclosure is the incorporation of the N-disubstituted or tertiary amide bond, which contributes significantly to the abiotic nature of the design.

The disclosure further relates to a method of synthesizing various compounds as provided herein, wherein the method comprises acts of reacting aldehydes of aromatic radical or aliphatic radical with alkyl amine (carbon length varying from about $C_1$ to $C_{20}$, preferably from about $C_2$ to $C_{14}$). The aldehyde forms a Schiff's base, which is then reduced by Sodium borohydride to form secondary amines. Salts of these secondary amines are coupled to free acid group of amino acid(s) [wherein the functional groups of amino acid (apart from carboxylic group) is protected by tertiary butyl carbamate group or Boc] using O-Benzotriazole-N,N,N',N'-tetramethyl-uronium-hexafluorophosphate (HBTU) coupling chemistry. Finally the tertiarybutyl carbamate groups are deprotected using Trifluoroacetic acid to obtain the compounds defined by formula I. The compounds obtained are purified by purification techniques (preferably HPLC) and characterized using NMR, IR and Mass-Spectrometry.

In an embodiment, the salt forms of the compounds of the present disclosure are also disclosed.

In some embodiments, a pharmaceutically acceptable salt of the compounds of the present disclosure with a pharmaceutically acceptable mineral acid or organic acid include hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenylsulfonic acid, carbonic acid, succinic acid, citric acid, benzoic acid, acetic acid, trifluoroacetic acid, salicylic acid, terephthalic acid and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, trifluoroacetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, ghydroxybutyrate, glycollate, tartrate, methanesulfonate, propanesulfonate, naphthalene-1-sulfonate, naphthalene-2-sulfonate, mandelate, chloride, bromide, iodide, salicylate, 4-aminosalicylate, phosphomycin ((−)-(1R,2S)-(1,2-Epoxypropyl)phosphonate) and terephthalate and the like.

In some embodiments, a pharmaceutically acceptable salt of the compounds of the present disclosure are with a pharmaceutically acceptable organic acid such as hydrobromic acid and the pharmaceutically acceptable salt may be bromide. It should be recognized that the particular counterion forming a part of any salt of this invention may not be of a critical nature, so long as the salt as a whole is pharmacologically acceptable and as long as the counter ion does not contribute undesired qualities to the salt as a whole.

In another embodiment, the compounds or salts thereof of the present disclosure are employed to arrive at compositions optionally along with pharmaceutically acceptable excipients. Said composition is formulated to dosage forms in order to treat infection or disease caused by pathogenic microorganism. Further, the excipients are selected from a group comprising sugar, starch, cellulose, malt, gelatin, talc, cocoa butter, suppository wax, oil, glycol, ester, agar, buffering agent, alginic acid, pyrogen-free water, isotonic saline, Ringer's solution, alcohol, lipid, surfactant, coloring agent, releasing agent, coating agent, sweetening agent, flavouring agent, perfuming agent, preservatives, antioxidants and their derivatives, or any combination thereof.

In some embodiments, substrates may be coated with the compounds or compositions of the present disclosure. Examples of substrates that may be coated with the antimicrobial compositions include, but are not limited to personal care products, healthcare products, household product, food preparation surfaces, food packaging surfaces, medical devices, wound dressings, surgical staples, membranes, shunts, surgical gloves, tissue patches, prosthetic devices, wound drainage tubes, blood collection and transfer devices, tracheotomy devices, intraocular lenses, laboratory devices, textile products, and painted surfaces.

The compounds or compositions of the present disclosure are administered separately or in combination with any other drug or therapeutic agent. Examples of other therapeutic agents and/or drugs that are administered with the compounds and/or formulations/compositions of the present disclosure include, but are not limited to, beta lactam antibiotics, such as penems, penams, cephems, carbapenems, oxacephems, carbacephems, and monobactams, or other antibiotics such as cycloserine and fosfomycin. The other therapeutic agent need not be an antibiotic.

The compounds or compositions of the present disclosure are administered to the subject in a therapeutically effective amount, wherein the subject is preferably a human, in an amount ranging from about 0.25 to about 2 grams per day. The compounds or compositions of the present disclosure are administered in a single daily dosage or in multiple doses per day. Other periodic treatment protocols or alternate dosage regime are also adopted to overcome the infection or the disease caused by the microorganism. The treatment protocol may require administration over extended periods of time, e.g., for several days or for from about one to six weeks. Further, the therapeutically effective amounts of the compounds or compositions of the present disclosure discussed above are merely exemplary, the amount per administered dose or the total amount administered will depend on factors such as the nature and severity of the infection, the age and general health of the patient, the tolerance of the patient to the compounds or compositions/formulations of the present disclosure and the microorganism or microorganisms involved in the infection.

The compounds or compositions of the present disclosure are used to form contact-killing coatings or layers on a variety of substrates including personal care products (such as toothbrushes, contact lens cases and dental equipment), healthcare products, household products, food preparation surfaces and packaging, and laboratory and scientific equipment. Further, other substrates include medical devices such as catheters, urological devices, blood collection and transfer devices, tracheotomy devices, intraocular lenses, wound dressings, sutures, surgical staples, membranes, shunts, gloves, tissue patches, prosthetic devices (e.g., heart valves) and wound drainage tubes. Still further, other substrates include textile products such as carpets and fabrics, paints and joint cement. A further use is as an antimicrobial soil fumigant.

Enteral administration of the compounds or compositions of the present disclosure is preferably administered at a dosage of from about 0.01 mg/kg to about 100 mg/kg, more preferably from about 2 mg/kg to about 50 mg/kg, and most preferably from about 5 mg/kg to about 30 mg/kg.

Parenteral administration of the compounds or compositions of the present disclosure is preferably administered at a dosage from about 0.01 mg/kg to about 100 mg/kg, more preferably from about 1 mg/kg to about 30 mg/kg, and most preferably from about 5 mg/kg to about 25 mg/kg.

Topical administration of the compounds or compositions of the present disclosure is preferably administered at a dosage from about 0.000001% to about 20%, more preferably from about 0.001% to about 15%, and most preferably from about 0.025% to about 10%.

Inhalational administration of the compounds or compositions of the present disclosure is preferably administered at a dosage from about 0.0001 mg to about 25 mg, more preferably from about 0.01 mg to about 15 mg, and most preferably from about 0.1 mg to about 10 mg.

In an embodiment, the compounds or compositions of the present disclosure are used for the treatment and prevention of infectious diseases, such as diseases caused by a variety of microorganisms including but not limited to Gram-positive bacteria, Gram-negative bacteria, mycobacteria, filamentous fungi, yeast, protozoa and the like including parasites and viruses. Skilled artisans will appreciate that the compounds of present disclosure will be subjected for treatment against a variety of other microorganisms and diseases.

In another embodiment, treatment includes preventing a disease or condition from occurring in a subject which may be predisposed to the disease but has not yet been diagnosed as having it. In some other embodiments, treatment includes inhibiting the disease or condition, i.e. arresting its development; relieving the disease or condition, i.e. causing regression of the condition; or relieving the conditions caused by the disease, i.e. symptoms of the disease.

In an embodiment, compounds or composition of the present disclosure exhibits significant antibacterial activity against wild-type bacteria (drug sensitive bacteria) such as *Staphylococcus aureus, Pseudomonas aeruginosa, Escherichia coli* and *Enterococcus faecium* and drug resistant bacteria such as Methicillin resistant *S. aureus* (MRSA) and Vancomycin resistant *E. faecium* (VRE).

In another embodiment, ACK, NCK and BCK series of compounds or composition exhibit significant antibacterial activity against wild-type bacteria (drug sensitive bacteria) such as *Staphylococcus aureus, Pseudomonas aeruginosa, Escherichia coli* and *Enterococcus faecium* and drug resistant bacteria such as Methicillin resistant *S. aureus* (MRSA) and Vancomycin resistant *E. faecium* (VRE).

In yet another embodiment, the minimum inhibitory concentration of ACK compounds or compositions with an alkyl carbon length of ethyl to decyl ranges from about 2.2 µg/ml to about 7 µg/ml, wherein the compounds ACK-6 and ACK-10 exhibit the effective minimum inhibitory concentration in the range of about 2 µg/ml to about 2.5 µg/ml.

In still another embodiment, the minimum inhibitory concentration of NCK compounds or compositions with an alkyl carbon length of butyl to dodecyl ranges from about >100 µg/ml to about 2.5 µg/ml, wherein the compounds NCK-10 and NCK-12 exhibit the effective minimum inhibitory concentration in the range of about 2.5 µg/ml to about 3 µg/ml.

In still another embodiment, the minimum inhibitory concentration of BCK compounds or compositions with an alkyl carbon length of butyl to dodecyl ranges from about >100 µg/ml to about 2.7 µg/ml, wherein the compounds BCK-12 and BCK-14 exhibit the effective minimum inhibitory concentration in the range of about 2.5 µg/ml to about 3 µg/ml.

The compounds or compositions of the present disclosure are effective against The Gram-positive and Gram-negative cocci which include, but are not limited to, *Aerococcus, Enterococcus, Halococcus, Leuconostoc, Micrococcus, Mobiluncus, Moraxella catarrhalis, Neisseria* (including *N. gonorrheae* and *N. meningitidis*), *Pediococcus, Peptostreptococcus, Staphylococcus* species (including *S. aureus*, methicillin-resistant *S. aureus*, coagulase-negative *S. aureus*, and *S. saprophyticus*), *Streptococcus* species (including *S. pyogenes, S. agalactiae, S. bovis, S. pneumoniae, S. mutans, S. sanguis, S. equi, S. equinus, S. thermophilus, S. morbillorum, S. hansenii, S. pleomorphus*, and *S. parvulus*), and *Veillonella*.

The compounds or compositions of the present disclosure are effective against the Gram-positive and Gram-negative straight, curved, helical/vibrioid and branched rods include, but are not limited to, *Acetobacter, Acinetobacter, Actinobacillus equuli, Aeromonas, Agrobacterium, Alcaligenes, Aquaspirillum, Arcanobacterium haemolyticum, Bacillus* species (including *B. cereus* and *B. anthracis*), *Bacteroides* species (including *B. fragilis*), *Bartonella, Bordetella* species (including *B. pertussis*), *Brochothrix, Brucella, Burkholderia cepacia, Calymmatobacterium granulomatis, Campylobacter* species (including *C. jejuni*), *Capnocytophaga, Caulobacter, Chromobacterium violaceum, Citrobacter, Clostridium* species (including *C. perfringens. C. tetani* and *C. difficile*), *Comamonas, Curtobacterium, Edwardsiella, Eikenella, Enterobacter, Erwinia, Erysipelothrix, Escherichia* species (including *E. coli*). *Flavobacterium* species (including *F. meninosepticum*), *Francisella* species (including *F. tularensis*), *Fusobacterium* (including *F. nucleatum*), *Gardnerella* species (including *G. vaginalis*), *Gluconobacter, Haemophilus* species (including *H. influenzae* and *H. ducreyi*), *Hafnia, Helicobacter* (including *H. pylori*), *Herpetosiphon, Klebsiella* species (including *K. pneumoniae*), *Kluyvera, Lactobacillus, Legionella* species (including *L. pneumophila*), *Leptotrichia, Listeria* species (including *L. monocytogenes*), *Microbacterium, Morganella, Nitrobacter, Nitrosomonas, Pasteurella* species (including *P. multocida*), *Pectinatus, Porphyromonas gingivalis, Proteus* species (including *P. mirabilis*), *Providencia, Pseudomonas* species (including *P. aeruginosa, P. mallei, P. pseudomallei* and *P. solanacearum*), *Rahnella, Renibacterium salmoninarum, Salmonella, Serratia, Shigella, Spirillum, Streptobacillus* species (including *S. moniliformis*), *Vibrio* species (including *V. cholerae* and *V. vulnificus*), *Wolinella, Xanthobacter, Xenorhabdus, Yersinia* species (including *Y. pestis* and *Y. enterocolitica*), *Zanthomonas* and *Zymomonas*.

The compounds or compositions of the present disclosure are effective against sheathed bacteria which include, but are not limited to, *Crenothrix, Leptothrix* and *Sphaerotilus*. The sulfur-oxidizing bacteria include, but are not limited to, *Beggiatoa, Gallionella, Sulfolobus, Thermothrix, Thiobacillus* species (including *T. ferroxidans*), *Thiomicrospira* and *Thiosphaera*. The sulfur or sulfate-reducing bacteria include, but are not limited to, *Desulfobacter, Desulfobulbus, Desulfococcus, Desulfomonas, Desulfosarcina, Desulfotomaculum, Desulfovibrio* and *Desulfuromonas*.

The compounds or compositions of the present disclosure are effective against fungi which include, but are not limited to, *Acremonium, Aspergillus, Blastomyces* species (including *B. dermatitidis*), *Candida* species (including *C. albicans*), *Ceratocystis, Chaetomium, Coccidioides* species (including *C. immitis*), *Cryptococcus neoformans, Epidermophyton, Fusarium* species (including *F. oxysporum*), *Gongronella, Histoplasma* species (including *H. capsulatum*), *Hormonea, Malassezia furfur, Microsporum, Mycosphaerella fijiensis, Paracoccidiodes brasiliensis, Penicillium, Pneumocystis carinii, Pythium, Rhizoctonia, Rhodotorula, Saccharomyces, Sporothrix schenckii, Torula, Trichoderma, Trichophyton* species (including *T. mentagrophytes* and *T. rubrum*) and *Trichothecium*.

The compounds or compositions of the present disclosure are effective against parasites which include, but are not limited to, *Acanthamoeba* species, *Ascaris lumbricoides, Babesia, Balamuthia, Balantidium, Blastocystis* species including *B. hominis, Chilomastix, Clonorchis sinensis, Cryptosporidium parvum, Cyclospora, Dientamoeba fragilis, Diphyllobothrium, Echinococcus, Endolimax, Entamoeba* species (including *E. histolytica*), *Enterobius* species (including *E. vermicularis*), *Giardia lamblia*, hookworms (including *Necator, Ancylostoma*, and *Unicinaria*), *Hymenolepsis, Iodamoeba, Isospora, Leishmania, Mansonella, Microsporidia, Microsporidium, Naegleria fowleri, Onchocerca, Plasmodium* (including *P. falciparum, P. vivax, P. malariae*, and *P. ovale, P. berghei, P. yoelii*), *Schistosoma* (including *S. haematobium* and *S. mansoni*), *Strongyloides* species (including *S. stercoralis*), tapeworms (including *Taenia* species), *Toxoplasma* (including *T. gondii*), *Trichinella* (including *T. spiralis*), *Trichomonas vaginalis, Trichuris* species including *T. trichiura, Dirofilaria, Brugia, Wuchereria, Trypanosoma, Vorticella, Eimeria* species, *Hexamita* species and *Histomonas meleagidis*.

The compounds or compositions of the present disclosure are effective against viruses which include, but are not limited, to adenovirus, arborviruses (including hanta virus), astrovirus, coronavirus, cytomegalovirus, enteroviruses (including coxsackievirus A), Epstein-Barr virus, hepatitis A virus, hepatitis B virus, herpes viruses (including herpes simples virus or HSV), human immunodeficiency virus (HIV), human papilloma virus, human T-cell leukemia virus, influenza virus, mumps virus, Norwalk viruses, orbivirus, parainfluenzae viruses, parvovirus B19, poxviruses, Rabies virus, respiratory syncytial virus, rhinovirus, rotavirus, Rubella virus, varicella-zoster virus, vesicular stomatitis virus, cauliflower mosaic virus, cowpea mosaic virus, cowpox virus and rabbit myxomatis virus.

In an embodiment, the description herein provides definition to specific terms in order to clearly and concisely describes the subject matter of the claimed invention.

The singular forms "a" "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least each numerical parameter should at least be construed in light of the number of reported significant digits and by applying ordinary rounding techniques.

As used herein the term "aliphatic radical" refers to an organic radical having a valence of at least one comprising a linear or branched acyclic or non-aromatic cyclic array of atoms. The non-aromatic cyclic aliphatic radical may comprise one or more noncyclic components. For example, a cyclohexylmethyl group ($C_6H_{11}CH_2$—) is a cycloaliphatic radical which comprises a cyclohexyl ring (the array of atoms which is cyclic but which is not aromatic) and a methylene group (the noncyclic component). The array of atoms comprising the aliphatic radical may include heteroatoms such as nitrogen, sulfur, silicon, selenium and oxygen or may be composed exclusively of carbon and hydrogen. For convenience, the term "aliphatic radical" is defined herein to encompass, as part of the "linear or branched acyclic or non-aromatic cyclic array of atoms" organic radicals substituted with a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups, for example carboxylic acid derivatives such as esters and amides (including secondary amides, tertiary amides), amine groups, nitro groups, amino acids, peptides and the like.

For example, the 4-methylpent-1-yl radical is a $C_6$ aliphatic radical comprising a methyl group, the methyl group being a functional group which is an alkyl group. Similarly, the 4-nitrobut-1-yl group is a $C_4$ aliphatic radical comprising a nitro group, the nitro group being a functional group. Again, the prop-1-enyl radical ($CH_3CH$=$CH$—) is a $C_3$ aliphatic radical comprising an alkenyl group. Examples of non-aromatic cyclic radicals include but are not limited to steroids such as cholesterol and ergosterol. An aliphatic radical may be a haloalkyl group which comprises one or more halogen atoms which may be the same or different. Halogen atoms include, for example; fluorine, chlorine, bromine, and iodine. Aliphatic radicals comprising one or more halogen atoms include the alkyl halides trifluoromethyl, bromodifluoromethyl, chlorodifluoromethyl, hexafluoroisopropylidene, chloromethyl, difluorovinylidene, trichloromethyl, bromodichloromethyl, bromoethyl, 2-bromotrimethylene (e.g. —$CH_2CHBrCH_2$—), and the like. Aliphatic radicals comprising one or more alkenyl groups may include octadec-9-enyl radical ($CH_3(CH_2)_7CH$=$CH$ $(CH_2)_7CH_2$—), which is a $C_{18}$ aliphatic radical comprising single alkenyl group and octadec-9,12-dienyl radical ($CH_3$ $(CH_2)_4CH$=$CHCH_2CH$=$CH(CH_2)_7CH_2$—), which is a $C_{18}$ aliphatic radical comprising two alkenyl groups. Further examples of aliphatic radicals include methyl (i.e., —$CH_3$), methylene (i.e., —$CH_2$—), ethyl (—$C_2H_5$), butyl (—$C_4H_9$), hexyl (—$C_6H_{13}$), octyl (—$C_8H_{17}$), decyl ($C_{10}H_{21}$), dodecyl (—$C_{12}H_{25}$), tetradecyl (—$C_{14}H_{29}$), allyl ($CH_2$=$CHCH_2$—), propargyl ($CH$≡$CCH_2$—), aminocarbonyl (i.e., —$CONH_2$), carbonyl, 2,2-dicyanoisopropylidene (i.e., —$CH_2C(CN)_2CH_2$—), formyl (i.e. —$CHO$), hydroxymethyl (i.e. —$CH_2OH$), mercaptomethyl (i.e., —$CH_2SH$), methylthio (i.e., —$SCH_3$), methylthiomethyl (i.e., —$CH_2SCH_3$), methoxy, methoxycarbonyl (i.e., $CH_3OCO$—), nitromethyl (i.e., —$CH_2NO_2$), thiocarbonyl, trimethylsilyl (i.e., $(CH_3)_3Si$—), t-butyldimethylsilyl, 3-trimethyoxysilylpropyl (i.e., $(CH_3O)_3SiCH_2CH_2CH_2$—), vinyl, vinylidene, and the like. By way of further example, a $C_1$-$C_{10}$ aliphatic radical contains at least one but no more than 10 carbon atoms. A methyl group (i.e., $CH_3$—) is an example of a $C_1$ aliphatic radical. A decyl group (i.e., $CH_3(CH_2)_9$—) is an example of a $C_{10}$ aliphatic radical.

As used herein, the term "aromatic radical" refers to an array of atoms having a valence of at least one comprising at least one aromatic group. The array of atoms having a valence of at least one comprising at least one aromatic group may include heteroatoms such as nitrogen, sulfur, selenium, silicon and oxygen, or may be composed exclusively of carbon and hydrogen. As used herein, the term "aromatic radical" includes but is not limited to phenyl, pyridyl, furanyl, thienyl, naphthyl, phenylene, and biphenyl radicals. As noted, the aromatic radical contains at least one aromatic group. The aromatic group is invariably a cyclic structure having 4n+2 "delocalized" electrons where "n" is an integer equal to 1 or greater, as illustrated by phenyl groups (n=1), thienyl groups (n=1), furanyl groups (n=1), naphthyl groups (n=2), azulenyl groups (n=2), and anthraceneyl groups (n=3). The aromatic radical may also include nonaromatic components. For example, benzyl ($C_6H_5CH_2$—), naphthyl-1-methyl ($C_{10}H_7CH_2$—), anthracenyl-1-methyl ($C_{14}H_9CH_2$—) are aromatic radicals, which comprise a phenyl ring, a naphthyl ring, an anthracenyl ring (the aromatic group) respectively and a methylene group (the nonaromatic component). Similarly a tetrahydronaphthyl radical is an aromatic radical comprising an aromatic group ($C_6H_3$) fused to a nonaromatic component —($CH_2$)$_4$—. For convenience, the term "aromatic radical" is defined herein to encompass, as a part of "an array of atoms having a valence of at least one comprising at least one aromatic group" organic radicals substituted with a wide range of functional groups such as alkyl groups, alkenyl groups, alkynyl groups, haloalkyl groups, haloaromatic groups, conjugated dienyl groups, alcohol groups, ether groups, aldehyde groups, ketone groups, carboxylic acid groups, acyl groups, for example carboxylic acid derivatives such as esters and amides (including secondary amides and tertiary amides), amine groups, nitro groups, amino acids, peptides and the like. For example, the 10-Chloro-9-methylanthracenyl radical is a $C_{10}$ aromatic radical comprising a methyl group and a chloro group, the methyl group and chloro group being two functional groups which are an alkyl group and a halogen group respectively. Similarly, the 4-methylphenyl radical is a $C_7$ aromatic radical comprising a methyl group, the methyl group being a functional group which is an alkyl group. Similarly, the 2-nitrophenyl group is a $C_6$ aromatic radical comprising a nitro group, the nitro group being a functional group. Aromatic radicals include halogenated aromatic radicals such as 4-trifluoromethylphenyl, hexafluoroisopropylidene bis(4-phen-1-yloxy) (i.e., —$OPhC(CF_3)_2PhO$—), 4-chloromethylphen-1-yl, 3-trifluorovinyl-2-thienyl, 3-trichloromethylphen-1-yl (i.e., 3-$CCl_3$Ph-), 4-(3-bromoprop-1-yl)phen-1-yl (i.e., 4-$BrCH_2CH_2CH_2$Ph-), and the like. Examples of aromatic radical include but are not limited to, tocopherol and tocotrienol. Further examples of aromatic radicals include 4-allyloxyphen-1-oxy, 4-aminophen-1-yl (i.e., 4-$H_2$NPh-), 3-aminocarbonylphen-1-yl (i.e., $NH_2$COPh-), 4-benzoylphen-1-yl, dicyanomethylidenebis(4-phen-1-yloxy) (i.e., —OPhC(CN)$_2$PhO—), 3-methylphen-1-yl, methylenebis(4-phen-1-yloxy) (i.e., —OPhCH$_2$PhO—), 2-ethylphen-1-yl, phenylethenyl, 3-formyl-2-thienyl, 2-hexyl-5-furanyl, hexamethylene-1,6-bis(4-phen-1-yloxy) (i.e., —OPh(CH$_2$)$_6$PhO—), 4-hydroxymethylphen-1-yl (i.e., 4-HOCH$_2$Ph-), 4-mercaptomethylphen-1-yl (i.e., 4-HSCH$_2$Ph-), 4-methylthiophen-1-yl (i.e., 4-CH$_3$SPh-), 3-methoxyphen-1-yl, 2-methoxycarbonylphen-1-yloxy (e.g. methyl salicyl), 2-nitromethylphen-1-yl (i.e., 2-NO$_2$CH$_2$Ph), 3-trimethylsilylphen-1-yl, 4-tbutyldimethylsilylphenl-1-yl, 4-vinylphen-1-yl, vinylidene bis(phenyl), and the like. The term "a C$_3$-C$_{10}$ aromatic radical" includes aromatic radicals containing at least three but no more than 10 carbon atoms. The aromatic radical 1-imidazolyl (C$_3$H$_2$N$_2$—) represents a C$_3$ aromatic radical. The benzyl radical (C$_7$H$_7$—) represents a C$_7$ aromatic radical.

Aromatic radicals also include the following radicals

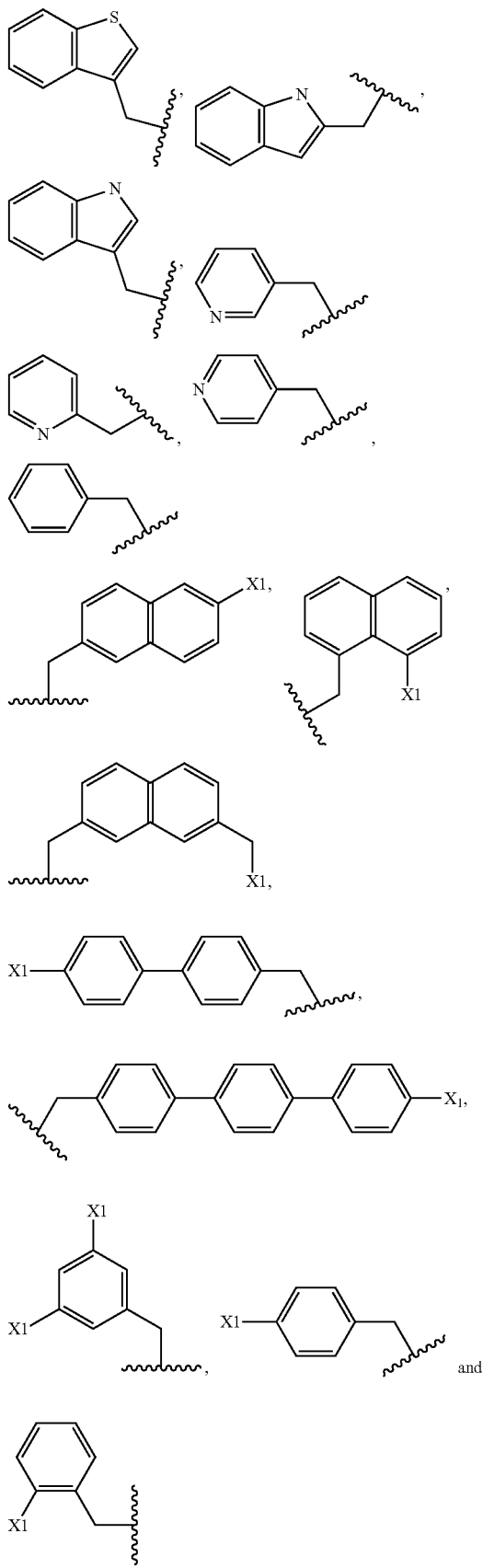

Wherein,
X₁ is

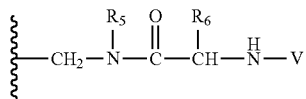

wherein,
R₅ is selected from a group consisting of the following:

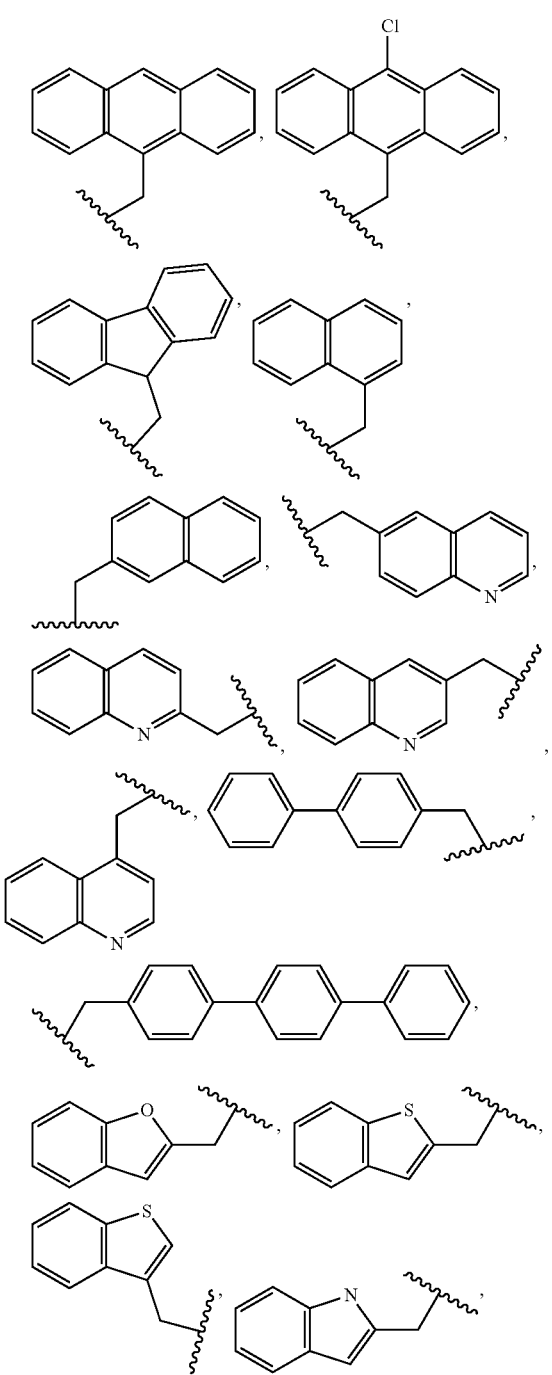

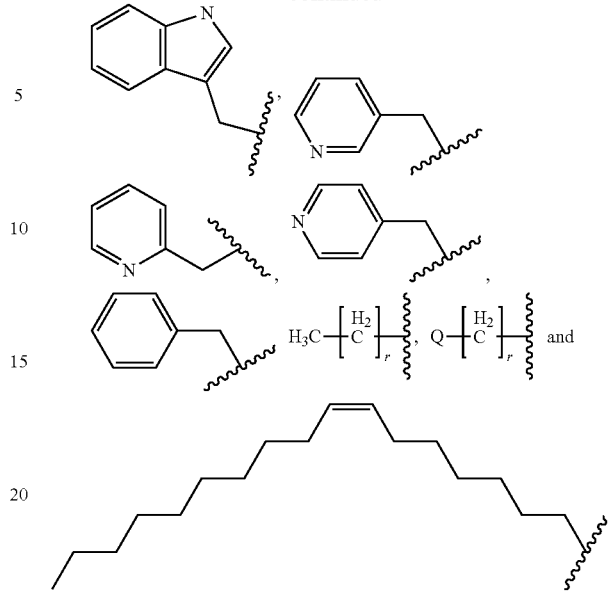

wherein,
r is an integer ranging from 1 to 20,
R₆ is a side chain of an amino acid; and
V is selected from a group consisting of hydrogen,

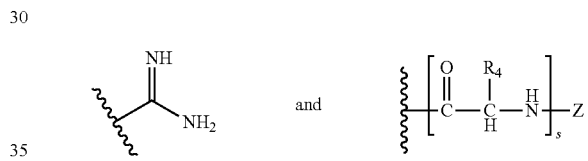

wherein, 's' ranges from 1 to 5
wherein, Z is hydrogen or

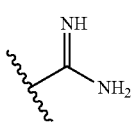

As used herein, the term "amino acid" is a compound comprising both amine and carboxyl functional groups. The carbon atom next to the carbonyl group of a carboxyl functional group is called the alpha-carbon. Amino acids with or without a substitution on the alpha-carbon are referred to as alpha amino acids. In amino acids that have an amino group and a carbon chain attached to the alpha-carbon, the carbons are labelled in order as alpha, beta, gamma, and so on from the carbonyl carbon. An amino acid which has the amino group attached to the beta or gamma-carbon is referred to as beta or gamma amino acid respectively, and so on.

An alpha amino acid is an amino acid which has amino and carboxylate groups bonded to the same carbon (the alpha carbon). The alpha carbon is one atom away from the carboxylate group. An alpha amino acid has a structure of Structure 1:

    Structure 1

Examples of alpha amino acid include, without limitation, alanine (Ala), arginine (Arg), asparagine (Asn), aspartic acid (Asp), cysteine (Cys), glutamic acid (Glu), glutamine (Gln), glycine (Gly), histidine (His), homocysteine (Hcy), homoserine (Hse), isoleucine (Ile), leucine (Leu), lysine (Lys), methionine (Met), norleucine (Nle), norvaline (Nva), ornithine (Orn), penicillamine (Pen), phenylalanine (Phe), proline (Pro), serine (Ser), tyrosine (Thr), threonine (Trp), tryptophan (Tyr), valine (Val), pyroglutamic acid (pGLU), dinitrobenzylated lysine (dnp-LYS), phosphorylated threonine (pTHR), phosphorylated serine (pSER), phosphorylated tyrosine (pTYR), citrulline (CIT), N-methylated alanine (nme-ALA), N-methylated isoleucine (nme-ILE), N-methylated leucine (nme-LEU), N-methylated phenylalanine (nme-PHE), N-methylated valine (nme-VAL), N-methylated serine (nme-SER), N-methylated threonine (nme-THR), N-methylated tyrosine (nme-TYR), alpha aminobutyhc acid (alpha-ABA), iso-aspartic acid (iso-ASP), acetylated lysine (Ac-LYS), 2-methyl alanine (2-Me-ALA) and oxamic acid (OXA).

The term "side chain" as used herein with reference to amino acids refers to a chemical group which is attached to the α-carbon atom of an amino acid, the side chain is unique for each type of amino acid, and typically does not take part in forming the peptide bond in a naturally occurring protein or polypeptide. For example, $R^1$ in structure I represents the side chain of an amino acid wherein: R' is selected from the group consisting of substituted and unsubstituted imidazolyl, substituted and unsubstituted quanidino, substituted and unsubstituted carboxyl, substituted and unsubstituted carboxamide, substituted and unsubstituted alkyl, substituted and unsubstituted cycloalkyl, substituted and unsubstituted heterocycloalkyl, substituted and unsubstituted alkoxyl, substituted and unsubstituted alkylthio, substituted and unsubstituted alkylamino, substituted and unsubstituted alkylcarbonyl, substituted and unsubstituted perfluoroalkyl, substituted and unsubstituted alkyl halide, substituted and unsubstituted aryl, and substituted and unsubstituted heteroaryl groups.

The "side chain" $R^1$ is selected from the group consisting of but not limited to H—, $CH_3$, $HN=C(NH_2)-NH-(CH_2)-$, $H_2N-CO-CH_2-$, $HOOC-CH_2-$, $HS-CH_2-$, $H_2N-CO-(CH_2)_2-$, $HS-(CH_2)_2-$, $HOOC-(CH_2)_2-$, $CH_3-CH_2-CH(CH_3)-$, $(CH_3)_2CH-CH_2-$, $H_2N-(CH_2)_4-$, $CH_3-S-(CH_2)-$, Phenyl-$CH_2-$, $HO-CH_2-$, $CH_3-CH(OH)-$, 4-OH-Phenyl-$CH_2-$, $CH_3-CH(CH_3)-$,

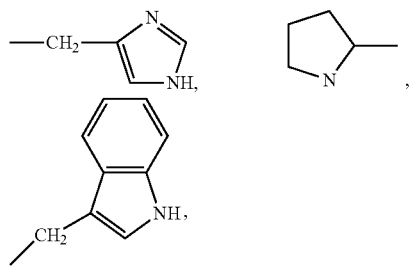

and derivatives thereof. For example, the side chain of L-Lysine is $CH_2CHCH_2CH-NH_2$, the side chain of L-Phenylalanine is $CH_2$-Ph and the side chain of L-aspartic acid is —$CH_2$—COOH.

A beta amino acid is an amino acid which has an amino group bonded to the beta carbon which is the second carbons away from the carboxylate group. Examples of beta amino acid include, without limitation, beta-alanine (β-Ala), beta-arginine (β-Arg), beta-asparagine (β-Asn), beta-aspartic acid (β-Asp), beta-cysteine (β-Cys), beta-glutamic acid (β-Glu), beta-glutamine (β-Gln), beta-histidine (β-His), beta-isoleucine (β-Ile), beta-leucine (β-Leu), beta-lysine (β-Lys), beta-methionine (β-Met), beta-phenylalanine (β-Phe), beta-proline (β-Pro), beta-serine (β-Ser), beta-tyrosine (β-Thr), beta-threonine (β-Trp), beta-tryptophan (β-Tyr) and beta-valine (β-Val).

A gamma amino acid is an amino acid which has an amino group bonded to the gamma carbon which is the third carbons away from the carboxylate group. Examples of gamma amino acid include, without limitation, gamma-glutamic acid (γ-GLU).

Furthermore, amino acids can be modified synthetically, for example amino groups may be guadinylated, acylated, alkylated, or arylated; aromatic groups may be halogenated, nitrosylated, alkylated, sulphonated, or acylated. These modifications are meant to be illustrative and not comprehensive of the types of modifications possible. Modification of the amino acids would likely add to the cost of synthesis and therefore not preferred. The tables I and II below list the genetically encoded amino acids (Table I) and non-limiting examples of non-conventional/modified amino acids (Table II) which can be used with the present invention.

TABLE 1

| Amino acid | Three-Letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Table II: list of non-conventional/modified amino acids

TABLE II list of non-conventional/modified amino acids

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
| aminoisobutyric acid | Aib | L-N-methylaspartic acid | Nmasp |

TABLE II-continued list of non-conventional/modified amino acids

| Non-conventional amino acid | Code | Non-conventional amino acid | Code |
|---|---|---|---|
| aminonorbornyl-carboxylate | Norb | L-N-methylcysteine | Nmcys |
| Cyclohexylalanine | Chexa | L-N-methylglutamine | Nmgln |
| Cyclopentylalanine | Cpen | L-N-methylglutamic acid | Nmglu |
| D-alanine | Dal | L-N-methylhistidine | Nmhis |
| D-arginine | Darg | L-N-methylisolleucine | Nmile |
| D-aspartic acid | Dasp | L-N-methylleucine | Nmleu |
| D-cysteine | Dcys | L-N-methyllysine | Nmlys |
| D-glutamine | Dgln | L-N-methylmethionine | Nmmet |
| D-glutamic acid | Dglu | L-N-methylnorleucine | Nmnle |
| D-histidine | Dhis | L-N-methylnorvaline | Nmnva |
| D-isoleucine | Dile | L-N-methylornithine | Nmorn |
| D-leucine | Dleu | L-N-methylphenylalanine | Nmphen |
| D-lysine | Dlys | L-N-methylproline | Nmpro |
| D-methionine | Dmet | L-N-methylserine | Nmser |
| D/L-ornithine | D/Lorn | L-N-methylthreonine | Nmthr |
| D-phenylalanine | Dphe | L-N-methyltryptophan | Nmtrp |
| D-proline | Dpro | L-N-methyltyrosine | Nmtyr |
| D-serine | Dser | L-N-methylvaline | Nmval |
| D-threonine | Dthr | L-N-methylethylglycine | Nmetg |
| D-tryptophan | Dtrp | L-N-methyl-t-butylglycine | Nmtbug |
| D-tyrosine | Dtyr | L-norleucine | Nle |
| D-valine | Dval | L-norvaline | Nva |
| D-α-methylalanine | Dmala | α-methyl-aminoisobutyrate | Maib |
| D-α-methylarginine | Dmarg | α-methyl-γ-aminobutyrate | Mgabu |
| D-α-methylasparagine | Dmasn | α-methylcyclohexylalanine | Mchexa |
| D-α-methylaspartate | Dmasp | α-methylcyclopentylalanine | Mcpen |
| D-α-methylcysteine | Dmcys | α-methyl-α-napthylalanine | Manap |
| D-α-methylglutamine | Dmgln | α-methylpenicillamine | Mpen |
| D-α-methylhistidine | Dmhis | N-(4-aminobutyl)glycine | Nglu |
| D-α-methylisoleucine | Dmile | N-(2-aminoethyl)glycine | Naeg |
| D-α-methylleucine | Dmleu | N-(3-aminopropyl)glycine | Norn |
| D-α-methyllysine | Dmlys | N-amino-a-methylbutyrate | Nmaabu |
| D-α-methylmethionine | Dmmet | α-napthylalanine | Anap |
| D-α-methylornithine | Dmorn | N-benzylglycine | Nphe |
| D-α-methylphenylalanine | Dmphe | N-(2-carbamylethyl)glycine | Ngln |
| D-α-methylproline | Dmpro | N-(carbamylmethyl)glycine | Nasn |
| D-α-methylserine | Dmser | N-(2-carboxyethyl)glycine | Nglu |
| D-α-methylthreonine | Dmthr | N-(carboxymethyl)glycine | Nasp |
| D-α-methyltryptophan | Dmtrp | N-cyclobutylglycine | Ncbut |
| D-α-methyltyrosine | Dmty | N-cycloheptylglycine | Nchep |
| D-α-methylvaline | Dmval | N-cyclohexylglycine | Nchex |
| D-α-methylalnine | Dnmala | N-cyclodecylglycine | Ncdec |
| D-α-methylarginine | Dnmarg | N-cyclododeclglycine | Ncdod |
| D-α-methylasparagine | Dnmasn | N-cyclooctylglycine | Ncoct |
| D-α-methylasparatate | Dnmasp | N-cyclopropylglycine | Ncpro |
| D-α-methylcysteine | Dnmcys | N-cycloundecylglycine | Ncund |
| D-N-methylleucine | Dnmleu | N-(2,2-diphenylethyl)glycine | Nbhm |
| D-N-methyllysine | Dnmlys | N-(3,3-diphenylpropyl)glycine | Nbhe |
| N-methylcyclohexylalanine | Nmchexa | N-(3-indolylyethyl)glycine | Nhtrp |
| D-N-methylornithine | Dnmorn | N-methyl-γ-aminobutyrate | Nmgabu |
| N-methylglycine | Nala | D-N-methylmethionine | Dnmmet |
| N-methylaminoisobutyrate | Nmaib | N-methylcyclopentylalanine | Nmcpen |
| N-(1-methylpropyl)glycine | Nile | D-N-methylphenylalanine | Dnmphe |
| N-(2-methylpropyl)glycine | Nile | D-N-methylproline | Dnmpro |
| N-(2-methylpropyl)glycine | Nleu | D-N-methylserine | Dnmser |
| D-N-methyltryptophan | Dnmtrp | D-N-methylserine | Dnmser |
| D-N-methyltyrosine | Dnmtyr | D-N-methylthreonine | Dnmthr |
| D-N-methylvaline | Dnmval | N-(1-methylethyl)glycine | Nva |
| γ-aminobutyric acid | Gabu | N-methyla-napthylalanine | Nmanap |
| L-t-butylglycine | Tbug | N-methylpenicillamine | Nmpen |
| L-ethylglycine | Etg | N-(p-hydroxyphenyl)glycine | Nhtyr |
| L-homophenylalanine | Hphe | N-(thiomethyl)glycine | Ncys |
| L-α-methylarginine | Marg | penicillamine | Pen |
| L-α-methylaspartate | Masp | L-α-methylalanine | Mala |
| L-α-methylcysteine | Mcys | L-α-methylasparagine | Masn |
| L-α-methylglutamine | Mgln | L-α-methyl-t-butylglycine | Mtbug |
| L-α-methylhistidine | Mhis | L-methylethylglycine | Metg |
| L-α-methylisoleucine | Mile | L-α-methylglutamate | Mglu |
| D-N-methylglutamine | Dnmgln | L-α-methylhomo phenylalanine | Mhphe |
| D-N-methylglutamate | Dnmglu | N-(2-methylthioethyl)glycine | Nmet |
| D-N-methylhistidine | Dnmhis | N-(3-guanidinopropyl)glycine | Narg |
| D-N-methylisoleucine | Dnmile | N-(1-hydroxyehtyl)glycine | Nthr |
| D-N-methylleucine | Dnmleu | N-(hydroxyethyl)glycine | Nser |
| D-N-methyllysine | Dnmlys | N-(imidazolylethyl)glycine | Nhis |
| N-methylcyclohexylalanine | Nmchexa | N-(3-indolylyethyl)glycine | Nhtrp |
| D-N-methylornithine | Dnmorn | N-methyl-γ-aminobutyrate | Nmgabu |

TABLE II-continued list of non-conventional/modified amino acids

| Non-conventional amino acid | Code | Non-conventional amino acid | Code |
| --- | --- | --- | --- |
| N-methylglycine | Nala | D-N-methylemthionine | Dnmmet |
| N-methylaminoisobutyrate | Nmaib | N-methylcyclopentylalanine | Nmcpen |
| N-(1-methylpropyl)glycine | Nile | D-N-methylphenylalanine | Dnmphe |
| N-(2-methylpropyl)glycine | Nleu | D-N-methylserine | Dnmpro |
| D-N-methyltryptophan | Dnmtrp | D-N-methylserine | Dnmser |
| D-N-methyltyrosine | Dnmtyr | D-N-methylthreonine | Dnmthr |
| D-N-methylvaline | Dnmval | N-(1-methylethyl)glycine | Nval |
| γ-aminobutyric acid | Gabu | N-methyla-napthylalanine | Nmanap |
| L-t-butylglycine | Tbug | N-methylpenicillamine | Nmpen |

As used herein the term "peptide" refers to a compound consisting of two or more amino acids linked in a chain, the carboxyl group of each acid being joined to the amino group of the next by a bond of the type —OC—NH—.

As used herein the term "dipeptide" as used herein, refers to a peptide composed of two amino acids. For example, the dipeptide Arg-Phe is a dipeptide of arginine and phenylalanine.

As used herein the term "tripeptide" as used herein, refers to a peptide composed of three amino acids linked together by two peptide bonds. For example, the tripeptide Arg-Phe-Gly is a tripeptide of arginine, phenylalanine and glycine which are linked by two peptide bonds.

As used herein the term "polypeptide" as used herein, refers to a peptide composed of more than three amino acids linked together by more than two peptide bonds.

As used herein, the term "amide bond" refers to the bond between an organic acid and an organic amine and can be represented by the structure II

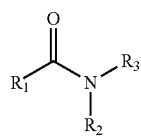

Structure-II

Wherein, if $R_1$ can be an aromatic or aliphatic radical, $R_2$ can also be an aromatic or aliphatic radical, $R_3$ is H or an aromatic or an aliphatic radical. The amide bond is a secondary amide bond when $R_3$ is H. The amide bond is a tertiary amide bond if $R_3$ is an aliphatic radical or an aromatic radical.

The term "pharmaceutically acceptable salt" as used herein, refers to salts of the compounds that are substantially non-toxic to living organisms such that it could be effectively used for the treatment of a subject. For example, the pharmacokinetics and pharmacodynamics properties of a pharmaceutically acceptable salt may be suitable for in-vivo usage. Typical pharmaceutically acceptable salts of the compounds of the subject invention include those salts, which are prepared by reaction of the compounds of the present invention with a pharmaceutically acceptable mineral acid or organic acid. Such salts are classified as acid addition salts.

The term "treatment" as used herein includes any treatment of a condition or disease in a subject and includes: (i) preventing the disease or condition from occurring in a subject which may be predisposed to the disease but has not yet been diagnosed as having it; (ii) inhibiting the disease or condition, i.e. arresting its development; relieving the disease or condition. i.e. causing regression of the condition; or relieving the conditions caused by the disease. i.e. symptoms of the disease.

The term "effective amount" as used herein is a concentration at which an active ingredient optimally performs it intended use. For example, it is an amount that is effective to prevent a disease or condition from occurring in a subject and/or inhibit the disease or condition, i.e. arrest its development; relieve the disease or condition, i.e. cause regression of the condition; or relieve the conditions caused by the disease.

The term "hydrophobic" as used herein to describe a compound of the present invention or a substituent thereon, refers to the tendency of the compound or substituent thereon to lack an affinity for, to repel or to fail to absorb water, or to be immiscible in water. The term "hydrophobic" is not meant to exclude compounds or substituents thereon that are not completely immiscible in water.

For the purpose of the present invention, the terms "lipophilic" and "hydrophobic" may be used interchangeably.

Herein throughout the phrase, "pathogenic microorganism" is used to describe any microorganism which can cause a disease or disorder in higher organism such as mammals in general and humans in particular. The pathogenic microorganism may belong to any family of organisms, such as, but not limited to prokaryotic organisms, eubacterium, archaebacterium, eukaryotic organisms such as yeast, fungi, algae, protozoa and other parasites.

"Drug resistant bacterium" as used herein is a bacterium which is able to survive exposure to at least one drug. In some embodiments the drug resistant bacterium is a bacterium which is able to survive exposure to a single drug or multiple drugs. Examples of drug resistant bacterium include but are not limited to vancomycin resistant bacterium or methicillin resistant bacterium.

The present disclosure is further illustrated by the following examples. The following examples are provided for illustrative purposes only and are not intended to limit the scope of the disclosure.

Materials Employed for Arriving at the Examples of the Instant Disclosure:

The solvents employed herein are of reagent grade and are distilled and dried prior to use wherever required. The reagents employed herein are purchased from Sigma-Aldrich, S.D. Fine, Merck and Spectrochem. They are used in the experiments described in the examples herein without further purification.

Analytical thin layer chromatography (TLC) is performed on E. Merck TLC plates pre-coated with silica gel 60 $F_{254}$ (250 μm thickness). Visualization is accomplished using UV light and Iodine. Column chromatography is performed on silica gel (60-120 mesh). HPLC analysis is performed on a Shimadzu-LC 8A Liquid Chromatograph instrument (C18 column, 10 mm diameter, 250 mm length) with UV detector monitoring at 254 nm. Nuclear magnetic resonance spectra are recorded on Bruker (AV-400) 400 MHz spectrometer in deuterated solvents. Infrared (IR) spectra of the solution of the compounds (in Chloroform or Methanol) are recorded on Bruker IFS66 V/s spectrometer using NaCl crystal. Optical density is measured by Tecan InfinitePro series M200 Microplate Reader.

Microorganisms and Culture Conditions: Bacterial strains, S. aureus (MTCC 737) and E. coli (MTCC 443) are purchased from MTCC (Chandigarh, India). MRSA (ATCC 33591), Pseudomonas aeruginosa (ATCC 4676), ☐-lactamase producing and drug-resistant Klebsiella pneumonia (ATCC700603), Enterococcus faecium (ATCC 19634) and vancomycin resistant Enterococcus faecium (ATCC 51559) are obtained from ATCC (Rockville, Md., USA).

E. coli is cultured in Luria Bertani broth (10 g of tryptone, 5 g of yeast extract, and 10 g of NaCl in 1000 mL of sterile distilled water (pH ~7) while S. aureus, Pseudomonas aeruginosa (ATCC 4676) and MRSA are grown in Yeast-dextrose broth (1 g of beef extract, 2 g of yeast extract, 5 g of peptone and 5 g of NaCl in 1000 mL of sterile distilled water). For all Enterococcus faecium, Brain Heart Infusion broth (BHI) is used. For solid media 5% agar was used along with above mentioned composition. K. pneumonia was grown in nutrient media (3 g of beef extract and 5 g of peptone in 1000 mL of sterile distilled water). The bacterial samples were freeze dried and stored at −80° C. 5 µl of these stocks were added to 3 mL of the nutrient broth and the culture was grown for 6 h at 37° C. prior to the experiments.

EXAMPLES

The following examples provide details concerning the synthesis, properties, activities, and applications of the compounds of the present disclosure. It should be understood the following is representative only, and that the disclosure is not limited by the details set forth in these examples.

Example 1

Synthesis of BOC-LYS(BOC)-OH

Lysine hydrochloride (about 5 g, 27.3 mmol) is dissolved in 50 ml $H_2O$ and to it $NaHCO_3$ (6.9 g, 82.1 mmol) is added and stirred. To this, Di-t-butylpyrocarbonate ($Boc_2O$) (7.16 g, 65.5 mmol) in 50 ml Tetrahydrofuran (THF) is added at a temperature of about 0° C. The solution is stirred at room temperature (20° C. to 35° C.) and atmospheric pressure (1 atm) for about 12 hrs. After about 12 hrs, 7.16 g, 65.5 mmol of $Boc_2O$ is added again and stirred for about 12 hrs at room temperature (20° C. to 35° C.). At the end of the reaction, THF is removed under reduced pressure and the aqueous layer is washed with diethyl ether to remove organic impurities. Then the aqueous layer is acidified to pH 4-5 using citric acid solution. Then the aqueous layer is extracted with Dichloromethane (DCM). The organic layer is then washed with brine, dried over anhydrous $Na_2SO_4$. This DCM layer is removed under reduced pressure to obtain BOC-LYS (BOC)-OH with a yield of about 90%.

($^1$H NMR: δ 5.6 (d, 1H), 4.9 (s, 1H), 4.15 (t, 1H), 3.09 (d, 2H), 1.8 (m, 1H), 1.67 (m, 1H), 1.54-1.32 (22H). [M+Na]$^+$ obsd.=369.2137 (calc.=369.2002)

Example 2

Synthesis of ACK Compounds

Example 2.1

Figure 2:
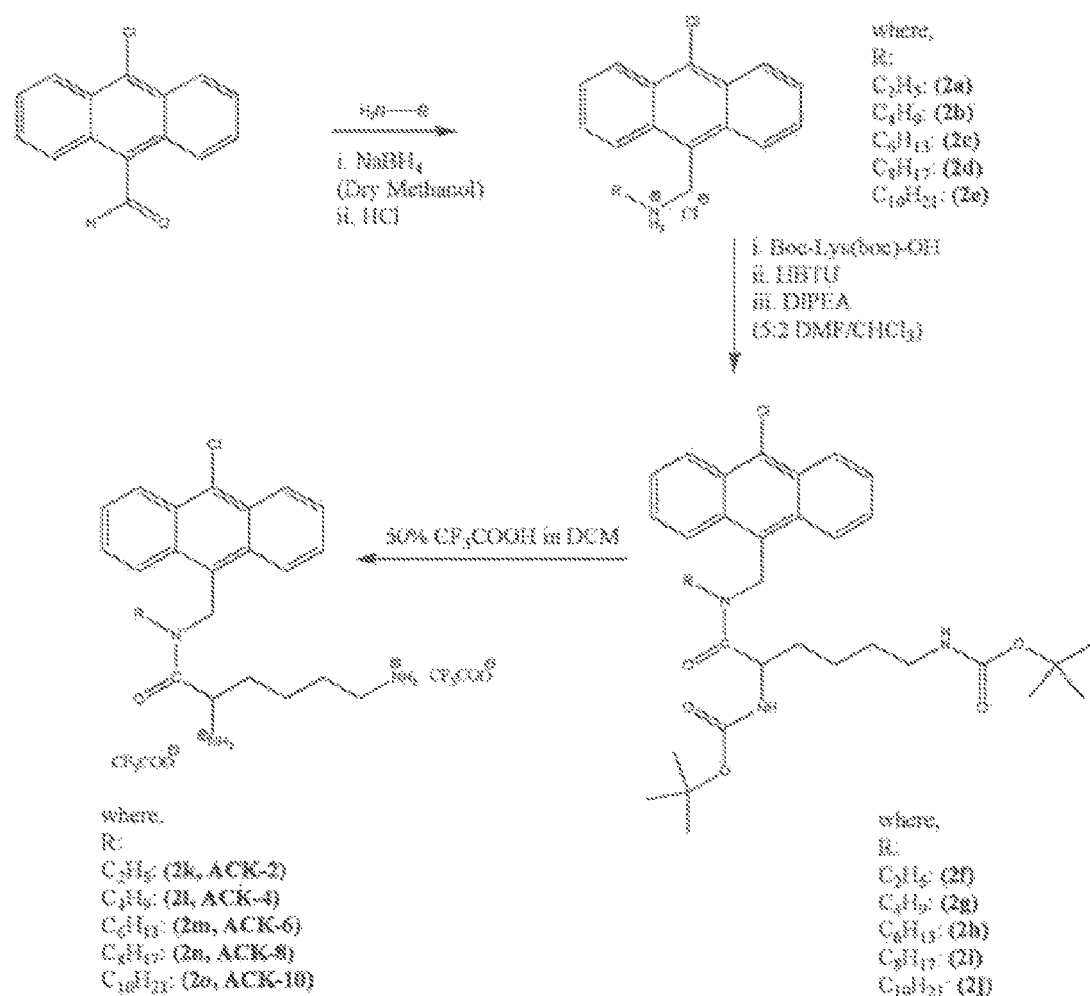
FIG. 2 represents the general synthetic scheme for the preparation of Chloro-anthracene derivatives (ACK series).

Synthesis of N-alkyl-10-Aminomethyl-9-chloroanthracene hydrochloride (compounds 2a-2e) as Furnished in FIG. 2

About 0.5 g, (2.08 mmol) of 10-chloro-9-anthraldehyde and about 2.08 mmol alkyl amines are dissolved in about 20 ml of 1:1 mixture of dry chloroform and methanol, followed by stirring at room-temperature (under Nitrogen atmosphere) for about 6 hrs. The resulting clear solution is then cooled to a temperature of about 0° C., and about 0.142 g (3.75 mmol) Sodium borohydride is added to the cooled solution. The solution is allowed to attain room temperature and stirred overnight. Then the solvents in the solution are evaporated under reduced pressure (not to dryness) and diluted with about 30 ml of diethyl ether. To this, about 20 ml of 2N NaOH is added and stirred for about 15 minutes. After separation from the NaOH layer, the organic layer is subsequently washed with water (×2), brine and dried over $MgSO_4$. The volatiles are then evaporated under reduced pressure and the residue is dissolved in minimum volume of methanol. To this about 3 ml of 4N HCl is added and instantaneous formation of precipitate is observed. The volatile components are completely removed and the precipitate is dissolved in about 5 ml of ethyl acetate (about 5 drops of methanol is added to dissolve the precipitate completely). To this hexane is added to obtain pure crystals of the target compound (N-alkyl-10-Aminomethyl-9-chloroanthracene hydrochloride) (Yield: >75%). These crystals are filtered, dried and subsequently characterized using $^1$H NMR, IR and Mass spectrometry.

The characterized profile of N-alkyl-10-Aminomethyl-9-chloroanthracene hydrochloride is illustrated below:

N-ethyl-10-aminomethyl-9-chloroanthracene hydrochloride (2a): $^1$H-NMR ($CDCl_3$) δ/ppm: 10.0 (s, Ar—$CH_2$—N$\underline{H}_2$—$C_2H_5$, 2H), 8.52 (d, Ar$\underline{H}$, 2H), 8.35 (d, Ar$\underline{H}$, 2H), 7.70 (t, Ar$\underline{H}$, 2H), 7.61 (t, Ar$\underline{H}$, 2H), 4.9 (s, Ar—C$\underline{H}_2$—$NH_2$—, 2H), 2.75 (d, —$NH_2$—C$\underline{H}_2$—$CH_3$, 2H), 1.24 (t, —$NH_2$—$CH_2$—C$\underline{H}_3$, 3H); HRMS (m/z): [M+H]$^+$ obsd.=270.1052 (calc.=270.1050).

N-butyl-10-aminomethyl-9-chloroanthracene hydrochloride (2b): $^1$H-NMR ($CDCl_3$) δ/ppm: 9.9 (s, Ar—$CH_2$—N$\underline{H}_2$—$C_4H_9$, 2H), 8.52 (d, Ar$\underline{H}$, 2H), 8.38 (d, Ar$\underline{H}$, 2H), 7.72 (t, Ar$\underline{H}$ 2H), 7.62 (t, Ar$\underline{H}$, 2H), 4.97 (s, Ar—C$\underline{H}_2$—$NH_2$—, 2H), 2.65 (d, —$NH_2$—C$\underline{H}_2$—$C_3H_7$, 2H), 1.73 (m, —$NH_2$—$CH_2$—C$\underline{H}_2$—$C_2H_5$, 2H), 1.18 (q, —$NH_2$—$C_2H_4$—C$\underline{H}_2$—$CH_3$, 2H), 0.74 (t, —$NH_2$—$C_3H_6$—C$\underline{H}_3$, 3H); HR-MS (m/z): [M+H]$^+$ obsd.=298.1337 (calc.=298.1357).

N-hexyl-10-aminomethyl-9-chloroanthracene hydrochloride (2c): $^1$H-NMR ($CDCl_3$) δ/ppm: 9.9 (s, Ar—$CH_2$—N$\underline{H}_2$—$C_6H_{13}$, 2H), 8.52 (d, Ar$\underline{H}$, 2H), 8.38 (d, Ar$\underline{H}$, 2H), 7.72 (t, Ar$\underline{H}$, 2H), 7.62 (t, Ar$\underline{H}$, 2H), 4.97 (s, Ar—C$\underline{H}_2$—$NH_2$—, 2H), 2.64 (d, —$NH_2$—C$\underline{H}_2$—$C_5H_{11}$, 2H), 1.74 (t, —$NH_2$—$CH_2$—C$\underline{H}_2$—$C_4H_9$, 2H), 1.18-1.0 (m, —$NH_2$—$C_2H_5$—(C$\underline{H}_2$)$_3$—$CH_3$, 6H), 0.74 (t, —$NH_2$—$C_5H_{10}$—C$\underline{H}_3$, 3H); HR-MS (m/z): [M+H]$^+$ obsd.=326.1670 (calc.=326.1676).

N-octyl-10-aminomethyl-9-chloroanthracene hydrochloride (2d): $^1$H-NMR ($CDCl_3$) δ/ppm: 9.9 (s, Ar—$CH_2$—N$\underline{H}_2$—$CH_{17}$, 2H), 8.52 (d, Ar$\underline{H}$, 2H), 8.38 (d, Ar$\underline{H}$, 2H), 7.72 (t, Ar$\underline{H}$, 2H), 7.62 (t, Ar$\underline{H}$, 2H), 4.97 (s, Ar—C$\underline{H}_2$—$NH_2$—, 2H), 2.64 (d, —$NH_2$—C$\underline{H}_2$—$C_7H_{14}$, 2H), 1.74 (t, —$NH_2$—

$CH_2$—$CH_2$—$C_6H_{13}$, 2H), 1.2-1.0 (m, —$NH_2$—$C_2H_5$—(C$H_2$)$_5$—$CH_3$, 10H), 0.79 (t, —$NH_2$—$C_7H_{14}$—$CH_3$, 3H); HR-MS (m/z): [M+H]$^+$ obsd.=354.1960 (calc.=354.1983).

N-decyl-10-aminomethyl-9-chloroanthracene hydrochloride (2e): $^1$H-NMR (CDCl$_3$) δ/ppm: 9.9 (s, Ar—$CH_2$—N$H_2$—$C_{10}H_{21}$, 2H), 8.52 (d, Ar$H$, 2H), 8.38 (d, Ar$H$, 2H), 7.72 (t, Ar$H$, 2H), 7.62 (t, Ar$H$, 2H), 4.97 (s, Ar—C$H_2$—$NH_2$—, 2H), 2.64 (d, —$NH_2$—$CH_2$—$C_9H_{19}$, 2H), 1.74 (t, —$NH_2$—$CH_2$—$CH_2$—$C_8H_{17}$, 2H), 1.18-1.0 (m, —$NH_2$—$C_2H_5$—($CH_2$)$_7$—$CH_3$, 14H), 0.82 (t, —$NH_2$—$C_9H_{18}$—$CH_3$, 3H); HR-MS (m/z): [M+H]$^+$ obsd.=382.2273 (calc.=382.2296).

Example 2.2

Synthesis of Boc-Lys(Boc)-N-alkyl-10-Aminomethyl-9-chloroanthracene (compounds 2f-2i) as Furnished in FIG. 2

To a stirred solution containing about 0.2 g (0.58 mmol) of Boc-Lys(Boc)-OH in about 7 ml of 5:2 DMF/CHCl$_3$, about 250 μL (1.44 mmol) of N,N-Diisopropylethylamine (DIPEA) is added at temperature of about 0° C. To this solution about 0.22 g, 0.58 mmol of HBTU is added. This mixture is stirred for about 5 minutes at about 0° C. and subsequently, about 0.48 mmol N-alkyl-10-Aminomethyl-9-chloroanthracene hydrochloride is added. The mixture is again stirred at about 0° C. for about 30 minutes and subsequently at room temperature for about 24 hrs. At the end of about 24 hrs, CHCl$_3$ is evaporated under reduced pressure and the resulting solution is diluted to 2 times its original volume by addition of ethyl acetate. This mixture is subsequently washed with 0.5 M KHSO$_4$, H$_2$O (×3) and brine. After passage through anhydrous Na$_2$SO$_4$, the volatile components are evaporated under reduced pressure and the residue is purified using column chromatography (only CHCl$_3$) to obtain Boc-Lys(Boc)-N-alkyl-10-Aminomethyl-9-chloroanthracene with an yield of about 65% to about 90%. The purified compound is subsequently characterized using $^1$H NMR, IR and Mass spectrometry.

The characterized profile of Boc-Lys(Boc)-N-alkyl-10-Aminomethyl-9-chloroanthracene is illustrated below:

Boc-Lys(Boc)-N-ethyl-10-Aminomethyl-9-chloroanthracene (2f): $^1$H-NMR (CDCl$_3$) δ/ppm: 8.61 (d, Ar$H$, 2H), 8.29 (d, Ar$H$, 2H), 7.60 (m, Ar$H$, 4H), 6.05 (d, Ar—C$H^1H^2$—N(R)Lys(boc)$_2$, 1H), 5.42 (d, α-N$H$-Boc of Lys(boc)$_2$, 1H), 5.34 (d, Ar—CH$^1H^2$—N(R)Lys(boc)$_2$, 1H), 4.56 (m, Lys (ε-N$H$-Boc)-α-N$H$-boc and α-C$H$ofLys(boc)$_2$, 2H) 3.1-2.81 (δ-$CH_2$ of Lys(boc)$_2$ and Ar—$CH_2$—N(—C$H_2$—$CH_3$)Lys(boc)$_2$, 4H), 1.5-1.3 (—CO—[CH—$CH_2$—C$H_2$—$CH_2$—NH—COO—C($CH_3$)$_3$]-NH—COO—C($CH_3$)$_3$Lys(boc)$_2$, 24H), 1.03 (t, —$CH_2$—$CH_3$ of R group, 3H). FT-IR (cm$^{-1}$): 3354 (carbamate N—H str.), 3085 (sp$^2$ C—H str.), 2967-2867 (sp$^3$ C—H str.), 1704 (C=O str. of carbamate), 1643 (C=O str. of tertiary amide), 1517-1450 (aromatic C=C str.). HRMS (m/z): [M+H]$^+$ obsd.=598.3043 (calc.=598.2969).

Boc-Lys(Boc)-N-butyl-10-Aminomethyl-9-chloroanthracene (2g): $^1$H-NMR (CDCl$_3$) δ/ppm: 8.61 (d, Ar$H$, 2H), 8.29 (d, Ar$H$, 2H), 7.60 (m, Ar$H$, 4H), 6.08 (d, Ar—C$H^1H^2$—N(R)Lys(boc)$_2$, 1H), 5.42 (d, α-N$H$-Boc of Lys (boc)$_2$, 1 H), 5.29 (d, Ar—C$H^1H^2$—N(R)Lys(boc)$_2$, 1H), 4.56 (m, Lys(ε-N$H$-Boc)-α-N$H$-boc and α-C$H$ofLys(boc)$_2$, 2H) 3.1-2.81 (δ-$CH_2$ of Lys(boc)$_2$ and Ar—$CH_2$—N(—C$H_2$—$CH_3$)Lys(boc)$_2$,4H), 1.62-1.3 (—CO—[CH—$CH_2$—C$H_2$—$CH_2$—$CH_2$—NH—COO—C($CH_3$)$_3$]-NH—COO—C($CH_3$)$_3$Lys(boc)$_2$ and —$CH_2$—C$H_2$—$C_2H_5$ of R group, 26H), 1.0 (m, —$C_2H_4$—$CH_2$—$CH_3$ of R group 2H), 0.63 (t, —$C_3H_6$—$CH_3$ of R group, 3H). FT-IR (cm$^{-1}$): 3354 (carbamate N—H str.), 3083 (sp$^2$ C—H str.), 2967-2867 (sp$^3$ C—H str.), 1711 (C=O str. of carbamate), 1631 (C=O str. of tertiary amide), 1517-1450 (aromatic C=C str.). HR-MS (m/z): [M+K]$^+$ obsd.=664.4545 (calc.=664.292).

Boc-Lys(Boc)-N-hexyl-10-Aminomethyl-9-chloroanthracene (2h): $^1$H-NMR (CDCl$_3$) δ/ppm: 8.61 (d, Ar$H$, 2H), 8.29 (d, Ar$H$, 2H), 7.60 (m, Ar$H$, 4H), 6.08 (d, Ar—C$H^1H^2$—N(R)Lys(boc)$_2$, 1H), 5.42 (d, α-N$H$-Boc of Lys(boc)$_2$, 1H), 5.29 (d, Ar—CH$^1H^2$—N(R)Lys(boc)$_2$, 1H), 4.56 (m, Lys(ε-N$H$-Boc)-α-N$H$-boc and α-C$H$ofLys(boc)$_2$, 2H) 3.1-2.81 (δ-$CH_2$ of Lys(boc)$_2$ and Ar—$CH_2$—N(—C$H_2$—$CH_3$)Lys(boc)$_2$, 4H), 1.63-1.3 (—CO—[CH—$CH_2$—C$H_2$—$CH_2$—$CH_2$—NH—COO—C($CH_3$)$_3$]-NH—COO—C($CH_3$)$_3$ of Lys(boc)$_2$ and —$CH_2$—$CH_2$—$C_4H_9$ of R group, 26H), 1.05 (m, —$C_2H_4$—$CH_2$—$C_3H_7$ of R group 2H), 0.94 (m, —$C_2H_4$—($CH_2$)$_3$—$CH_3$ of R group, 4H) 0.73 (t, —$C_5H_{10}$—$CH_3$ of R group, 3H). FT-IR (cm$^{-1}$): 3354 (carbamate N—H str.), 3085 (sp$^2$ C—H str.), 2967-2867 (sp$^3$ C—H str.), 1705 (C=O str. of carbamate), 1634 (C=O str. of tertiary amide), 1517-1450 (aromatic C=C str.). HR-MS (m/z): [M+H]$^+$ obsd.=654.3619 (calc.=654.3668).

Boc-Lys(Boc)-N-octyl-10-Aminomethyl-9-chloroanthracene (2i): $^1$H-NMR (CDCl$_3$) δ/ppm: 8.61 (d, Ar$H$, 2H), 8.29 (d, Ar$H$, 2H), 7.60 (m, Ar$H$, 4H), 6.08 (d, Ar—C$H^1H^2$—N(R)Lys(boc)$_2$, 1H), 5.42 (d, α-N$H$-Boc of Lys(boc)$_2$, 1H), 5.29 (d, Ar—CH$^1H^2$—N(R)Lys(boc)$_2$, 1 H), 4.56 (m, Lys(ε-N$H$-Boc)-α-N$H$-boc and α-C$H$ofLys(boc)$_2$, 2H) 3.1-2.81 (δ-$CH_2$ of Lys(boc)$_2$ and Ar—$CH_2$—N(—C$H_2$—$CH_3$)Lys(boc)$_2$, 4H), 1.63-1.28 (—CO—[CH—C$H_2$—$CH_2$—$CH_2$—$CH_2$—NH—COO—C($CH_3$)$_3$]-NH—COO—C($CH_3$)$_3$ of Lys(boc)$_2$ and —$CH_2$—$CH_2$—$C_6H_{13}$ of R group, 26H), 1.18 (m, —$C_2H_4$—$CH_2$—$C_5H_{11}$ of R group, 2H), 1.12-0.87 (—$C_3H_7$—($CH_2$)$_4$—$CH_3$ of R group, 8H) 0.73 (t, —$C_7H_{14}$—$CH_3$ of R group, 3H). FT-IR (cm$^{-1}$): 3354 (carbamate N—H str.), 3085 (sp$^2$ C—H str.), 2967-2867 (sp$^3$ C—H str.), 1696 (C=O str. of carbamate), 1643 (C=O str. of tertiary amide), 1517-1450 (aromatic C=C str.). HRMS (m/z): [M+H]$^+$ obsd.=682.3897 (calc.=682.3981).

Boc-Lys(Boc)-N-decyl-10-Aminomethyl-9-chloroanthracene (2j): $^1$H-NMR (CDCl$_3$) δ/ppm: 8.61 (d, Ar$H$, 2H), 8.29 (d, Ar$H$, 2H), 7.60 (m, Ar$H$, 4H), 6.08 (d, Ar—C$H^1H^2$—N(R)Lys(boc)$_2$, 1H), 5.42 (d, α-N$H$-Boc of Lys(boc)$_2$, 1H), 5.29 (d, Ar—CH$^1H^2$—N(R)Lys(boc)$_2$, 1H), 4.56 (m, Lys (ε-N$H$-Boc)-α-N$H$-boc and α-C$H$ofLys(boc)$_2$, 2H) 3.1-2.81 (δ-$CH_2$of Lys(boc)$_2$ and Ar—$CH_2$—N(—C$H_2$—$CH_3$)Lys(boc)$_2$, 4H), 1.62-1.28 (—CO—[CH—C$H_2$—$CH_2$—$CH_2$—$CH_2$—NH—COO—C($CH_3$)$_3$]-NH—COO—C($CH_3$)$_3$ of Lys(boc)$_2$ and —$CH_2$—$CH_2$—$C_8H_{17}$ of R group, 26H), 1.31-0.8 (—$CH_2$—$CH_2$—$C_8H_{17}$ of R group, 17H). FT-IR (cm$^{-1}$): 3334 (carbamate N—H str.), 3085 (sp$^2$ C—H str.), 2967-2867 (sp$^3$ C—H str.), 1704 (C=O str. of carbamate), 1643 (C=O str. of tertiary amide), 1517-1450 (aromatic C=C str.). HRMS (m/z): [M+H]$^+$ obsd.=710.4220 (calc.=710.4294).

Example 2.3

Synthesis of Lys-N-alkyl-10-Aminomethyl-9-chloroanthracene trifluoroacetates (compounds 2k-2o) as Furnished in FIG. 2

About 0.35 mmol of Boc-Lys(Boc)-N-alkyl-10-Aminomethyl-9-chloroanthracene is dissolved in about 5 ml DCM and subsequently CF3COOH (50% by volume) is added and stirred at room temperature. The reactions are monitored by TLC until complete removal of starting material is observed. All the volatile components are removed by evaporation under pressure, and the product is purified by reverse phase HPLC using 0.1% Trifluoro acetic acid (TFA) in water and acetonitrile (0-100%) as mobile phase, C18 column (10 mm diameter, 250 mm length) as stationary phase and UV detector at 270 nm wavelength is used. After drying the compounds in freeze drier, they are characterized by 1H NMR, IR and mass spectrometry.

The characterized profile of Lys-N-alkyl-10-Aminomethyl-9-chloroanthracene trifluoroacetate is illustrated below:

Lys-N-ethyl-10-Aminomethyl-9-chloroanthracene trifluoroacetate (2k, ACK-2): $^1$H-NMR (D$_2$O) δ/ppm: 8.48 (d, ArH, 2H), 8.13 (d, ArH, 2H), 7.71 (m, ArH, 4H), 5.82 (d, Ar—CH$^1$H$^2$—N(R)Lys, 1H), 5.16 (d, Ar—CH$^1$H$^2$—N(R)Lys, 1H), 4.4 (t, α-CHofLys, 1H), 3.0 (m, ε-CH$_2$ of Lys, 2H), 2.67 (m, Ar—CH$_2$—N(CH$_2$CH$_3$)Lys, 2H), 1.81 (m, γ-CH$_2$ of Lys, 2H), 1.50 (m, δ-CH$_2$ of Lys, 2H), 1.28 (m, β-CH$^1$H$^2$ of Lys, 1H), 1.16 (m, β-CH$^1$H$^2$ of Lys, 1H), 0.92 (t, N—CH$_2$CH$_3$, of R, 1H). FT-IR (cm$^{-1}$): 3414 (primary amine N—H str.), 3089 (sp$^2$ C—H str.), 2967-2867 (sp$^3$ C—H str.), 1678 (C=O str. of tertiary amide), 1517-1450 (aromatic C=C str.). HR-MS (m/z): [M+H]$^+$ obsd.=398.1976 (calc.=398.1999).

Lys-N-butyl-10-Aminomethyl-9-chloroanthracene trifluoroacetate (2l, ACK-4): $^1$H-NMR (D$_2$O) δ/ppm: 8.58 (d, ArH, 2H), 8.24 (d, ArH, 2H), 7.71 (m, ArH, 4H), 5.92 (d, Ar—CH$^1$H$^2$—N(R)Lys, 1H), 5.28 (d, Ar—CH$^1$H$^2$—N(R)Lys, 1H), 4.4 (t, α-CHofLys, 1H), 3.0 (m, ε-CH$_2$ of Lys, 2H), 2.67 (m, Ar—CH$_2$—N(CH$_2$(CH$_2$)$_2$H$_3$)Lys, 2H), 1.85 (m, γ-CH$_2$ of Lys, 2H), 1.54 (m, δ-CH$_2$ of Lys, 2H), 1.47-1.11 (β-CH$_2$ of Lys, 2H) 1-0.7 (m, Ar—CH$_2$—N(CH$_2$CH$_2$C$_2$H$_5$)Lys, 2H), 0.2 (m, Ar—CH$_2$—N(C$_2$H$_4$CH$_2$CH$_3$)Lys, 2H), 0.1 (t, Ar—CH$_2$—N(C$_3$H$_6$CH$_3$)Lys, 3H). FT-IR (cm$^{-1}$): 3414 (primary amine N—H str.), 3089 (sp$^2$ C—H str.), 2962-2867 (sp$^3$ C—H str.), 1678 (C=O str. of tertiary amide), 1517-1450 (aromatic C=C str.). HR-MS (m/z): [M+H]$^+$ obsd.=426.2283 (calc.=426.2312).

Lys-N-hexyl-10-Aminomethyl-9-chloroanthracene trifluoroacetate (2m, ACK-6): $^1$H NMR (D$_2$O) δ/ppm: 8.23 (d, ArH, 2H), 7.94 (d, ArH, 2H), 7.49 (m, ArH, 4H), 5.60 (d, Ar—CH$^1$H$^2$—N(R)Lys, 1H), 5.03 (d, Ar—CH$^1$H$^2$—N(R)Lys, 1H), 4.23 (t, α-CHofLys, 1H), 2.78 (m, ε-CH$_2$ of Lys, 2H), 2.7-2.23 (m, Ar—CH$_2$—N(CH$_2$C$_5$H$_{11}$)Lys, 2H), 1.72 (m, γ-CH$_2$ of Lys, 2H), 1.52 (m, δ-CH$_2$ of Lys, 2H), 1.41-1.19 (β-CH$_2$ of Lys, 2H) 1.0-0.7 (Ar—CH$_2$—N(CH$_2$CH$_2$C$_4$H$_9$)Lys, 2H), 0.67-0.11 (Ar—CH$_2$—N(C$_2$H$_4$-CH$_2$—CH$_2$—CH$_2$—CH$_3$)Lys, 9H). FT-IR (cm$^{-1}$): 3414 (primary amine N—H str.), 3089 (sp$^2$ C—H str.), 2967-2867 (sp$^3$ C—H str.), 1678 (C=O str. of tertiary amide), 1517-1450 (aromatic C=C str.). HR-MS (m/z): [M+H]$^+$ obsd.=454.2595 (calc.=454.2625).

Lys-N-octyl-10-Aminomethyl-9-chloroanthracene trifluoroacetate (2n, ACK-8): $^1$H NMR (D$_2$O) δ/ppm: 8.04 (d, ArH, 2H), 7.94 (d, ArH, 2H), 7.35 (m, ArH, 4H), 5.46 (d, Ar—CH$^1$H$^2$—N(R)Lys, 1H), 5.09 (d, Ar—CH$^1$H$^2$—N(R)Lys, 1H), 4.17 (t, α-CHofLys, 1H), 2.82 (m, ε-CH$_2$ of Lys, 2H), 2.57-2.29 (m, Ar—CH$_2$—N(CH$_2$C$_5$H$_{11}$)Lys, 2H), 1.73 (m, γ-CH$_2$ of Lys, 2H), 1.52 (m, δ-CH$_2$ of Lys, 2H), 1.40-1.15 (β-CH$_2$ of Lys, 2H), 1.0-0.1 (Ar—CH$_2$—N(CH$_3$—(CH$_2$)$_6$—CH$_3$)Lys, 15H). FT-IR (cm$^{-1}$): 3414 (primary amine N—H str.), 3089 (sp$^2$ C—H str.), 2967-2867 (sp$^3$ C—H str.), 1678 (C=O str. of tertiary amide), 1517-1450 (aromatic C=C str.). HR-MS (m/z): [M+H]$^+$ obsd.=482.290 (calc.=482.293).

Lys-N-decyl-10-Aminomethyl-9-chloroanthracene trifluoroacetate (2o, ACK-10): $^1$H NMR (CD$_3$OD) δ/ppm: 8.52 (d, ArH, 2H), 8.48 (d, ArH, 2H), 7.8-7.5 (ArHand Lys-ε-NH$_2$, 6H), 6.04 (d, Ar—CH$^1$H$^2$—N(R)Lys, 1H), 5.54 (d, Ar—CH$^1$H$^2$—N(R)Lys, 1H), 4.3 (t, α-CHofLys, 1H), 3.0-2.8 (ε-CH$_2$ of Lys and Ar—CH$_2$—N(CH$_2$C$_9$H$_{19}$)Lys, 4H), 1.9-1.7 (γ-CH$_2$ of Lys, 2H), 1.6-0.8 (β-CH$_2$ of Lys, δ-CH$_2$ of Lys and Ar—CH$_2$—N(CH$_3$-(CH$_2$)$_8$—CH$_3$)Lys, 23H). FT-IR (cm$^{-1}$): 3414 (primary amine N—H str.), 3089 (sp$^2$ C—H str.), 2967-2867 (sp$^3$ C—H str.), 1678 (C=O str. of tertiary amide), 1517-1450 (aromatic C=C str.). HR-MS (m/z): [M+H]$^+$ obsd.=510.3259 (calc.=510.3251).

Example 3

Figure 3:
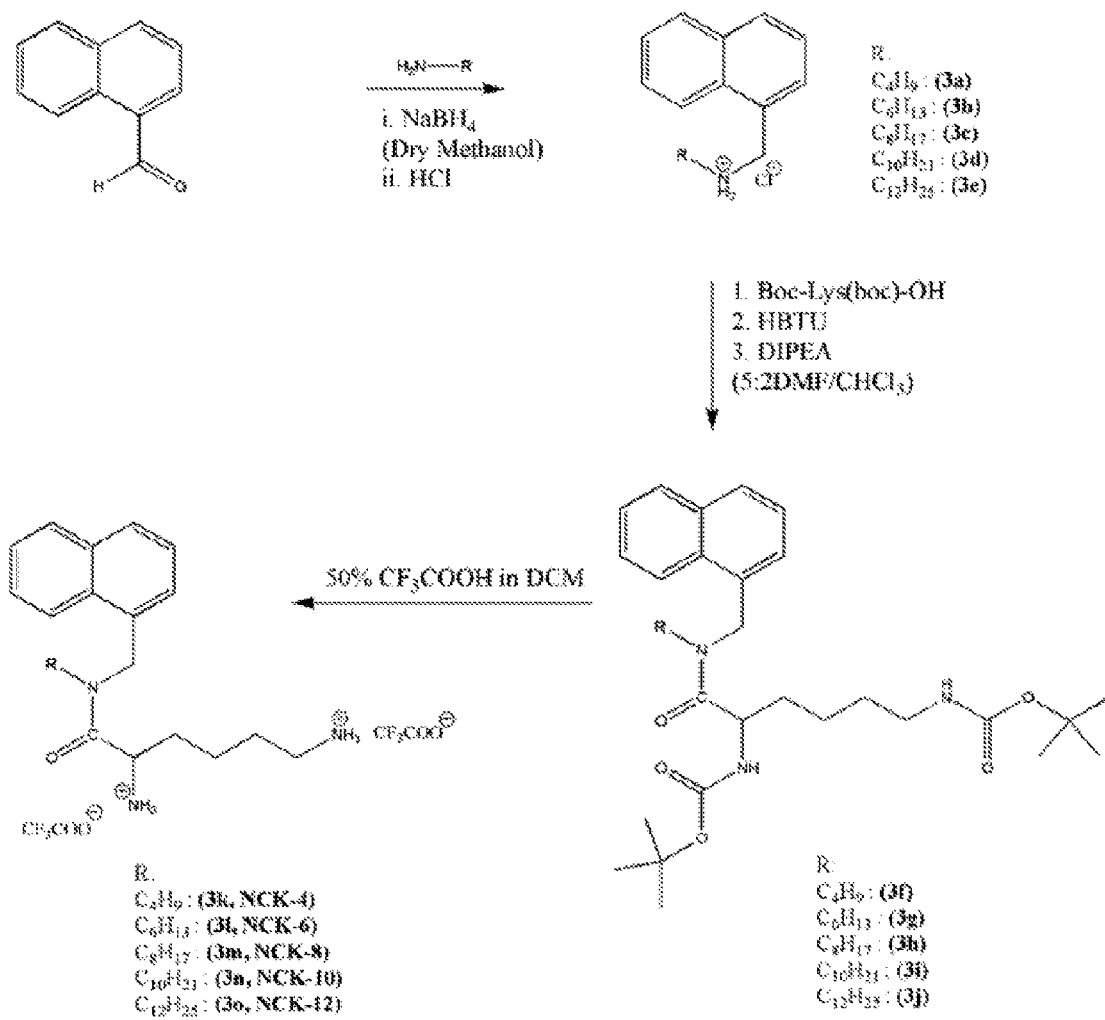
FIG. 3 represents the general synthetic scheme for the preparation of Naphthalene derivatives (NCK series).

Synthesis of NCK Compounds as Furnished in FIG. 3

Figure 5:
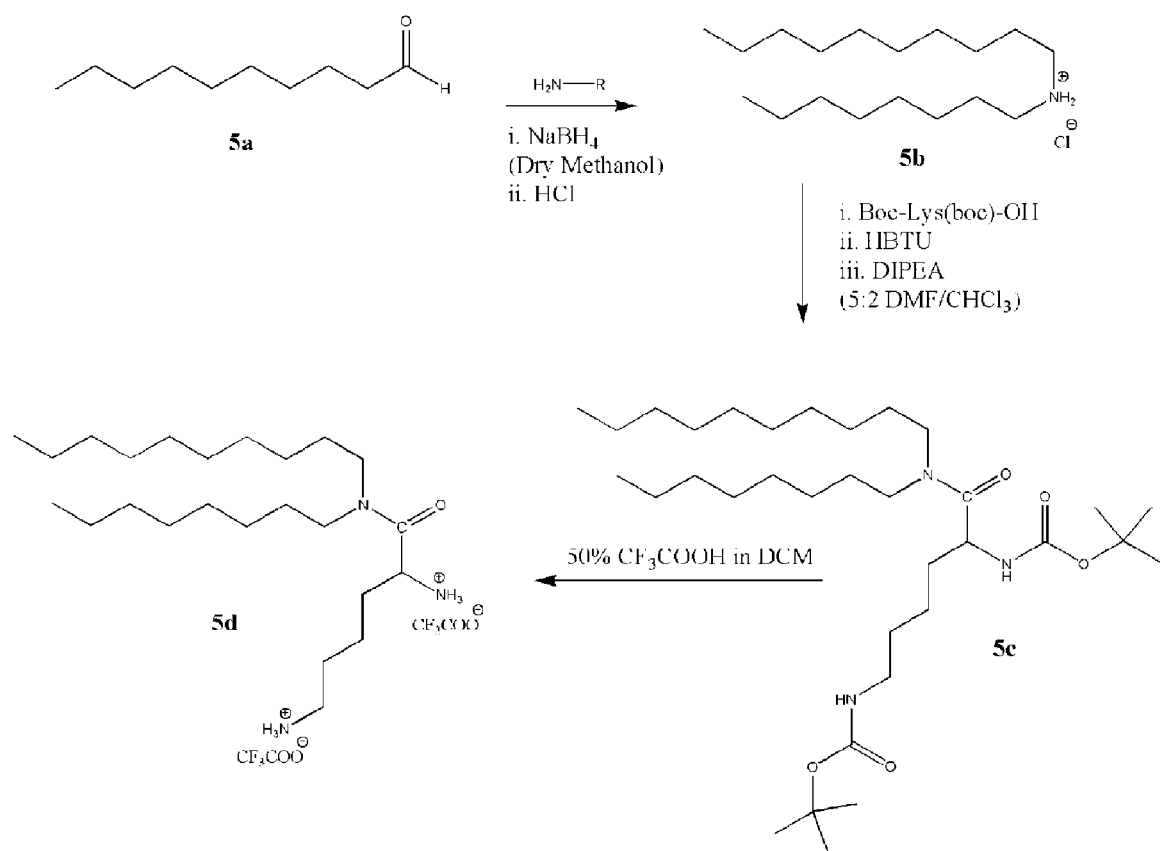
FIG. 5 represents the general synthetic scheme for the preparation of Dec-CK-8.

The compounds represented in the NCK series follow a similar protocol of preparation as the compounds mentioned in the ACK series (as illustrated in FIG. 5). The only difference is that the starting aldehyde used to couple with the alkylamines is Naphthaldehyde.

Example 3.1

Synthesis of N-alkyl-1-Aminomethylnaphthalene hydrochlorides (compounds 3a-3e) as Furnished in FIG. 3

About 0.5 g (3.2 mmol) of 1-Naphthaldehyde and about 3.2 mmol of alkyl amines are dissolved in about 20 ml of dry methanol and stirred at room-temperature (under Nitrogen atmosphere) for about 6 hrs. The resulting clear solution is then cooled to a temperature of about 0° C. To the cooled solution, about 0.218 g (5.76 mmol) of Sodium borohydride is added. The solution is allowed to attain room temperature and stirred overnight. Then the solvents in the solution are evaporated under reduced pressure (not to dryness) and diluted with diethyl ether. To this, about 20 ml of 2N NaOH is added and stirred for about 15 minutes. After separation from the NaOH layer, the organic layer is subsequently washed with water (×2), brine and dried over MgSO$_4$. The volatile components are then evaporated under reduced pressure and the residue is dissolved in about 2 mL of methanol. To this, 3 ml of 4N HCl is added and instantaneous formation of precipitate is observed. The volatiles components are completely removed and the precipitate is dissolved in minimum volume of ethyl acetate (a few drops of methanol is added to dissolve the precipitate completely). To this, hexane is added to obtain pure crystals of N-alkyl-1-Aminomethylnaphthalene hydrochlorides with an yield of about 75%. These crystals are filtered, dried and subsequently characterized using $^1$H NMR, IR and Mass spectrometry.

The characterized profile of N-alkyl-1-Aminomethylnaphthalene hydrochlorides is illustrated below:

N-butyl-1-aminomethylnaphthalene hydrochloride (3a): $^1$H NMR (CDCl$_3$) δ/ppm: 9.9 (s, Ar—CH$_2$—NH$_2$—C$_4$H$_9$, 2H), 8.12 (d, ArH, 1H), 7.85 (m, ArH, 3H), 7.64 (t, ArH, 1H), 7.52 (q, ArH, 2H), 4.5 (s, Ar—CH$_2$—NH$_2$—, 2H), 2.77 (m, —NH$_2$—CH$_2$—C$_3$H$_7$, 2H), 1.83 (m, —NH$_2$—CH$_2$—CH$_2$—C$_2$H$_5$, 2H), 1.29 (m, —NH$_2$—C$_2$H$_4$—CH$_2$—CH$_3$, 2H), 0.82 (t, —NH$_2$—C$_3$H$_6$—CH$_3$, 3H). HR-MS (m/z): [M+H]$^+$ obsd.=214.1567 (calc.=214.159).

N-hexyl-1-aminomethylnaphthalene hydrochloride (3b): $^1$H NMR (CDCl$_3$) δ/ppm: 9.9 (s, Ar—CH$_2$—NH$_2$—C$_6$H$_{13}$, 2H), 8.12 (d, ArH, 1H), 7.85 (m, ArH, 3H), 7.64 (t, ArH, 1H), 7.51 (q, ArH, 2H), 4.5 (s, Ar—CH$_2$—NH$_2$—, 2H), 2.75 (t, —NH$_2$—CH$_2$—C$_5$H$_{11}$, 2H), 1.85 (q, —NH$_2$—CH$_2$—CH$_2$—C$_4$H$_9$, 2H), 1.2 (m, —NH$_2$—C$_2$H$_5$—(CH$_2$)$_3$—CH$_3$, 6H), 0.82 (t, —NH$_2$—C$_5$H$_{12}$—CH$_3$, 3H). HR-MS (m/z): [M+H]$^+$ obsd.=242.1889 (calc.=242.1903).

N-octyl-1-aminomethylnaphthalene hydrochloride (3c): $^1$H NMR (CDCl$_3$) δ/ppm: 9.9 (s, Ar—CH$_2$—NH$_2$—C$_8$H$_{17}$, 2H), 8.12 (d, ArH, 1H), 7.85 (m, ArH, 3H), 7.64 (t, ArH, 1H), 7.51 (q, ArH, 2H), 4.5 (s, Ar—CH$_2$—NH$_2$—, 2H), 2.75 (t, —NH$_2$—CH$_2$—C$_5$H$_{11}$, 2H), 1.85 (q, —NH$_2$—CH$_2$—CH$_2$—C$_6$H$_{13}$, 2H), 1.3-1.1 (—NH$_2$—C$_2$H$_5$—(CH$_2$)$_5$—CH$_3$, 10H), 0.82 (t, —NH$_2$—C$_7$H$_{14}$—CH$_3$, 3H). HR-MS (m/z): [M+H]$^+$ obsd.=270.252 (calc.=270.2216).

N-decyl-1-aminomethylnaphthalene hydrochloride (3d): $^1$H NMR (CDCl$_3$) δ/ppm: 10 (s, Ar—CH$_2$—NH$_2$—C$_8$H$_{17}$, 2H), 8.12 (d, ArH, 1H), 7.85 (m, ArH, 3H), 7.64 (t, ArH, 1H), 7.51 (q, ArH, 2H), 4.5 (s, Ar—CH$_2$—NH$_2$—, 2H), 2.75 (t, —NH$_2$—CH$_2$—C$_5$H$_{11}$, 2H), 1.85 (q, —NH$_2$—CH$_2$—CH$_2$—C$_6$H$_{13}$, 2H), 1.3-1.1 (—NH$_2$—C$_2$H$_5$—(CH$_2$)$_5$—CH$_3$, 14H), 0.82 (t, —NH$_2$—C$_7$H$_{14}$—CH$_3$, 3H). HR-MS (m/z): [M+H]$^+$ obsd.=298.2541 (calc.=298.2535).

N-dodecyl-1-aminomethylnaphthalene hydrochloride (3e): $^1$H NMR (CDCl$_3$) δ/ppm: 10 (s, Ar—CH$_2$—NH$_2$—C$_8$H$_{17}$, 2H), 8.12 (d, ArH, 1H), 7.85 (m, ArH, 3H), 7.64 (t, ArH, 1H), 7.51 (q, ArH, 2H), 4.5 (s, Ar—CH$_2$—NH$_2$—, 2H), 2.75 (t, —NH$_2$—CH$_2$—C$_5$H$_{11}$, 2H), 1.85 (q, —NH$_2$—CH$_2$—CH$_2$—C$_6$H$_{13}$, 2H), 1.3-1.1 (—NH$_2$—C$_2$H$_5$—(CH$_2$)$_5$—CH$_3$, 18H), 0.82 (t, —NH$_2$—C$_7$H$_{14}$—CH$_3$, 3H). HR-MS (m/z): [M+H]$^+$ obsd.=326.2839 (calc.=326.2848).

Example 3.2

Synthesis of Boc-Lys(Boc)-N-butyl-1-Aminomethylnaphthalenes (compounds 3f-3j) as Furnished in FIG. 3

To a stirred solution containing about 0.42 g, 1.2 mmol of Boc-Lys(Boc)-OH in about 7 ml of 5:2 DMF/CHCl$_3$, about 522 μL (3 mmol) of N,N-Diisopropylethylamine (DIPEA) is added at a temperature of about 0° C. To this solution, about 0.46 g, 1.2 mmol of HBTU is added. The mixture is stirred for about 5 minutes at a temperature of about 0° C. and subsequently about 1 mmol of N-alkyl-1-Aminomethylnaphthalene hydrochloride is added to it. The mixture is again stirred at a temperature of about 0° C. for about 30 minutes and subsequently at room temperature for about 24 hrs. At the end of 24 hrs, CHCl$_3$ is evaporated under reduced pressure and the resulting solution is diluted to about 2 times its original volume by addition of ethyl acetate. This mixture is subsequently washed with 0.5 M KHSO$_4$, H$_2$O (×3) and brine. After passage through anhydrous Na$_2$SO$_4$, the volatile components are evaporated under reduced pressure and the residue is purified using column chromatography (only CHCl$_3$) to obtain Boc-Lys(Boc)-N-butyl-1-Aminomethylnaphthalenes with a yield of about 65% to about 90%. The purified compound is subsequently characterized using $^1$H NMR, IR and Mass spectrometry.

The characterized profile of Boc-Lys(Boc)-N-butyl-1-Aminomethylnaphthalenes is illustrated below:

Boc-Lys(Boc)-N-butyl-1-Aminomethylnaphthalene (3f): $^1$H NMR (CDCl$_3$) δ/ppm: 8.0-7.74 (ArH, 3H), 7.60-7.34 (ArH, 3H), 7.31-7.14 (ArH, 1H), 5.5-5.0 (Ar—CH$^1$H$^2$—N(R)Lys(boc)$_2$ and α-NH-Boc of Lys(boc)$_2$, 2H), 4.75-4.40 (Ar—CH$^1$H$^2$—N(R)Lys(boc)$_2$, Lys (ε-NH-Boc)-α-NH-boc and α-CHofLys(boc)$_2$, 3H), 3.40-3.0 (δ-CH$_2$ of Lys(boc)$_2$ and Ar—CH$_2$—N(—CH$_2$—C$_3$H$_7$)Lys(boc)$_2$, 4H), 1.72-1.12 (—CO—[CH—CH$_2$—CH$_2$—CH$_2$—NH—COO—C(CH$_3$)$_3$]-NH—COO—C(CH$_3$)$_3$ of Lys(boc)$_2$ and —CH$_2$—(CH$_2$)$_2$—CH$_3$ of R group, 28H), 0.84 (m, Ar—CH$_2$—N(—C$_3$H$_6$—CH$_3$)Lys(boc)$_2$, 3H). FT-IR (cm$^{-1}$): 3331 (carbamate N—H str.), 3085 (sp$^2$ C—H str.), 2975-2865 (sp$^3$ C—H str.), 1709 (C=O str. of carbamate), 1643 (C=O str. of tertiary amide), 1517-1450 (aromatic C=C str.). HR-MS (m/z): [M+H]$^+$ obsd.=542.3641 (calc.=542.3594).

Boc-Lys(Boc)-N-hexyl-1-Aminomethylnaphthalene (3g): $^1$H NMR (CDCl$_3$) δ/ppm: 8.0-7.74 (ArH, 3H), 7.60-7.34 (ArH, 3H), 7.31-7.14 (ArH, 1H), 5.5-5.0 (Ar—CH$^1$H$^2$—N(R)Lys(boc)$_2$ and α-NH-Boc of Lys(boc)$_2$, 2H), 4.75-4.40 (Ar—CH$^1$H$^2$—N(R)Lys(boc)$_2$, Lys (ε-NH-Boc)-α-NH-boc and α-CHofLys(boc)$_2$, 3H), 3.40-3.0 (δ-CH$_2$ of Lys(boc)$_2$ and Ar—CH$_2$—N(—CH$_2$—C$_5$H$_{11}$)Lys(boc)$_2$, 3H), 1.72-1.12 (—CO—[CH—CH$_2$—CH$_2$—CH$_2$—NH—COO—C(CH$_3$)$_3$]-NH—COO—C(CH$_3$)$_3$ of Lys(boc)$_2$ and —CH$_2$—(CH$_2$)$_4$—CH$_3$ of R group, 32H), 0.84 (m, Ar—CH$_2$—N(—C$_5$H$_{10}$—CH$_3$)Lys(boc)$_2$, 3H). FT-IR (cm$^{-1}$): 3331 (carbamate N—H str.), 3085 (sp$^2$ C—H str.), 2967-2867 (sp$^3$ C—H str.), 1709 (C=O str. of carbamate), 1643 (C=O str. of tertiary amide), 1517-1450 (aromatic C=C str.). HR-MS (m/z): [M+H]$^+$ obsd.=570.3954 (calc.=570.3907).

Boc-Lys(Boc)-N-octyl-1-Aminomethylnaphthalene (3h): $^1$H NMR (CDCl$_3$) δ/ppm: 8.0-7.74 (ArH, 3H), 7.60-7.34 (ArH, 3H), 7.31-7.14 (ArH, 1H), 5.5-5.0 (Ar—CH$^1$H$^2$—N(R)Lys(boc)$_2$ and α-NH-Boc of Lys(boc)$_2$, 2H), 4.75-4.40 (Ar—CH$^1$H$^2$—N(R)Lys(boc)$_2$, Lys (ε-NH-Boc)-α-NH-boc and α-CHofLys(boc)$_2$, 3H), 3.40-3.0 (δ-CH$_2$ of Lys(boc)$_2$ and Ar—CH$_2$—N(—CH$_2$—C$_5$H$_{11}$)Lys(boc)$_2$, 4H), 1.72-1.12 (—CO—[CH—CH$_2$—CH$_2$—CH$_2$—NH—COO—C(CH$_3$)$_3$]-NH—COO—C(CH$_3$)$_3$ of Lys(boc)$_2$ and —CH$_2$—(CH$_2$)$_6$—CH$_3$ of R group, 36H), 0.84 (m, Ar—CH$_2$—N(—C$_7$H$_{14}$—CH$_3$)Lys(boc)$_2$, 3H). FT-IR (cm$^{-1}$): 3331 (carbamate N—H str.), 3085 (sp$^2$ C—H str.), 2967-2867 (sp$^3$ C—H str.), 1709 (C=O str. of carbamate), 1640 (C=O str. of tertiary amide), 1517-1450 (aromatic C=C str.). HR-MS (m/z): [M+H]$^+$ obsd.=598.4246 (calc.=598.422)

Boc-Lys(Boc)-N-decyl-1-Aminomethylnaphthalene (3i): $^1$H NMR (CDCl$_3$) δ/ppm: 8.0-7.74 (ArH, 3H), 7.60-7.34 (ArH, 3H), 7.31-7.14 (ArH, 1H), 5.5-5.0 (Ar—CH$^1$H$^2$—N(R)Lys(boc)$_2$ and α-NH-Boc of Lys(boc)$_2$, 2H), 4.75-4.40 (Ar—CH$^1$H$^2$—N(R)Lys(boc)$_2$, Lys (ε-NH-Boc)-α-NH-boc and α-CHofLys(boc)$_2$, 3H), 3.40-3.0 (δ-CH$_2$ of Lys(boc)$_2$ and Ar—CH$_2$—N(—CH$_2$—C$_5$H$_{11}$)Lys(boc)$_2$, 4H), 1.72-1.12 (—CO—[CH$_2$—CH$_2$—CH$_2$—NH—COO—C(CH$_3$)$_3$]-NH—COO—C(CH$_3$)$_3$ of Lys(boc)$_2$ and —CH$_2$—(CH$_2$)$_6$—CH$_3$ of R group, 40H), 0.84 (m, Ar—CH$_2$—N(—C$_7$H$_{14}$—CH$_3$)Lys(boc)$_2$, 3H). FT-IR (cm$^{-1}$): 3331 (carbamate N—H str.), 3085 (sp$^2$ C—H str.), 2967-2867 (sp$^3$ C—H str.), 1709 (C=O str. of carbamate), 1640 (C=O str. of tertiary amide), 1517-1450 (aromatic C=C str.). HR-MS (m/z): [M+H]$^+$ obsd.=625.445 (calc.=625.4455).

Boc-Lys(Boc)-N-dodecyl-1-Aminomethylnaphthalene (3j): $^1$H NMR (CDCl$_3$) δ/ppm: 8.0-7.74 (ArH, 3H), 7.60-7.34 (ArH, 3H), 7.31-7.14 (ArH, 1H), 5.5-5.0 (Ar—CH$^1$H$^2$—N(R)Lys(boc)$_2$ and α-NH-Boc of Lys(boc)$_2$, 2H), 4.75-4.40 (Ar—CH$^1$H$^2$—N(R)Lys(boc)$_2$, Lys (ε-NH-Boc)-α-NH-boc and α-CHofLys(boc)$_2$, 3H), 3.40-3.0 (δ-CH$_2$ of Lys(boc)$_2$ and Ar—CH$_2$—N(—C H$_2$—C$_5$H$_{11}$)Lys(boc)$_2$, 4H), 1.72-1.12 (—CO—[CH—CH$_2$—CH$_2$—CH$_2$—CH$_2$—NH—COO—C(CH$_3$)$_3$]-NH—COO—C(CH$_3$)$_3$ of Lys(boc)$_2$ and —CH$_2$—(CH$_2$)$_6$—CH$_3$ of R group, 44H), 0.84 (m, Ar—CH$_2$—N(—C$_7$H$_{14}$—CH$_3$)Lys(boc)$_2$, 3H). FT-IR (cm$^{-1}$): 3331 (carbamate N—H str.), 3085 (sp$^2$ C—H str.), 2967-2867 (sp$^3$ C—H str.), 1709 (C=O str. of carbamate), 1640 (C=O str. of tertiary amide), 1517-1450 (aromatic C=C str.). HR-MS (m/z): [M+H]$^+$ obsd.=654.4842 (calc.=654.4846)

Example 3.3

Lys-N-alkyl-1-Aminomethylnaphthalene trifluoroacetates (compounds 3k-3o) as Furnished in FIG. 3

About 0.7 mmol Boc-Lys (Boc)-N-alkyl-1-Aminomethylnaphthalene compound is dissolved in about 5 ml of DCM and subsequently CF$_3$COOH (50% by volume) is added and stirred at room temperature. The reactions are monitored by TLC until complete removal of starting material. All the volatile components are removed by evaporation, and the product is purified by reverse phase HPLC using 0.1% Trifluoro acetic acid (TFA) in water and acetonitrile (0-100%) as mobile phase. C$_{18}$ column (10 mm diameter, 250 mm length) as stationary phase and UV detector at 270 nm wavelength is used. After drying the compounds in freeze drier, the compounds were characterized by $^1$H NMR, IR and mass spectrometry.

The characterized profile of Lys-N-alkyl-Aminomethylnaphthalene trifluoroacetate is illustrated below:

Lys-N-butyl-1-Aminomethylnaphthalene trifluoroacetate (3k, NCK-4):

$^1$H NMR (D$_2$O) δ/ppm: 8.14-7.76 (ArH, 3H) 7.75-7.19 (ArH, 4H), 5.59-5.0 (Ar—CH$^1$H$^2$—N(R)Lys, 2H), 4.5 (m, α-CHofLys, 1H) 3.67-3.0 (Ar—CH$_2$—N(CH$_2$(CH$_2$)$_2$CH$_3$)Lys, 2H), 2.84 (d, ε-CH$_2$ofLys, 2H), 2.04-1.10 (β-CH$_2$ofLys, γ-CH$_2$ofLys, δ-CH$_2$ofLysand Ar—CH$_2$—N(CH$_2$(CH$_2$)$_2$CH$_3$)Lys, 10H), 0.85 (m, Ar—CH$_2$—N(C$_3$H$_6$CH$_3$)Lys, 3H). FT-IR (cm$^{-1}$): 3414 (primary amine N—H str.), 3089 (sp$^2$ C—H str.), 2967-2867 (sp$^3$ C—H str.), 1678 (C=O str. of tertiary amide), 1517-1450 (aromatic C=C str.). HR-MS (m/z): [M+H]$^+$ obsd.=342.26'29 (calc.=342.2545).

Lys-N-hexyl-1-Aminomethylnaphthalene trifluoroacetate (3l, NCK-6):

$^1$H NMR (D$_2$O) δ/ppm: 7.87-7.5 (ArH, 2H) 7.5-7.0 (ArH, 5H), 5.14 (d, Ar—CH$^1$H$^2$—N(R)Lys, 1H), 4.48 (d, Ar—CH$^1$H$^2$—N(R)Lys, 1H) 4.37 (m, α-CHofLys, 1H), 3.21-2.7 (Ar—CH$_2$—N(CH$_2$(CH$_2$)$_2$CH$_3$)Lys and ε-CH$_2$ofLys, 4H), 1.94-1.19 (β-CH$_2$ofLys, γ-CH$_2$ofLys, δ-CH$_2$ofLysand Ar—CH$_2$—N(CH$_2$CH$_2$C$_3$H$_7$)Lys, 8H), 0.85 (m, Ar—CH$_2$—N(C$_2$H$_4$C$_3$H$_6$CH$_3$)Lys, 6H), 0.65 (m, Ar—CH$_2$—N(C$_5$H$_{10}$CH$_3$)Lys, 3H). FT-IR (cm$^{-1}$): 3414 (primary amine N—H str.), 3089 (sp$^2$ C—H str.), 2967-2867 (sp$^3$ C—H str.), 1678 (C=O str. of tertiary amide), 1517-1450 (aromatic C=C str.). HR-MS (m/z): [M+H]$^+$ obsd.=370.2849 (calc.=370.2858).

Lys-N-octyl-1-Aminomethylnaphthalene trifluoroacetate (3m, NCK-8):

$^1$H NMR (D$_2$O) δ/ppm: 7.71-7.5 (ArH, 2H) 7.44-6.91 (ArH, 5H), 5.0 (d, Ar—CH$^1$H$^2$—N(R)Lys, 1H), 4.4 (d, Ar—CH$^1$H$^2$—N(R)Lys, 1H) 4.29 (m, α-CHofLys, 1H), 3.18-2.59 (Ar—CH$_2$—N(CH$_2$(CH$_2$)$_2$CH$_3$)Lys and ε-CH$_2$ofLys, 4H), 1.87-1.60 (d, γ-CH$_2$ofLys, 2H), 1.60-1.02 (β-CH$_2$ofLys,δ-CH$_2$ofLysand Ar—CH$_2$—N(CH$_2$CH$_2$C$_6$H$_{13}$)Lys, 6H), 0.85 (m, Ar—CH$_2$—N(C$_2$H$_5$(CH$_2$)$_5$CH$_3$)Lys, 10H), 0.56 (m, Ar—CH$_2$—N(C$_7$H$_{14}$CH$_3$)Lys, 3H). FT-IR (cm$^{-1}$): 3414 (primary amine N—H str.), 3089 (sp$^2$ C—H str.), 2967-2867 (sp$^3$ C—H str.), 1678 (C=O str. of tertiary amide), 1517-1450 (aromatic C=C str.). HR-MS (m/z): [M+H]$^+$ obsd.=398.3228 (calc.=398.3171).

Lys-N-decyl-1-Aminomethylnaphthalene trifluoroacetate (3n, NCK-10):

$^1$H NMR (CD$_3$OD) δ/ppm: 8.2-7.8 (ArH, 3H) 7.7-7.3 (ArH, 4H), 5.6 (d, Ar—CH$^1$H$^2$—N(R)Lys, 1H), 4.7 (d, Ar—CH$^1$H$^2$—N(R)Lys, 1H) 4.4 (m, α-CHofLys, 1H), 3.6-2.59 (Ar—CH$_2$—N(CH$_2$(CH$_2$)$_2$CH$_3$)Lys and ε-CH$_2$ofLys, 4H), 2-1.8 (d, γ-CH$_2$ofLys, 2H), 1.70-1.4 (β-CH$_2$ofLys,δ—CH$_2$ofLysand Ar—CH$_2$—N(CH$_2$CH$_2$C$_6$H$_{13}$)Lys, 6H), 1.4-1.1 (m, Ar—CH$_2$—N(C$_2$H$_5$(CH$_2$)$_5$CH$_3$)Lys, 14H), 0.8 (m, Ar—CH$_2$—N(C$_7$H$_{14}$CH$_3$)Lys, 3H). FT-IR (cm$^{-1}$): 3414 (primary amine N—H str.), 3089 (sp$^2$ C—H str.), 2967-2867 (sp$^3$ C—H str.), 1678 (C=O str. of tertiary amide), 1517-1450 (aromatic C=C str.). HR-MS (m/z): [M+H]$^+$ obsd.=426.3458 (calc.=426.3484).

Lys-N-dodecyl-1-Aminomethylnaphthalene trifluoroacetate (3o, NCK-12):

$^1$H NMR (CD$_3$OD) δ/ppm: 8.2-7.8 (ArH, 3H) 7.7-7.3 (ArH, 4H), 5.6 (d, Ar—CH$^1$H$^2$—N(R)Lys, 1H), 4.7 (d, Ar—CH$^1$H$^2$—N(R)Lys, 1H) 4.4 (m, α-CHofLys, 1H), 3.6-2.59 (Ar—CH$_2$—N(CH$_2$(CH$_2$)$_2$CH$_3$)Lys and ε-CH$_2$ofLys, 4H), 2-1.8 (d, γ-CH$_2$ofLys, 2H), 1.70-1.4 (β-CH$_2$ofLys,δ-CH$_2$ofLysand Ar—CH$_2$—N(CH$_2$CH$_2$C$_6$H$_{13}$)Lys, 6H), 1.4-1.1 (m, Ar—CH$_2$—N(C$_2$H$_5$(CH$_2$)$_5$CH$_3$)Lys, 18H), 0.8 (m, Ar—CH$_2$—N(C$_7$H$_{14}$CH$_3$)Lys, 3H). FT-IR (cm$^{-1}$): 3414 (primary amine N—H str.), 3089 (sp$^2$ C—H str.), 2967-2867 (sp$^3$ C—H str.), 1678 (C=O str. of tertiary amide), 1517-1450 (aromatic C=C str.). HR-MS (m/z): [M+H]$^+$ obsd.=454.3793 (calc.=454.3797).

Example 4

Figure 4:
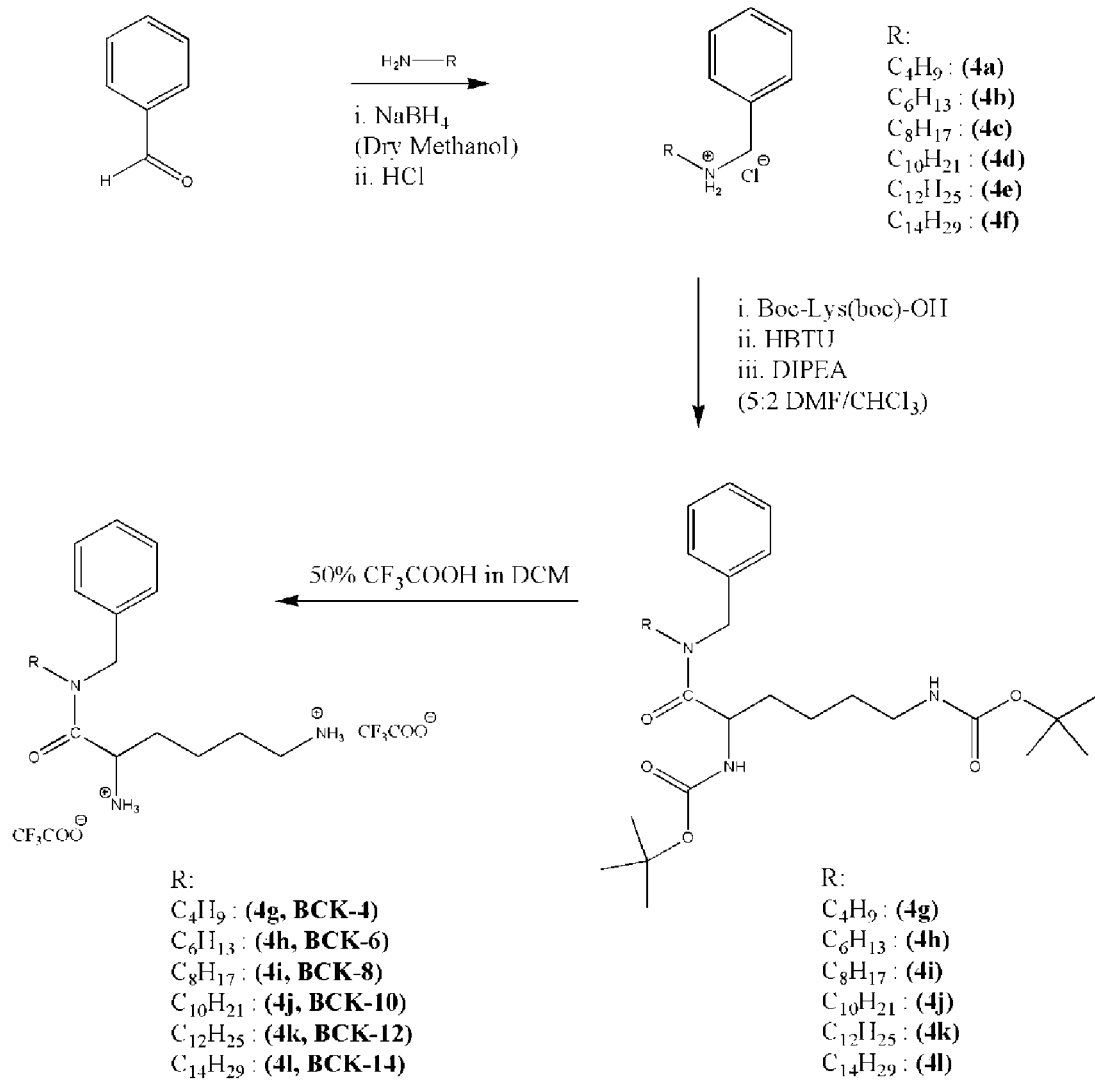
FIG. 4 represents the general synthetic scheme for the preparation of Benzene derivatives (BCK series).

Synthesis of BCK Compounds as Furnished in FIG. 4

Figure 6:
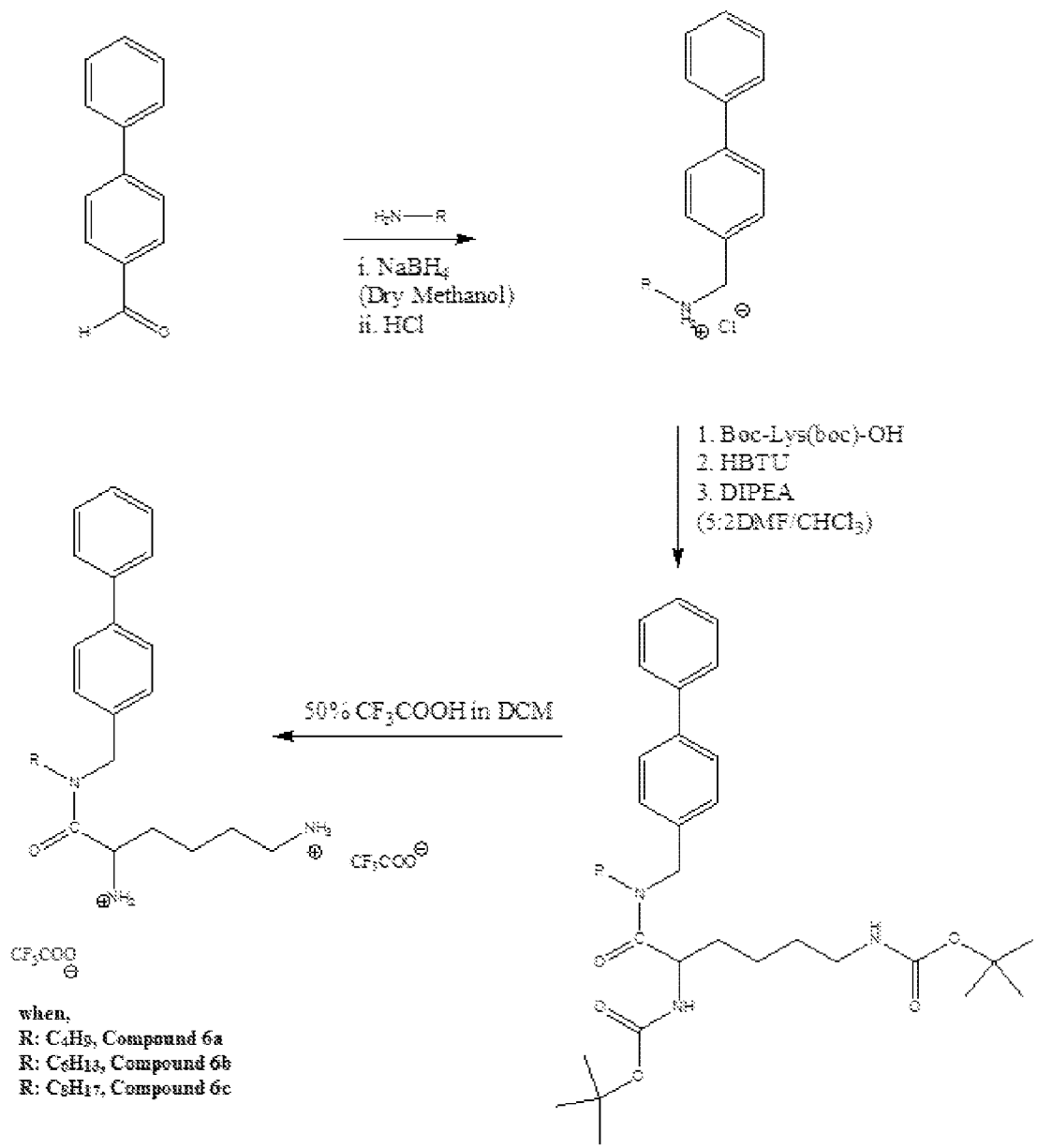
FIG. 6 represents the general synthetic scheme for the preparation of biphenyl derivatives.

The compounds represented in the BCK series follows a similar protocol of preparation as mentioned in the preparation of the ACK and NCK series (illustrated in FIG. 6). The only difference is that the starting aldehyde used to couple with alkylamines is Benzaldehyde.

Example 4.1

Synthesis of N-alkyl-1-Aminomethylbenzene hydrochlorides (compounds 4a-4f) as Furnished in FIG. 4

About 0.5 g, 4.7 mmol of Benzaldehyde and about 4.7 mmol of alkyl amines (4.7 mmol) are dissolved in about 10 ml 1:1 mixture of dry chloroform and methanol, and stirred at room-temperature (under Nitrogen atmosphere) for about 6 hrs. The resulting clear solution is then cooled to a temperature of about 0° C., and to it about 0.32 g (8.46 mmol) of Sodium borohydride is added. This solution is allowed to come to room temperature and stirred overnight. Then the solvents in the solution are evaporated under reduced pressure (not to dryness) and diluted with diethyl ether. To this about 20 ml of 2N NaOH is added and stirred for about 15 minutes. After separation from the NaOH layer, the organic layer is subsequently washed with water (×2), brine and dried over MgSO$_4$. The volatile components are then evaporated under reduced pressure and the residue is dissolved in minimum volume of methanol. To this, about 3 ml of 4N HCl is added and instantaneous formation of precipitate is observed. The volatile components are completely removed and the precipitate is dissolved in minimum volume of ethyl acetate (a few drops of methanol is added to dissolve the precipitate completely). To this, hexane is added to obtain pure crystals N-alkyl-1-Aminomethylbenzene hydrochlorides with a yield of about 75%. These crystals are filtered, dried and subsequently characterized using $^1$H NMR, IR and Mass spectrometry.

The characterized profile of N-alkyl-1-Aminomethylbenzene hydrochlorides is illustrated below:

N-butyl-1-aminomethylbenzene hydrochloride (4a): $^1$H NMR (CDCl$_3$) δ/ppm: 9.87 (s, Ar—CH$_2$—N$\underline{H}_2$—C$_4$H$_9$, 2H), 7.6 (d, Ar$\underline{H}$, 2H), 7.39 (m, Ar$\underline{H}$, 3H), 4.02 (s, Ar—C$\underline{H}_2$—NH$_2$—, 2H), 2.79 (t, —NH$_2$—C$\underline{H}_2$—C$_3$H$_7$, 2H), 1.82 (m, —NH$_2$—CH$_2$—C$\underline{H}_2$—C$_2$H$_5$, 2H), 1.4 (—NH$_2$—C$_2$H$_4$—C$\underline{H}_2$—CH$_3$, 2H), 0.82 (t, —NH$_2$—C$_3$H$_6$—C$\underline{H}_3$, 3H). HR-MS (m/z): [M+H]$^+$ obsd.=164.1430 (calc.=164.1439).

N-hexyl-1-aminomethylbenzene hydrochloride (4b): $^1$H NMR (CDCl$_3$) δ/ppm: 9.85 (s, Ar—CH$_2$—N$\underline{H}_2$—C$_6$H$_{13}$, 2H), 7.6 (d, Ar$\underline{H}$, 2H), 7.39 (m, Ar$\underline{H}$, 3H), 4.02 (s, Ar—C$\underline{H}_2$—NH$_2$—, 2H), 2.77 (t, —NH$_2$—C$\underline{H}_2$—C$_5$H$_{11}$, 2H), 1.84 (m, —NH$_2$—CH$_2$—C$\underline{H}_2$—C$_4$H$_9$, 2H), 1.25 (m, —NH$_2$—C$_2$H$_4$—(C$\underline{H}_2$)$_3$—CH$_3$, 6H), 0.84 (t, —NH$_2$—C$_5$H$_{10}$—C$\underline{H}_3$, 3H). HR-MS (m/z): [M+H]$^+$ obsd.=192.1777 (calc.=192.1747).

N-octyl-1-aminomethylbenzene hydrochloride (4c): $^1$H NMR (CDCl$_3$) δ/ppm: 9.87 (s, Ar—CH$_2$—N$\underline{H}_2$—C$_5$H$_3$, 2H), 7.6 (d, Ar$\underline{H}$, 2H), 7.39 (m, Ar$\underline{H}$, 3H), 4.02 (s, Ar—C$\underline{H}_2$—NH$_2$—, 2H), 2.77 (m, —NH$_2$—C$\underline{H}_2$—C$_7$H$_{15}$, 2H), 1.84 (m, —NH$_2$—CH$_2$—C$\underline{H}_2$—C$_6$H$_{13}$, 2H), 1.25 (m, —NH$_2$—C$_2$H$_5$—(C$\underline{H}_2$)$_5$—CH$_3$, 10H), 0.84 (t, —NH$_2$—C$_7$H$_{14}$—C$\underline{H}_3$, 3H). HR-MS (m/z): [M+H]$^+$ obsd.=220.2122 (calc.=220.206).

N-decyl-1-aminomethylbenzene hydrochloride (4d): $^1$H NMR (CDCl$_3$) δ/ppm: 9.87 (s, Ar—CH$_2$—N$\underline{H}_2$—C$_8$H$_{13}$, 2H), 7.6 (d, Ar$\underline{H}$, 2H), 7.39 (m, Ar$\underline{H}$, 3H), 4.02 (s, Ar—C$\underline{H}_2$—NH$_2$—, 2H), 2.77 (m, —NH$_2$—C$\underline{H}_2$—C$_7$H$_{15}$, 2H), 1.84 (m, —NH$_2$—CH$_2$—C$\underline{H}_2$—C$_6$H$_{13}$, 2H), 1.25 (m, —NH$_2$—C$_2$H$_5$—(C$\underline{H}_2$)$_5$—CH$_3$, 14H), 0.84 (t, —NH$_2$—C$_7$H$_{14}$—C$\underline{H}_3$, 3H). HR-MS (m/z): [M+H]$^+$ obsd.=247.2122 (calc.=247.23).

N-dodecyl-1-aminomethylbenzene hydrochloride (4e): $^1$H NMR (CDCl$_3$) δ/ppm: 9.87 (s, Ar—CH$_2$—N$\underline{H}_2$—C$_8$H$_{13}$, 2H), 7.6 (d, Ar$\underline{H}$, 2H), 7.39 (m, Ar$\underline{H}$, 3H), 4.02 (s, Ar—C$\underline{H}_2$—NH$_2$—, 2H), 2.77 (m, —NH$_2$—C$\underline{H}_2$—C$_7$H$_{15}$, 2H), 1.84 (m, —NH$_2$—CH$_2$—C$\underline{H}_2$—C$_6$H$_{13}$, 2H), 1.25 (m, —NH$_2$—C$_2$H$_5$—(C$\underline{H}_2$)$_5$—CH$_3$, 18H), 0.84 (t, —NH$_2$—C$_7$H$_{14}$—C$\underline{H}_3$, 3H). HR-MS (m/z): [M+H]$^+$ obsd.=276.2693 (calc.=276.2691).

N-tetradecyl-1-aminomethylbenzene hydrochloride (4f): $^1$H NMR (CDCl$_3$) δ/ppm: 9.87 (s, Ar—CH$_2$—N$\underline{H}_2$—C$_8$H$_{13}$, 2H), 7.6 (d, Ar$\underline{H}$, 2H), 7.39 (m, Ar$\underline{H}$, 3H), 4.02 (s, Ar—C$\underline{H}_2$—NH$_2$—, 2H), 2.77 (m, —NH$_2$—C$\underline{H}_2$—C$_7$H$_{15}$, 2H), 1.84 (m, —NH$_2$—CH$_2$—C$\underline{H}_2$—C$_6$H$_{13}$, 2H), 1.25 (m, —NH$_2$—C$_2$H$_5$—(C$\underline{H}_2$)$_5$—CH$_3$, 22H), 0.84 (t, —NH$_2$—C$_7$H$_{14}$—C$\underline{H}_3$, 3H). HR-MS (m/z): [M+H]$^+$ obsd.=304.3006 (calc.=304.3004).

Example 4.2

Synthesis of Boc-Lys(Boc)-N-alkyl-1-Aminomethylbenzenes (compounds 4g-4l) as Furnished in FIG. 4

To a stirred solution containing about 0.49 g, 1.4 mmol of Boc-Lys(Boc)-OH in about 8 ml of 6:2 DMF/CHCl$_3$, about 611 μL (3.51 mmol) of N,N-Diisopropylethylamine (DIPEA) is added at a temperature of about 0° C. To this solution about 0.53 g, 1.4 mmol of HBTU is added. This mixture is stirred for about 5 minutes at 0° C. and subsequently about 1.17 mmol of N-alkyl-1-Aminomethylbenzene hydrochloride is added. The mixture is stirred at a temperature of about 0° C. for about 30 minutes and subsequently at room temperature for about 24 hrs. At the end of 24 hrs, CHCl$_3$ is evaporated under reduced pressure and the resulting solution is diluted to 2 times its original volume by addition of ethyl acetate. This mixture is subsequently washed with 0.5 M KHSO$_4$, H$_2$O (×3) and brine. After passage through anhydrous Na$_2$SO$_4$, the volatile components are evaporated under reduced pressure and the residue is purified using column chromatography (only CHCl$_3$) to obtain Boc-Lys(Boc)-N-butyl-1-Aminomethylbenzenes with an yield of about 65% to about 97%. The purified compound is subsequently characterized using $^1$H NMR, IR and Mass spectrometry.

The characterized profile of Boc-Lys(Boc)-N-butyl-1-Aminomethylbenzenes is illustrated below:

Boc-Lys(Boc)-N-butyl-1-Aminomethylbenzene (4g): $^1$H NMR (CDCl$_3$) δ/ppm: δ 7.2 (Ar$\underline{H}$, 3H), 7.15 (d, Ar$\underline{H}$, 2H), 5.5 (m, Lys (ε-N$\underline{H}$-Boc)-α-N$\underline{H}$-boc, 1H), 4.97-4.56 (Ar—CH$^1\underline{H}^2$—N(R)Lys(boc)$_2$, and α-C$\underline{H}$ofLys(boc)$_2$, 3H), 4.44 (d, Ar—CH$^1\underline{H}^2$—N(R)Lys(boc)$_2$, 1H) 3.4-2.9 (δ-CH$_2$ of Lys(boc)$_2$ and Ar—CH$_2$—N(—C$\underline{H}_2$—C$_5$H$_{11}$)Lys(boc)$_2$, 4H), 1.8-1.2 (—CO—[CH—C$\underline{H}_2$—C$\underline{H}_2$—C$\underline{H}_2$—CH$_2$—NH—COO—C(C$\underline{H}_3$)$_3$]-NH—COO—C(C$\underline{H}_3$)$_3$ of Lys(boc)$_2$ and —CH$_2$—(C$\underline{H}_2$)$_2$—CH$_3$ of R group, 28H), 0.8 (m, Ar—CH$_2$—N(—C$_3$H$_6$—C$\underline{H}_3$)Lys(boc)$_2$, 3H). FT-IR (cm$^{-1}$): 3354 (carbamate N—H str.), 3085 (sp$^2$ C—H str.), 2967-2867 (sp$^3$ C—H str.), 1704 (C=O str. of carbamate), 1643 (C=O str. of tertiary amide), 1517-1450 (aromatic C=C str.). HR-MS (m/z): [M+H]$^+$ obsd.=492.3677 (calc.=492.3437).

Boc-Lys(Boc)-N-hexyl-1-Aminomethylbenzene (4h): $^1$H NMR (CDCl$_3$) δ/ppm: 7.2 (Ar$\underline{H}$, 3H), 7.15 (d, Ar$\underline{H}$, 2H), 5.5 (m, Lys (ε-N$\underline{H}$-Boc)-α-N$\underline{H}$-boc, 1H), 4.97-4.56 (Ar—CH$^1\underline{H}^2$—N(R)Lys(boc)$_2$ and α-C$\underline{H}$ofLys(boc)$_2$, 3H), 4.44 (d, Ar—CH$^1\underline{H}^2$—N(R)Lys(boc)$_2$, 1H) 3.4-2.9 (δ-C$\underline{H}_2$ of Lys (boc)$_2$ and Ar—CH$_2$—N(—C$\underline{H}_2$—C$_5$H$_{11}$)Lys(boc)$_2$, 4H), 1.8-1.2 (—CO—[CH—C$\underline{H}_2$—C$\underline{H}_2$—C$\underline{H}_2$—CH$_2$—NH—COO—C(C$\underline{H}_3$)$_3$]-NH—COO—C(C$\underline{H}_3$)$_3$ of Lys(boc)$_2$ and —CH$_2$—(C$\underline{H}_2$)$_4$—CH$_3$ of R group, 32H), 0.8 (m, Ar—CH$_2$—N(—C$_5$H$_{10}$—C$\underline{H}_3$)Lys(boc)$_2$, 3H). FT-IR (cm$^{-1}$): 3354 (carbamate N—H str.), 3085 (sp$^2$ C—H str.), 2967-2867 (sp$^3$ C—H str.), 1711 (C=O str. of carbamate), 1643 (C=O str. of tertiary amide), 1517-1450 (aromatic C=C str.). HR-MS (m/z): [M+H]$^+$ obsd.=520.387 (calc.=520.375)

Boc-Lys(Boc)-N-octyl-1-Aminomethylbenzene (4i): $^1$H NMR (CDCl$_3$) δ/ppm: 7.2 (Ar$\underline{H}$, 3H), 7.15 (d, Ar$\underline{H}$, 2H), 5.5 (m, Lys (ε-N$\underline{H}$-Boc)-α-N$\underline{H}$-boc, 1H), 4.97-4.56 (Ar—CH$^1\underline{H}^2$—N(R)Lys(boc)$_2$ and α-C$\underline{H}$ofLys(boc)$_2$, 3H), 4.44 (d, Ar—CH$^1\underline{H}^2$—N(R)Lys(boc)$_2$, 1H) 3.4-2.9 (δ-C$\underline{H}_2$ of Lys (boc)$_2$ and Ar—CH$_2$—N(—C$\underline{H}_2$—C$_5$H$_{11}$)Lys(boc)$_2$, 4H), 1.8-1.2 (—CO—[CH—C$\underline{H}_2$—C$\underline{H}_2$—C$\underline{H}_2$—CH$_2$—NH—COO—C(C$\underline{H}_3$)$_3$]-NH—COO—C(C$\underline{H}_3$)$_3$ of Lys(boc)$_2$ and —CH$_2$—(C$\underline{H}_2$)$_6$—CH$_3$ of R group, 36H), 0.8 (m, Ar—CH$_2$—N(—C$_7$H$_{14}$—C$\underline{H}_3$)Lys(boc)$_2$, 3H). FT-IR (cm$^{-1}$): 3354 (carbamate N—H str.), 3085 (sp$^2$ C—H str.), 2967-2867 (sp$^3$ C—H str.), 1704 (C=O str. of carbamate), 1643 (C=O str. of tertiary amide), 1517-1450 (aromatic C=C str.). HR-MS (m/z): [M+H]$^+$ obsd.=548.3842 (calc.=548.4063)

Boc-Lys(Boc)-N-decyl-1-Aminomethylbenzene (4j): $^1$H NMR (CDCl$_3$) δ/ppm: 7.2 (ArH, 3H), 7.15 (d, ArH, 2H), 5.5 (m, Lys (ε-NH-Boc)-α-NH-boc, 1H), 4.97-4.56 (Ar—CH$^1$H$^2$—N(R)Lys(boc)$_2$ and α-CHofLys(boc)$_2$, 3H), 4.44 (d, Ar—CH$^1$H$^2$—N(R)Lys(boc)$_2$, 1H) 3.4-2.9 (δ-CH$_2$ of Lys (boc)$_2$ and Ar—CH$_2$—N(—CH$_2$—C$_5$H$_{11}$)Lys(boc)$_2$, 4H), 1.8-1.2 (—CO—[CH—CH$_2$—CH$_2$—CH$_2$—CH$_2$—NH—COO—C(CH$_3$)$_3$]—NH—COO—C(CH$_3$)$_3$ of Lys(boc)$_2$ and —CH$_2$—(CH$_2$)$_6$—CH$_3$ of R group, 40H), 0.8 (m, Ar—CH$_2$—N(—C$_7$H$_{14}$—CH$_3$)Lys(boc)$_2$, 3H). FT-IR (cm$^{-1}$): 3354 (carbamate N—H str.), 3085 (sp$^2$ C—H str.), 2967-2867 (sp$^3$ C—H str.), 1704 (C=O str. of carbamate), 1643 (C=O str. of tertiary amide), 1517-1450 (aromatic C=C str.). HR-MS (m/z): [M+H]$^+$ obsd.=576.4376 (calc.=576.4376)

Boc-Lys(Boc)-N-dodecyl-1-Aminomethylbenzene (4k): $^1$H NMR (CDCl$_3$) δ/ppm: 7.2 (ArH, 3H), 7.15 (d, ArH, 2H), 5.5 (m, Lys (ε-NH-Boc)-α-NH-boc, 1H), 4.97-4.56 (Ar—CH$^1$H$^2$—N(R)Lys(boc)$_2$ and α-CHofLys(boc)$_2$, 3H), 4.44 (d, Ar—CH$^1$H$^2$—N(R)Lys(boc)$_2$, 1H) 3.4-2.9 (δ-CH$_2$ of Lys(boc)$_2$ and Ar—CH$_2$—N(—CH$_2$—C$_5$H$_{11}$)Lys(boc)$_2$, 4H), 1.8-1.2 (—CO—[CH—CH$_2$—CH$_2$—CH$_2$—CH$_2$—NH—COO—C(CH$_3$)$_3$]-NH—COO—C(CH$_3$)$_3$ of Lys(boc)$_2$ and —CH$_2$—(CH$_2$)$_6$—CH$_3$ of R group, 44H), 0.8 (m, Ar—CH$_2$—N(—C$_7$H$_{14}$—CH$_3$)Lys(boc)$_2$, 3H). FT-IR (cm$^{-1}$): 3354 (carbamate N—H str.), 3085 (sp$^2$ C—H str.), 2967-2867 (sp$^4$ C—H str.), 1704 (C=O str. of carbamate), 1643 (C=O str. of tertiary amide), 1517-1450 (aromatic C=C str.). HR-MS (m/z): [M+H]$^+$ obsd.=604.4678 (calc.=604.4689)

Boc-Lys(Boc)-N-tetradecyl-1-Aminomethylbenzene (4l): $^1$H NMR (CDCl$_3$) δ/ppm: 7.2 (ArH, 3H), 7.15 (d, ArH, 2H), 5.5 (m, Lys (ε-NH-Boc)-α-NH-boc, 1H), 4.97-4.56 (Ar—CH$^1$H$^2$—N(R)Lys(boc)$_2$ and α-CHofLys(boc)$_2$, 3H), 4.44 (d, Ar—CH$^1$H$^2$—N(R)Lys(boc)$_2$, 1H) 3.4-2.9 (δ-CH$_2$ of Lys(boc)$_2$ and Ar—CH$_2$—N(—CH$_2$—C$_5$H$_{11}$)Lys(boc)$_2$, 4H), 1.8-1.2 (—CO—[CH—CH$_2$—CH$_2$—CH$_2$—CH$_2$—NH—COO—C(CH$_3$)$_3$]-NH—COO—C(CH$_3$)$_3$ of Lys(boc)$_2$ and —CH$_2$—(CH$_2$)$_6$—CH$_3$ of R group, 48H), 0.8 (m, Ar—CH$_2$—N(—C$_7$H$_{14}$—CH$_3$)Lys(boc)$_2$, 3H). FT-IR (cm$^{-1}$): 3354 (carbamate N—H str.), 3085 (sp$^2$ C—H str.), 2967-2867 (sp$^3$ C—H str.), 1704 (C=O str. of carbamate), 1643 (C=O str. of tertiary amide), 1517-1450 (aromatic C=C str.). HR-MS (m/z): [M+H]$^+$ obsd.=632.5005 (calc.=632.5002)

Example 4.3

Synthesis of Lys-N-alkyl-1-Aminomethylbenzene trifluoroacetates (compounds 4m-4r) as Furnished in FIG. 4

About 0.7 mmol of Boc-Lys(Boc)-N-alkyl-1-Aminomethylbenzene compound is dissolved in about 5 ml DCM and subsequently CF$_3$COOH (50% by volume) is added and stirred at room temperature. The reactions are monitored by TLC until complete removal of starting material. All the volatile components are removed, and the product is purified by reverse phase HPLC using 0.1% Trifluoroacetic acid (TFA) in water and acetonitrile (0-100%) as mobile phase. C$_{18}$ column (10 mm diameter, 250 mm length) as stationary phase and UV detector at 270 nm wavelength is used. After drying the compounds in freeze drier, the compounds are characterized by $^1$H NMR, IR and mass spectrometry.

The characterized profile of Lys-N-alkyl-1-Aminomethylbenzene trifluoroacetate is illustrated below:

Lys-N-butyl-1-Aminomethylbenzene trifluoroacetate (4m, BCK-4):
$^1$H-NMR (D$_2$O) δ/ppm: 7.36-7.09 (ArH, 5H) 4.63 (t, 1H), 4.53-4.29 (2H), 3.36-3.08 (Ar—CH$_2$—N(CH$_2$(CH$_2$)$_2$(CH$_3$)Lys, 2H), 2.94-2.87 ((m, ε-CH$_2$ofLys, 2H), 1.90-1.3 (β-CH$_2$ofLys, γ-CH$_2$ofLys, δ-CH$_2$ofLysand Ar—CH$_2$—N(CH$_2$CH$_2$C$_2$H$_5$)Lys, 8H), 1.10 (m, Ar—CH$_2$—N(C$_2$H$_4$CH$_2$CH$_3$)Lys, 2H), 0.72 (t, Ar—CH$_2$—N(C$_3$H$_6$CH$_3$)Lys, 3H). FT-IR (cm$^{-1}$): 3414 (primary amine N—H str), 3089 (sp$^2$ C—H str.), 2967-2867 (sp$^3$ C—H str.), 1678 (C=O str. of tertiary amide), 1517-1450 (aromatic C=C str.). HR-MS (m/z): [M+H]$^+$ obsd.=292.2369 (calc.=292.2389).

Lys-N-hexyl-1-Aminomethylbenzene trifluoroacetate (4n, BCK-6):
$^1$H-NMR (D$_2$O) δ/ppm: 7.36-7.09 (ArH, 5H) 4.63 (t, 1H), 4.53-4.29 (2H), 3.36-3.08 (Ar—CH$_2$—N(CH$_2$(CH$_2$)$_2$CH$_3$)Lys, 2H), 2.94-2.87 (m, ε-CH$_2$ofLys, 2H), 1.90-1.3 (β-CH$_2$ofLys, γ-CH$_2$ofLys, δ-CH$_2$ofLysand Ar—CH$_2$—N(CH$_2$CH$_2$C$_4$H$_9$)Lys, 8H), 1.10 (d, Ar—CH$_2$—N(C$_2$H$_4$(CH$_2$)$_3$CH$_3$)Lys, 6H), 0.72 (t, Ar—CH$_2$—N(C$_5$H$_{10}$CH$_3$)Lys, 3H). FT-IR (cm$^{-1}$): 3414 (primary amine N—H str.), 3089 (sp$^2$ C—H str.), 2967-2867 (sp$^3$ C—H str.), 1678 (C=O str. of tertiary amide), 1517-1450 (aromatic C=C str.). HR-MS (m/z): [M+H]$^+$ obsd.=320.2732 (calc.=320.2702).

Lys-N-octyl-1-Aminomethylbenzene trifluoroacetates (4o, BCK-8):
$^1$H-NMR (D$_2$O) δ/ppm: 7.36-7.09 (ArH, 5H) 4.8 (d, 1H), 4.6 (d, 1H) 4.53-4.3 (2H), 3.36-3.08 (Ar—CH$_2$—N(CH$_2$(CH$_2$)$_2$CH$_3$)Lys, 2H), 2.94-2.87 ((m, ε-CH$_2$ofLys, 2H), 2.1-1.3 (β-CH$_2$ofLys, γ-CH$_2$ofLys, δ-CH$_2$ofLysand Ar—CH$_2$—N(CH$_2$CH$_2$C$_6$H$_{13}$)Lys, 8H), 1.36-0.97 (Ar—CH$_2$—N(C$_2$H$_4$(CH$_2$)$_5$H$_3$)Lys, 10H), 0.84 (t, Ar—CH$_2$—N(C$_7$H$_{14}$CH$_3$)Lys, 3H). FT-IR (cm$^{-1}$): 3414 (primary amine N—H str.), 3089 (sp$^2$ C—H str.), 2967-2867 (sp$^3$ C—H str.), 1678 (C=O str. of tertiary amide), 1517-1450 (aromatic C=C str.). HR-MS (m/z): [M+H]$^+$ obsd.=348.3016 (calc.=348.3015).

Lys-N-decyl-1-Aminomethylbenzene trifluoroacetates (4p, BCK-10):
$^1$H-NMR (CD$_3$OD) δ/ppm: 7.5-7.2 (ArH, 5H) 4.8 (t, Ar—CH$^1$H$^2$—N(R)Lys, 1H), 4.6 (d, Ar—CH$^1$H$^2$—N(R)Lys, 1H) 4.4 (m, α-CHofLys, 1H) 1H), 3.6-3.2 (Ar—CH$_2$—N(CH$_2$(CH$_2$)$_2$R)Lys, 2H), 2.94-2.87 ((m, ε-CH$_2$ofLys, 2H), 2.0-1.4 (β-CH$_2$ofLys, γ-CH$_2$ofLys, δ-CH$_2$ofLysand Ar—CH$_2$—N(CH$_2$CH$_2$C$_6$H$_{13}$)Lys, 8H), 1.4-1.2 (Ar—CH$_2$—N(C$_2$H$_4$(CH$_2$)$_5$CH$_3$)Lys, 14H), 0.84 (t, Ar—CH$_2$—N(C$_7$H$_{14}$CH$_3$)Lys, 3H). FT-IR (cm$^{-1}$): 3414 (primary amine N—H str.), 3089 (sp$^2$ C—H str.), 2967-2867 (sp$^3$ C—H str.), 1678 (C=O str. of tertiary amide), 1517-1450 (aromatic C=C str.). HR-MS (m/z): [M+H]$^+$ obsd.=376.3317 (calc.=376.3328).

Lys-N-dodecyl-1-Aminomethylbenzene trifluoroacetates (4q, BCK-12):
$^1$H-NMR (CD$_3$OD) δ/ppm: 7.5-7.2 (ArH, 5H) 4.8 (t, Ar—CH$^1$H$^2$—N(R)Lys, 1H), 4.6 (d, Ar—CH$^1$H$^2$—N(R)Lys, 1H) 4.4 (m, α-CHofLys, 1H) 1H), 3.6-3.2 (Ar—CH$_2$—N(CH$_2$(CH$_2$)$_2$R)Lys, 2H), 2.94-2.87 ((m, ε-CH$_2$ofLys, 2H), 2.0-1.4 (β-CH$_2$ofLys, γ-CH$_2$ofLys, δ-CH$_2$ofLysand Ar—CH$_2$—N(CH$_2$CH$_2$C$_6$H$_{13}$)Lys, 8H), 1.4-1.2 (Ar—CH$_2$—N(C$_2$H$_4$(CH$_2$)$_5$CH$_3$)Lys, 18H), 0.84 (t, Ar—CH$_2$—N(C$_7$H$_{14}$CH$_3$)Lys, 3H). FT-IR (cm$^{-1}$): 3414 (primary amine N—H str.), 3089 (sp$^2$ C—H str.), 2967-2867 (sp$^3$ C—H str.), 1678 (C=O str. of tertiary amide), 1517-1450 (aromatic C=C str.). HR-MS (m/z): [M+H]$^+$ obsd.=404.3628 (calc.=404.3641).

Lys-N-tetradecyl-1-Aminomethylbenzene trifluoroacetates (4r, BCK-14):

$^1$H-NMR (CD$_3$OD) δ/ppm: 7.36-7.09 (Ar$\underline{H}$, 5H) 4.6 (t, 1H), 4.53-4.3 (2H), 3.36-3.08 (Ar—CH$_2$—N(C$\underline{H}_2$(CH$_2$)$_2$CH$_3$)Lys, 2H), 2.94-2.87 ((m, ε-C$\underline{H}_2$ofLys, 2H), 2.1-1.3 (β-C$\underline{H}_2$ofLys, γ-C$\underline{H}_2$ofLys, δ-C$\underline{H}_2$ofLysand Ar—CH$_2$—N(CH$_2$C$\underline{H}_2$C$_6$H$_{13}$)Lys, 8H), 1.36-0.97 (Ar—CH$_2$—N(C$_2$H$_4$(C$\underline{H}_2$)$_5$CH$_3$)Lys, 22H), 0.84 (t, Ar—CH$_2$—N(C$_7$H$_{14}$C$\underline{H}_3$)Lys, 3H). FT-IR (cm$^{-1}$): 3414 (primary amine N—H str.), 3089 (sp$^2$ C—H str.), 2967-2867 (sp$^3$ C—H str.), 1678 (C=O str. of tertiary amide), 1517-1450 (aromatic C=C str.). HR-MS (m/z): [M+H]$^+$ obsd.=432.3954 (calc.=432.3954).

Example 5.1

Synthesis of N-octyldecan-1-aminium chloride (5b) as Furnished in FIG. 5

About 0.5 g, 3.87 mmol of Octylamine and about 0.73 g, 4.65 mmol of decanal are dissolved in about 20 ml of dry methanol and stirred at room-temperature (under Nitrogen atmosphere) for about 6 hrs. The resulting clear solution is then cooled to a temperature of about 0° C., and to this about 0.3 g, 7.74 mmol of sodium borohydride is added. This is allowed to come to room temperature and stirred overnight. Then the solvents are evaporated under reduced pressure (not to dryness) and diluted with diethyl ether. To this about 20 ml 2N NaOH is added and stirred for about 15 minutes. After separation from the NaOH layer, the organic layer is subsequently washed with water (twice), brine and dried over MgSO$_4$. The organic layer is then evaporated under reduced pressure and the residue is dissolved in 2 mL methanol. To this about 3 ml of 4N HCl is added and instantaneous formation of precipitate is observed. The solvents are completely removed and the precipitate is dissolved in 4 mL minimum volume of ethyl acetate (a few drops of methanol is added to dissolve completely). To this hexane is added to obtain pure crystals of N-octyldecan-1-aminium chloride with a yield of about 62%). These crystals are filtered, dried and subsequently characterized using $^1$H NMR.

$^1$H NMR (CDCl$_3$) δ/ppm: 9.5 (s, C$_8$H$_{17}$—N$\underline{H}_2$—C$_{10}$H$_{21}$, 2H), 3.0 (m, R'CH$_2$—NH$_2$—C$\underline{H}_2$—R, 4H), 1.84 (m, R'—CH$_2$—C$\underline{H}_2$—NH$_2$—CH$_2$—C$\underline{H}_2$—R, 4H), 1.4-1.1 (s, R'—CH$_2$—CH$_2$—NH$_2$—CH$_2$—CH$_2$—R, 24H), 0.84 (t, CH$_3$—R'—NH$_2$—R—C$\underline{H}_3$, 6H).

Example 5.2

Synthesis of Boc-Lys(Boc)-N-octylaminodecane (5c) as Furnished in FIG. 5

To about 0.68 g, 1.4 mmol of Boc-Lys(Boc)-OH in 6:3 DMF/CHCl$_3$ (9 mL), about 860 μL, 4.92 mmol N,N-Diisopropylethylamine (DIPEA) ( ) is added at temperature of about 0° C. To this solution is added about 0.75 g, 1.97 mmol HBTU ( ). This reaction mixture is stirred for about 5 minutes at temperature of about 0° C. and subsequently 0.5 g, 1.64 mmol N-octyldecan-1-aminium chloride ( ) is added. The mixture is stirred at a temperature of about 0° C. for about 30 minutes and subsequently at RT for about 24 hrs. At the end, CHCl$_3$ is evaporated under reduced pressure and the resulting solution is diluted to 2 times its original volume by addition of ethyl acetate. This mixture is subsequently washed with about 0.5 M KHSO$_4$, H$_2$O (thrice) and brine. After passage through anhydrous Na$_2$SO$_4$, the organic layer is evaporated under reduced pressure and the residue is purified using column chromatography (only CHCl$_3$) to obtain Boc-Lys(Boc)-N-octylaminodecane with a yield of about 72%. The purified compound is subsequently characterized using $^1$H NMR, IR and Mass spectrometry.

$^1$H NMR (CDCl$_3$) δ/ppm: 5.4 (m, Lys (ε-N$\underline{H}$-Boc)-α-N$\underline{H}$-boc, 1H), 4.7-4.5 (Lys (ε-N$\underline{H}$-Boc)-α-N$\underline{H}$-boc, and α-C$\underline{H}$ofLys(boc)$_2$, 2H), 3.5-3 (δ-CH$_2$ of Lys(boc)$_2$ and R'—CH$_2$—N(—C$\underline{H}_2$—R)Lys(boc)$_2$, 6H), 1.7-1.2 (—CO—[CH—C$\underline{H}_2$—C$\underline{H}_2$—C$\underline{H}_2$—CH$_2$—NH—COO—C(C$\underline{H}_3$)$_3$]-NH—COO—C(C$\underline{H}_3$)$_3$ of Lys(boc)$_2$ and —CH$_2$—(C$\underline{H}_2$)$_6$—CH$_3$ of R group and —CH$_2$—(C$\underline{H}_2$)$_8$—CH$_3$, of R' group, 52H), 0.8 (the terminal CH$_3$ of alkyl chains, 6H). FT-IR (cm$^{-1}$): 3437 (carbamate N—H str.), 2928-2863 (sp$^3$ C—H str.), 1670 (C=O str. of carbamate), 1523 (C=O str. of tertiary amide). HR-MS (m/z): [M+H]$^+$ obsd.=398.4089 (calc.=398.411)

Example 5.3

Synthesis of Lys-N-octylaminodecane (5d, Dec-CK-8) as Furnished in FIG. 5

Boc-Lys(Boc)-N-octylaminodecane is dissolved in DCM and subsequently CF$_3$COOH (50% by volume) is added and stirred at RT. The reactions are monitored by TLC until complete removal of starting material. All the volatile components are removed and the compound is dried overnight in a high vacuum oven. Then the compound is characterized by $^1$H NMR, IR and mass spectrometry.

$^1$H-NMR (CD$_3$OD) δ/ppm: 4.3 (α-C$\underline{H}_2$ofLys, 1H), 3.7-2.8 (6-CH$_2$ of Lys and R'—CH$_2$—N(—C$\underline{H}_2$—R)Lys, 6H), 1.9-1.2 β-C$\underline{H}_2$ofLys, γ-C$\underline{H}_2$ofLys, δ-C$\underline{H}_2$ofLys and —CH$_2$—(C$\underline{H}_2$)$_6$—CH$_3$ of R group and —CH$_2$—(C$\underline{H}_2$)$_8$—CH$_3$, of R' group, 34H), 0.8 (the terminal CH$_3$ of alkyl chains, 6H). FT-IR (cm$^{-1}$): 3350 (carbamate N—H str.), 2912-2847 (sp$^3$ C—H str.), 1702 (C=O str. of carbamate), 1630 (C=O str. of tertiary amide). HR-MS (m/z): [M+H]$^+$ obsd.=598.5152 (calc.=598.5159).

Example: 6.1

Synthesis of compound N-alkyl-Aminomethyl biphenyl hydrochlorides) as Furnished in FIG. 6

About 0.5 g (2.74 mmole) of biphenylcarboxaldehyde and about 2.74 mmole of alkyl amine are dissolved in about 10 ml of dry methanol. This mixture is stirred at RT for about 6 hours. The resulting clear solution is then cooled to a temperature of about 0° C. To this about 0.183 g (4.93 mmole) Sodium borohydride, about is added and stirred for about 12 hours. Solvent is evaporated under reduced pressure. About 20 mL of Diethyl ether and about 10 mL of 2N NaOH are then added and stirred for about 15 min. After separation from the NaOH layer, the organic layer is subsequently washed with water. The volatiles are then evaporated under reduced pressure. To this about 3 ml of 4N HCl is added and instantaneous formation of precipitate is observed. The volatiles components are completely removed and the precipitate is dissolved in 4 ml of ethyl acetate (a few drops of methanol are added to dissolve completely). Hexane is added to obtain pure crystals of N-alkyl-Aminomethyl biphenyl hydrochlorides) with an yield of about 75%. These crystals are filtered, dried and subsequently characterized using $^1$H NMR.

N-butyl-1-aminomethylbiphenyl hydrochloride (5a): $^1$H NMR (CDCl$_3$) δ/PPM 9 (s, 2H), 7.4-7.6 (9H), 4 (s, 2H), 2.8 (d, 2H), 1.9 (m, 2H), 1.4 (q, 2H), 0.9 (t, 3H).

N-hexyl-1-aminomethylbiphenyl hydrochloride (5b): $^1$H NMR (CDCl$_3$) δ/PPM 9 (s, 2H), 7.4-7.6 (9H), 4 (s, 2H), 2.8 (d, 2H), 1.9 (m, 2H), 1.4 (q, 6H), 0.9 (t, 3H). IR (cm$^{-1}$)

N-Octyl-1-aminomethylbiphenyl hydrochloride (5c): $^1$H NMR (CDCl$_3$) δ/PPM 9 (s, 2H), 7.4-7.6 (9H), 4 (s, 2H), 2.8 (d, 2H), 1.9 (m, 2H), 1.4 (q, 10H), 0.9 (t, 3H). IR (cm$^{-1}$)

Example 6.2

Synthesis of Boc-Lys(Boc)-N-alkyl-1-Aminomethylbiphenyls as Furnished in FIG. 6

About 0.29 g of Boc-Lys-(Boc)OH (0.7 mmole) is dissolved in about 7 ml of 2:5 CHCl$_3$/DMF. About 342 ul of DIPEA (2.1 mmole) and about 0.32 g of HBTU (0.8 mmole) are added. This mixture is stirred for about 5 minutes at temperature of about 0° C. and about 0.214 g (1 eqv) of secondary amines of Biphenyls is added. This mixture is stirred at room temperature for about 18 hrs. Chloroform and DMF are evaporated under reduced pressure. About 60 ml of ethyl acetate is dissolved and washed with KHSO$_4$. This compound is again washed with saturated Na$_2$CO$_3$ and subsequently dried by passing through Na$_2$SO$_4$. Ethyl acetate is evaporated under reduced pressure. The final compound is purified using column chromatography to obtain a yield about 68% to about 90%. The purified Boc-Lys(Boc)-N-alkyl-1-Aminomethylbiphenyls are subsequently characterized using $^1$H NMR.

Boc-Lys(Boc)-N-Butyl-1-Aminomethylbiphenyl
$^1$H NMR (CDCl$_3$) δ/PPM 7.4-7.6 (9H), 5.4 (D, 1H), 4.8 (t, 1H), 4.2 (s, 2H), 3.3 (q, 2H), 3 (q, 2H), 1.2-1.9 (m, 29H), 0.9 (t, 3H)

Boc-Lys(Boc)-N-hexyl-1-Aminomethylbiphenyl
$^1$H NMR (CDCl$_3$) δ/PPM 7.4-7.6 (9H), 5.4 (D, 1H), 4.8 (t, 1H), 4.2 (s, 2H), 3.3 (q, 2H), 3 (q, 2H), 1.2-1.9 (m, 33H), 0.9 (t, 3H)

Boc-Lys(Boc)-N-octyl-1-Aminomethylbiphenyl
$^1$H NMR (CDCl$_3$) δ/PPM 7.4-7.6 (9H), 5.4 (D, 1H), 4.8 (t, 1H), 4.2 (s, 2H), 3.3 (d, 2H), 3 (q, 2H), 1.2-1.9 (m, 37H), 0.9 (t, 3H)

Example 6.3

Synthesis of Lys-N-alkylaminomethylbiphenyl as Furnished in FIG. 6

Boc-Lys(Boc)-N-alkylaminomethylbiphenyl is dissolved in DCM and subsequently CF$_3$COOH (about 50% by volume) is added and stirred at RT. The reactions are monitored by TLC until complete removal of starting material. All the volatile components are removed and the compound is dried overnight in a high vacuum oven. Then the compound is characterized by $^1$H NMR.

Lys-N-Butyl-1-Aminomethylbiphenyl (Compound 6a)
$^1$H NMR (D$_2$O) δ/PPM 7.4-6.7 (9H), 4.5-4 (4H), 3.1-2.6 (4H), 2-0.7 (14H), 0.6 (t, 3H)

Lys-N-hexyl-1-Aminomethylbiphenyl (Compound 6b)
$^1$H NMR (D$_2$O) δ/PPM 7.4-6.7 (9H), 4.5-4 (4H), 3.1-2.6 (4H), 2-0.7 (18H), 0.6 (t, 3H)

Lys-N-octyl-1-Aminomethylbiphenyl (Compound 6c)
$^1$H NMR (D$_2$O) δ/PPM 7.4-6.7 (9H), 4.5-4 (4H), 3.1-2.6 (4H), 2-0.7 (22H), 0.6 (t, 3H)

Example: 7.1

Figure 7:
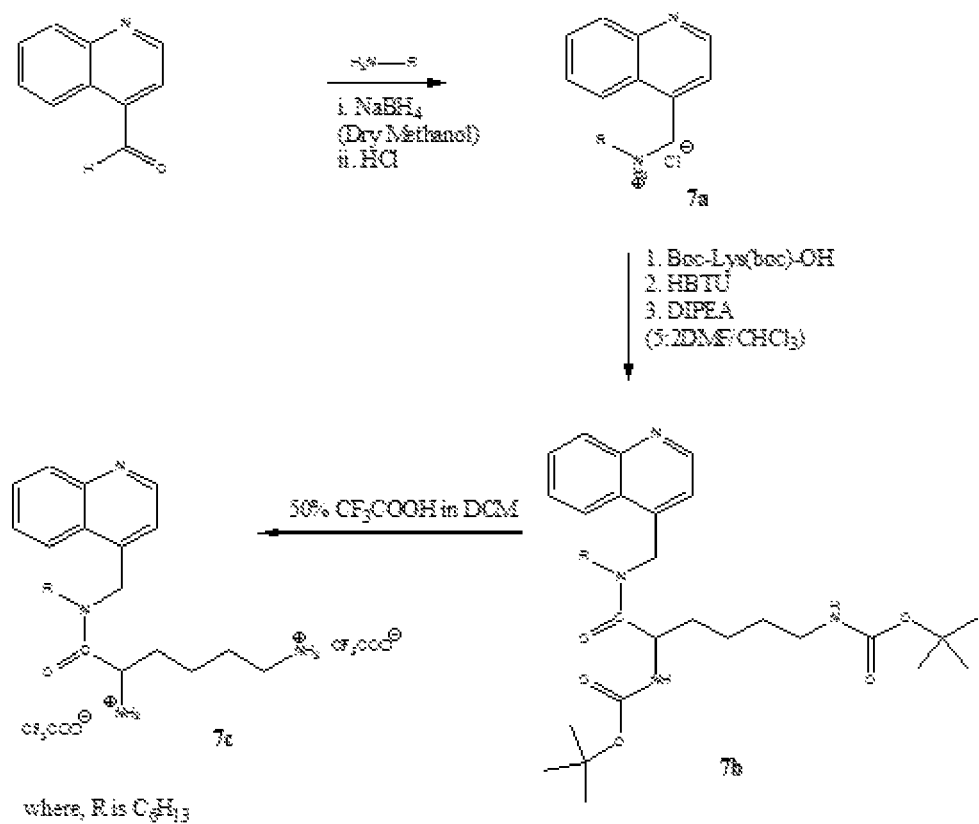
FIG. 7 represents the general synthetic scheme for the preparation of quinoline derivative.

Synthesis of compound N-(quinolin-4-ylmethyl)hexan-1-amine hydrochlorides (Compound 7a) as Furnished in FIG. 7

About 0.2 g (1.27 mmole) of 4-Quinolincarboxaldehyde and about 1.27 mmole of alkyl amine are dissolved in about 10 ml of dry methanol. This mixture is stirred at RT for about 12 hrs. The resulting clear solution is then cooled to a temperature of about 0° C. To this about 0.068 g (1.8 mmol) sodium borohydride, is added and stirred for about 12 hours. Solvent is evaporated under reduced pressure. About 20 mL of Diethyl ether and about 10 mL of 2N NaOH are added and stirred for about 15 min. After separation from the NaOH layer, the organic layer is subsequently washed with water. The volatiles are then evaporated under reduced pressure. To this about 3 ml of 4N HCl is added and instantaneous formation of precipitate is observed. The volatile components are completely removed and the precipitate is dissolved in 4 ml of ethyl acetate (4 drops of methanol are added to dissolve completely). Hexane is added to obtain pure crystals of the N-alkyl-4-Aminomethylquinolinyl hydrochloride with an yield of about 70%. The crystals are filtered, dried and subsequently characterized using $^1$H NMR.

N-(quinolin-4-ylmethyl)hexan-1-amine hydrochloride: $^1$H NMR (D$_2$O) δ/PPM 9.2 (1H), 8.4-8 (5H), 5.1 (2H), 3.3 (2H), 1.8 (2H), 1.5-1.3 (6H), 0.9 (3H)

Example 7.2

Synthesis of Boc-Lys(Boc)-N-(quinolin-4-ylmethyl) hexan-1-amine (Compound 7b) as Furnished in FIG. 7

About 0.33 g of Boc-Lys-(Boc)OH (0.79 mmol) is dissolved in about 11 ml of 2:9 CHCl$_3$/DMF. To this solution, about 420 µl of DIPEA (2.3 mmol) and about 0.36 g of HBTU (0.9 mmol) are added. This mixture is stirred for about 5 minutes at temperature of about 0° C. and about 0.25 g (0.79 mmol, 1 eqv) of secondary amines of Biphenyls is added. This mixture is stirred at room temperature for about 18 hrs. Chloroform and DMF are evaporated under reduced pressure. About 60 ml of ethyl acetate is dissolved and washed with KHSO$_4$. This compound is again washed with saturated Na$_2$CO$_3$ and subsequently dried by passing through Na$_2$SO$_4$. Ethyl acetate is evaporated under reduced pressure. The final compound is purified using column chromatography to obtain a yield of about 68% to about 90%. The purified compound is dried and subsequently characterized using $^1$H NMR.

Boc-Lys(Boc)-N-hexyl-4-Aminomethylquinoline: $^1$H NMR (CDCl$_3$) δ/PPM 8.8 (1H), 8.15 (1H), 7.9 (1H), 7.8-7.5 (2H), 7.1 (1H) 5.2 (1H), 4.9 (1H), 4.7 (1H), 3.5-3 (4H), 1.8-1.2 (32H), 0.9 (3H)

Example 7.3

Synthesis of Lys-N-hexyl-N-(quinolin-4-ylmethyl) hexan-1-amine hydrochlorides (Compound 7c) as Furnished in FIG. 7

Boc-Lys(Boc)-N-hexyl-4-aminomethylquinoline is dissolved in DCM and subsequently CF$_3$COOH (about 50% by volume) is added and stirred at RT. The reactions are monitored by TLC until complete removal of starting material. All the volatile components are removed and the compound is dried overnight in a high vacuum oven.

Then the compound is characterized by $^1$H NMR.

Lys-N-hexyl-4-Aminomethylquinoline: $^1$H NMR (D$_2$O) δ/PPM 8.9 (1H), 8.2 (2H), 8 (1H), 7.8-7.5 (2H), 5.4 (1H), 5.15 (1H) 4.6 (1H), 3.6-3.4 (2H), 3 (2H), 2.1-1.0 (14H), 0.8 (3H)

Example 8.1

Figure 8:
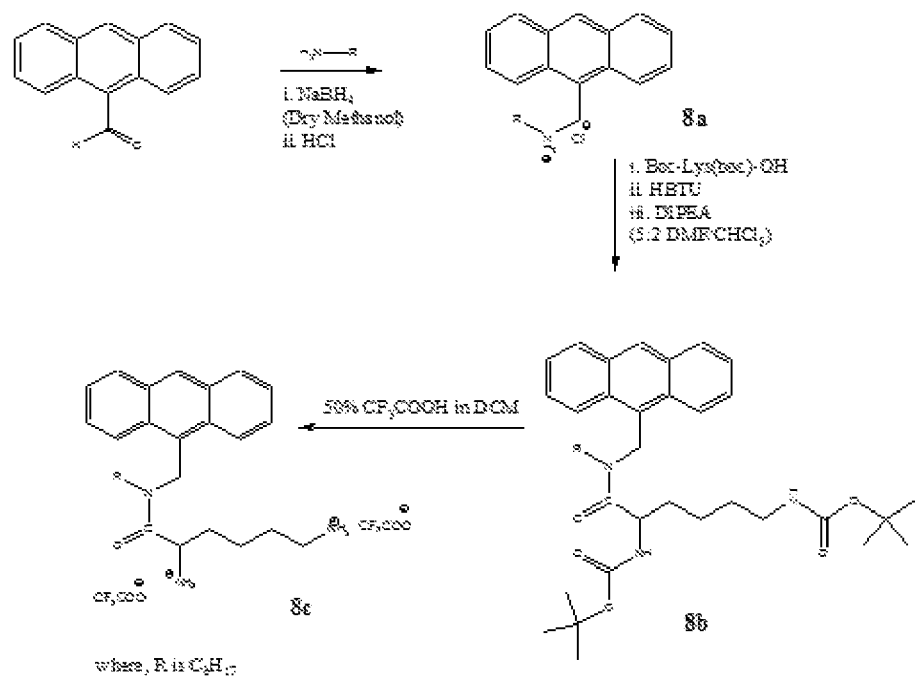
FIG. 8 represents the general synthetic scheme for the preparation of Anthracene derivatives.

Synthesis of N-octyl-9-Aminomethylanthracene hydrochloride (compound 8a) as Furnished in FIG. 8

About 0.5 g, (2.4 mmol) of 9-anthraldehyde and about 2.42 mmol octylamine are dissolved in about 20 ml of 1:1 mixture of dry chloroform and methanol, followed by stirring at room-temperature (under Nitrogen atmosphere) for about 6 hrs. The resulting clear solution is then cooled to a temperature of about 0° C., and about 0.165 g (4.356 mmol) Sodium borohydride is added to the cooled solution. The solution is allowed to attain room temperature and stirred overnight. Then the solvents in the solution are evaporated under reduced pressure (not to dryness) and diluted with about 30 ml of diethyl ether. To this, about 20 ml of 2N NaOH is added and stirred for about 15 minutes. After separation from the NaOH layer, the organic layer is subsequently washed with water (×2), brine and dried over MgSO$_4$. The volatiles are then evaporated under reduced pressure and the residue is dissolved in minimum volume of methanol. To this about 3 ml of 4N HCl is added and instantaneous formation of precipitate is observed. The volatile components are completely removed and the precipitate is dissolved in about 5 ml of ethyl acetate (about 5 drops of methanol is added to dissolve the precipitate completely). To this hexane is added to obtain pure crystals of the target compound (N-octyl-9-Aminomethylanthracene hydrochloride) (Yield: >67%). These crystals are filtered, dried and subsequently characterized using $^1$H NMR.

The characterized profile of N-octyl-9-Aminomethylanthracene hydrochloride is illustrated below:

N-octyl-9-Aminomethylanthracene hydrochloride (8a): $^1$H-NMR (CDCl$_3$) δ/ppm: 9.7 (2H), 8.51 (1H), 8.38 (2H), 8.0 (2H), 7.6 (2H), 7.5 (2H), 5.1 (2H), 2.68 (2H), 1.74 (2H), 1.2-1.0 (10H), 0.79 (3H)

Example 8.2

Synthesis of Boc-Lys(Boc)-N-octyl-9-Aminomethylanthracene (compound 8b) as Furnished in FIG. 8

To a stirred solution containing about 0.46 g (1.34 mmol) of Boc-Lys(Boc)-OH in about 7 ml of 5:2 DMF/CHCl$_3$, about 585 μL (3.36 mmol) of N,N-Diisopropylethylamine (DIPEA) is added at temperature of about 0° C. To this solution about 0.51 g, 1.34 mmol of HBTU is added. This mixture is stirred for about 5 minutes at about 0° C. and subsequently, about 0.4 g, 1.12 mmol N-octyl-9-Aminomethylanthracene hydrochloride is added. The mixture is again stirred at about 0° C. for about 30 minutes and subsequently at room temperature for about 24 hrs. At the end of about 24 hrs, CHCl$_3$ is evaporated under reduced pressure and the resulting solution is diluted to 2 times its original volume by addition of ethyl acetate. This mixture is subsequently washed with 0.5 M KHSO$_4$, H$_2$O (×3) and brine. After passage through anhydrous Na$_2$SO$_4$, the volatile components are evaporated under reduced pressure and the residue is purified using column chromatography (only CHCl$_3$) to obtain Boc-Lys(Boc)-N-octyl-9-Aminomethylanthracene with an yield of about 75%. The purified compound is subsequently characterized using $^1$H NMR, IR and Mass spectrometry.

The characterized profile of Boc-Lys(Boc)-N-octyl-9-Aminomethylanthracene is illustrated below:

Boc-Lys(Boc)-N-octyl-9-Aminomethylanthracene: $^1$H-NMR (CDCl$_3$) δ/ppm: 8.5 (1H), 8.2 (2H), 8 (4H), 6.08 (1H), 5.46 (1H), 5.32 (1H), 4.56 (2H) 3.1-2.7 (4H), 1.69-0.75 (39H). HRMS (m/z): [M+Na]$^+$ obsd.=670.4224 (calc.=670.4196).

Example 8.3

Synthesis of Lys-N-octyl-9-Aminomethylanthracene trifluoroacetate (compound 8c) as Furnished in FIG. 8

About 0.35 mmol of Boc-Lys(Boc)-N-octyl-9-Aminomethylanthracene is dissolved in about 5 ml DCM and subsequently CF3COOH (50% by volume) is added and stirred at room temperature. The reactions are monitored by TLC until complete removal of starting material is observed. All the volatile components are removed by evaporation under pressure, and the product is purified by reverse phase HPLC using 0.1% Trifluoro acetic acid (TFA) in water and acetonitrile (0-100%) as mobile phase, C18 column (10 mm diameter, 250 mm length) as stationary phase and UV detector at 270 nm wavelength is used. After drying the compounds in freeze drier, they are characterized by 1H NMR, IR and mass spectrometry.

The characterized profile of N-octyl-9-Aminomethylanthracene trifluoroacetate is illustrated below:

Lys-N-octyl-9-Aminomethylanthracene trifluoroacetate: $^1$H NMR (DMSO-d$_6$) δ/ppm: 8.7 (1H), 8.5-8.1 (8H), 7.9-7.5 (6H), 6.0 (1H), 5.4 (1H), 4.18 (1H), 3.0-2.7 (1H), 1.73-0.71 (24H). HR-MS (m/z): [M+H]$^+$ obsd.=448.3322 (calc.=448.3328).

While preferred embodiments has been illustrated and described above, it has to be however understood that similar procedure without departing from the spirit and scope of the present disclosure is being employed for the synthesis of other compounds of Formula I (apart from ACK, NCK and BCK series), wherein aldehydes of other aromatic radical or aliphatic radical with appropriate substituents defined in the embodiments are made to react with alkylamine (carbon length varying from C1 to C20, preferably C2 to C14). The aldehyde forms a Schiff's base, which is then reduced by Sodium borohydride to form secondary amines. Salts of these secondary amines are coupled to the free acid group of amino acid [wherein the functional groups of amino acid (apart from carboxylic group) is protected by tertiary butyl carbamate group or Boc] using O-Benzotriazole-N,N,N',N'-tetramethyl-uronium-hexafluorophosphate (HBTU) coupling chemistry. Finally the tertiarybutyl carbamate groups are deprotected using Trifluoroacetic acid to obtain the respective compounds. The compounds obtained are later purified and characterized.

Further, it is to be understood that apart from the synthesis of aforementioned compounds, the salt forms of said compounds can be arrived by following known procedures of the art. Such procedures of salt preparation are within the scope of the present disclosure and do not require any extraordinary technical effort.

Example 9

Antibacterial Activity of Compounds of the Present Disclosure

Antibacterial activity is reported as Minimum Inhibitory Concentration (MIC), i.e. the lowest concentration of the antimicrobial agent that will inhibit the growth of a microorganism after overnight incubation. Water-soluble ACK, NCK and BCK series of compounds are assayed in a modified micro-dilution broth format. Stock solutions are made by serially diluting the compounds using autoclaved Millipore water. Bacteria, to be tested are grown for about 6 hrs in the suitable media containing ~$10^9$ cfu/mL (determined through dilution plate technique by spread plate method), which is then diluted to $10^5$ cfu/mL using nutrient media. 50 μL of serially diluted compound is added to a 96 well plate containing 150 μL bacterial solutions. Two controls are made; one containing 150 μL of media and 50 μL of compound and the other containing 200 μL of bacterial solution. The plate is then incubated at 37° C. for a period of about 24 hrs and MIC data is recorded by measuring the O.D. value at 600 nm using a Tecan InfinitePro series M200 Microplate Reader. MIC value is determined by taking the average of triplicate O.D. values for each concentration and plotting it against concentration using Origin Pro 8.0 software. The data is then subjected to sigmoidal fitting. From the curve, MIC value is determined, as the point in the curve where the O.D. is similar to that of control having no bacteria. The MIC values and errors of independent experiments are reported as average and standard deviation of triplicates.

The antimicrobial activities of the compounds of present disclosure are determined against a variety of bacteria by evaluating their Minimum Inhibition Concentrations (MIC). The compounds are active against both gram-positive and gram negative bacteria at micro molar concentrations comparable to the clinically approved conventional antibiotics.

Results

Activity of Compounds of ACK Series

The compounds of ACK series exhibit antimicrobial activity against drug sensitive bacteria and drug resistant bacteria. The ACK series are active against S. aureus at a concentration below 11 μg/ml, wherein ACK-4, ACK-6, ACK-8 and ACK-10 exhibit most effective MIC value of about 5.3 μg/ml, 2.4 μg/ml, 2.2 μg/ml and 7.1 μg/ml, respectively.

The compounds of ACK series are active against E. faecium at a concentration below 13.6 μg/ml, wherein ACK-4, ACK-6, ACK-8 and ACK-10 exhibit most effective MIC value of about 4.5 μg/ml, 3.3 μg/ml, 2.5 μg/ml and 4.9 μg/ml, respectively.

The compounds of ACK are active against E. coli at a concentration below 26 μg/ml, wherein ACK-4, ACK-6 and ACK-8 exhibit most effective MIC value of about 4.8 μg/ml, 3.5 μg/ml and 2.9 μg/ml, respectively.

The compounds of ACK series are active against P. aeruginosa at a concentration below 11 μg/ml, wherein ACK-2, ACK-4, ACK-6 and ACK-8 exhibit most effective MIC value of about 4 μg/ml, 1.9 μg/ml, 1.6 μg/ml and 3.8 μg/ml, respectively.

The compounds of ACK series are active against methicillin-resistant S. aureus at a concentration below 21 μg/ml, wherein ACK-4, ACK-6, ACK-8 and ACK-10 exhibit most effective MIC value of about 6.3 μg/ml, 2.8 μg/ml, 2.3 μg/ml and 4.6 μg/ml, respectively.

The compounds ACK series are active against vancomycin-resistant E. faecium at a concentration below 7.2 μg/ml, wherein ACK-4, ACK-6, ACK-8 and ACK-10 exhibit most effective MIC value of about 5.3 μg/ml, 5.2 μg/ml, 3 μg/ml and 5.6 μg/ml, respectively.

The ACK series are active against K. pneumonia at a concentration below 31 μg/ml, wherein ACK-4, ACK-6, ACK-8 and ACK-10 exhibit most effective MIC value of about 17 μg/ml, 16 μg/ml, 4.3 μg/ml and 7.6 μg/ml, respectively.

Activity of Compounds of NCK Series

The compounds of NCK series exhibit antimicrobial activity against drug sensitive bacteria and drug resistant bacteria.

The NCK series are active against S. aureus at a concentration below 20 μg/ml, wherein NCK-8, NCK-10 and NCK-12 exhibit most effective MIC value of about 6.3 μg/ml, 2.5 μg/ml and 3 μg/ml, respectively.

The compound of NCK series are active against E. faecium at a concentration below 34 μg/ml, wherein NCK-8, NCK-10 and NCK-12 exhibit most effective MIC value of about 5.5 μg/ml, 3.5 μg/ml and 1.6 μg/ml, respectively.

The compounds of NCK series are active against E. coli at a concentration below 25 μg/ml, wherein NCK-8, NCK-10 and NCK-12 exhibit most effective MIC value of about 5 μg/ml, 4 μg/ml and 3.1 μg/ml, respectively.

The compounds of NCK series are active against P. aeruginosa at a concentration below 11 μg/ml, wherein NCK-6, NCK-8, NCK-10 and NCK-12 exhibit most effective MIC value of about 11 μg/ml, 5.4 μg/ml, 3 μg/ml and 3.2 μg/ml, respectively.

The compounds of NCK series are active against methicillin-resistant S. aureus at a concentration below 65 μg/ml, wherein NCK-8, NCK-10 and NCK-12 exhibit most effective MIC value of about 4.4 μg/ml, 2.6 μg/ml and 2.7 μg/ml, respectively.

The compounds of NCK series are active against vancomycin-resistant E. faecium at a concentration below 54 μg/ml, wherein NCK-8, NCK-10 and NCK-12 exhibit most effective MIC value of about 7 μg/ml, 1.6 μg/ml and 3.4 μg/ml, respectively.

The compounds of NCK series are active against K. pneumonia at a concentration below 100 μg/ml, wherein NCK-8, NCK-10 and NCK-12 exhibit most effective MIC value of about 13 μg/ml, 5.8 μg/ml and 4 μg/ml, respectively.

Activity of Compounds of BCK Series

The compounds of BCK series exhibit antimicrobial activity against drug sensitive bacteria and drug resistant bacteria.

The BCK series are active against S. aureus at a concentration below 46 μg/ml, wherein BCK-10, BCK-12 and BCK-14 exhibit most effective MIC value of about 5.7 μg/ml, 2.7 μg/ml and 3.1 μg/ml, respectively.

The compounds of BCK series are active against E. faecium at a concentration below 60 μg/ml, wherein BCK-10, BCK-12 and BCK-14 exhibit most effective MIC value of about 6.5 μg/ml, 2.6 μg/ml and 2 μg/ml, respectively.

The compounds of BCK series are active against E. coli at a concentration below 51 g/ml, wherein BCK-10, BCK-12 and BCK-14 exhibit most effective MIC value of about 6.5 μg/ml, 5 μg/ml and 3.1 μg/ml, respectively.

The compounds of BCK series are active against P. aeruginosa at a concentration below 60 μg/ml, wherein BCK-10, BCK-12 and BCK-14 exhibit most effective MIC value of about 4 µg/ml, 4 µg/ml and 2.8 µg/ml, respectively.

The compounds of BCK series are active against methicillin-resistant *S. aureus* at a concentration below 100 g/ml, wherein BCK-10, BCK-12 and BCK-14 exhibit most effective MIC value of about 15.7 µg/ml, 2.9 µg/ml and 2.5 µg/ml, respectively.

The compounds of BCK series are active against vancomycin-resistant *E. faecium* at a concentration below 100 µg/ml, wherein BCK-10, BCK-12 and BCK-14 exhibit most effective MIC value of about 5.8 µg/ml, 3.3 µg/ml and 2.5 µg/ml, respectively.

The compounds of BCK series are active against *K. pneumonia* at a concentration below 100 µg/ml, wherein BCK-10, BCK-12 and BCK-14 exhibit most effective MIC value of about 31 µg/ml, 2.8 µg/ml and 4 µg/ml, respectively.

Activity of Compounds of Dec-CK-8

The compound Dec-CK-8 is active against all bacteria at a concentration below 5.6 µg/ml. It shows best activity against MRSA and *E. faecium* at a concentration of 3 µg/ml.

The above said antibacterial activity data is illustrated in table 3, as further described below.

Example 10

Haemolytic Activity

Erythrocytes are isolated from freshly drawn, heparinized human blood and re-suspended to 5 vol % in PBS (pH 7.4). In a 96-well microtiter plate, 150 µl of erythrocyte suspension is added to 50 µl of serially diluted compound. Two controls are made, one without compound and other with 50 µl of 1 vol % solution of Triton X-100. The plate is incubated for about 1 hr at a temperature of about 37° C. The plate is then centrifuged at 3,500 rpm for about 5 min, 100 µl of the supernatant from each well is transferred to a fresh microtiter plate, and absorbance at 540 nm is measured. Percentage of hemolysis is determined as (A−A0)/(Atotal−A0)× 100, where A is the absorbance of the test well, A0 the absorbance of the negative controls (without compound), and A total the absorbance of 100% hemolysis wells (with Triton X-100), when absorbance is read at 540 nm.

Toxicity studies of the compounds are carried out on freshly drawn human RBCs. Toxicity of the antimicrobial compounds of the present disclosure is defined by their $HC_{50}$ values illustrated in Table 3, i.e. the concentration of compound at which 50% of the blood cells are lysed. Haemolytic studies conducted herein illustrates that the antimicrobial compounds provided by the instant disclosure are selective towards drug sensitive bacteria and drug resistant bacteria over human RBCs, thus establishing the non-toxicity of the present compounds.

In an embodiment, $HC_{50}$ values for the compounds in the ACK series ranges from about 64 µg/ml to about 118 µg/ml.

In another embodiment, $HC_{50}$ values for the compounds in the NCK series ranges from about 54 µg/ml to about 508 µg/ml.

In yet another embodiment, $HC_{50}$ values for the compounds in the BCK series ranges from about 45 µg/ml to about 325 µg/ml.

In yet another embodiment, $HC_{50}$ values for Dec-CK-8 is 82 µg/ml.

TABLE 3

In-vitro antibacterial and haemolytic activity of the compounds of present disclosure

| | Minimum Inhibitory Concentration (µg mL$^{-1}$) | | | | | | | $HC_{50}$ |
| --- | --- | --- | --- | --- | --- | --- | --- | --- |
| | Drug sensitive bacteria | | | | Drug resistant bacteria | | | (µg |
| Compounds | S. aureus | E. faecium | E. coli | P. aeruginosa | MRSA | VRE | K. pneumonia | mL$^{-1}$) |
| ACK-2 | 11 | 13.6 | 25 | 4 | 21 | 7.2 | 31 | 118 |
| ACK-4 | 5.3 | 4.5 | 4.8 | 1.9 | 6.3 | 5.3 | 17 | 91 |
| ACK-6 | 2.4 | 3.3 | 3.5 | 1.6 | 2.8 | 5.2 | 16 | 82 |
| ACK-8 | 2.2 | 2.5 | 2.9 | 3.8 | 2.3 | 3 | 4.3 | 64 |
| ACK-10 | 7.1 | 4.9 | 26 | 11 | 4.6 | 5.6 | 7.6 | 71 |
| NCK-4 | >100 | >100 | >100 | >100 | >100 | >100 | >100 | >1000 |
| NCK-6 | 20 | 34 | 25 | 11 | 65 | 54 | 100 | 508 |
| NCK-8 | 6.3 | 5.5 | 5 | 5.4 | 4.4 | 7 | 13 | 60 |
| NCK-10 | 2.5 | 3.5 | 4 | 3 | 2.6 | 1.6 | 5.8 | 54 |
| NCK-12 | 3 | 1.6 | 3.1 | 3.2 | 2.7 | 3.4 | 4 | 56 |
| BCK-4 | >100 | >100 | >100 | >100 | >100 | N.D.[a] | >100 | >1000 |
| BCK-6 | >100 | >100 | >100 | >100 | >100 | N.D. | >100 | >1000 |
| BCK-8 | 46 | 60 | 51 | 60 | >100 | >100 | >100 | 325 |
| BCK-10 | 5.7 | 6.5 | 6.5 | 4 | 15.7 | 5.8 | 31 | 95 |
| BCK-12 | 2.7 | 2.6 | 5 | 4 | 2.9 | 3.3 | 2.8 | 45 |
| BCK-14 | 3.1 | 2 | 3.1 | 2.8 | 2.5 | 2.5 | 4 | 50 |
| Dec-CK-8 | 3.1 | 3 | 3.1 | 4.2 | 3 | 3.3 | 5.6 | 82 |
| 6a | 60 | — | — | — | — | — | — | — |
| 6b | 7.5 | — | — | — | — | — | — | — |
| 6c | 1.3 | — | — | — | — | — | — | — |
| 8c | 2.2 | — | — | — | 3.6 | — | — | 42 |

The present disclosure therefore provides for various compounds (Formula I) and synthesis of the same. Further, from the description above, it is evidently established that the said compounds possess significantly improved antimicrobial properties along with additional advantages such as non-toxicity. The said compounds can be used in various pharmaceutical and non-pharmaceutical applications, particularly as agents for treatment of antimicrobial infections as well as microbial biofilms.

We claim:
1. A compound of formula I:

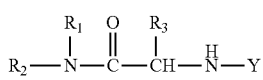

Formula-I wherein,
$R_1$ is

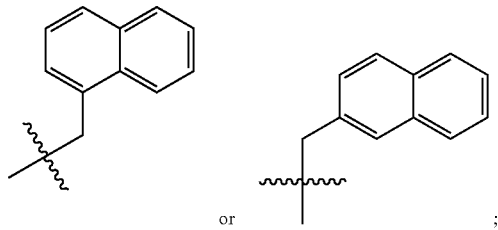 [SMILES: *Cc1cccc2ccccc12 ; *Cc1ccc2ccccc2c1]

$R_2$ is an alkyl chain from $C_1$ to $C_{20}$;
$R_3$ is a side chain of an amino acid; and
Y is selected from a group consisting of hydrogen,

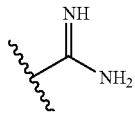 and 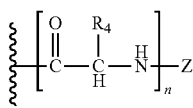

wherein n ranges from 1 to 5,
Z is hydrogen or

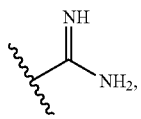

and
$R_4$ is a side chain of an amino acid.
2. The compound as claimed in claim 1, wherein $R_2$ is an alkyl chain from $C_4$ to $C_{20}$.

3. The compound as claimed in claim 1, wherein $R_1$ is

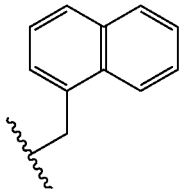 [SMILES: *Cc1cccc2ccccc12]

$R_2$ is

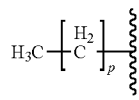

wherein p ranges from 1 to 13;
$R_3$ is the side chain of L-lysine; and
Y is hydrogen.
4. A pharmaceutically accepted salt of the compound of claims 1.
5. A composition comprising:
(a) the compound of claims 1 or the pharmaceutically acceptable salt thereof; and
a pharmaceutically acceptable excipient.
6. The composition of claim 5, wherein the pharmaceutically acceptable excipient is selected from the group consisting of sugar, starch, cellulose, malt, gelatine, talc, cocoa butter, suppository wax, oil, glycol, ester, agar, buffering agent, alginic acid, pyrogen-free water, isotonic saline, Ringer's solution, alcohol, lipid, surfactant, coloring agent, releasing agent, coating agent, sweetening agent, flavouring agent, perfuming agent, preservatives, antioxidants and their derivatives, or any combination thereof.
7. The compound as claimed in claim 1, wherein $R_2$ is an alkyl chain from $C_5$ to $C_{19}$.
8. A method of treating a disease caused by a pathogenic microorganism, comprising administering to a subject in need thereof, a therapeutically effective amount of a compound of claim 1 or a pharmaceutically acceptable salt thereof.
9. The method of claim 8, wherein the pathogenic microorganism is a bacteria.
10. The method of claim 9, wherein the bacteria is a gram positive bacterium or a gram negative bacterium, or a combination thereof.
11. The method of claim 9, wherein the bacteria is a drug sensitive bacterium or a drug resistant bacterium, or a combination thereof.
12. The method of claim 11, wherein the drug sensitive bacterium is selected from a group consisting of *S. aureus, E. faecium, E. coli* and *P. aeruginosa*, or any combination thereof.
13. The method of claim 8, wherein the drug resistant bacterium is selected from a group consisting of vancomycin-resistant *E. faecium*, methicillin-resistant *S. aureus* and β-lactam resistant *K. pneumoniae*, or any combination thereof.

* * * * *

UNITED STATES PATENT AND TRADEMARK OFFICE
CERTIFICATE OF CORRECTION

PATENT NO. : 9,783,490 B2
APPLICATION NO. : 14/652714
DATED : October 10, 2017
INVENTOR(S) : J. Haldar et al.

It is certified that error appears in the above-identified patent and that said Letters Patent is hereby corrected as shown below:

In the Claims

| Column | Line | Error |
|---|---|---|
| 58 (Claim 5, Line 2) | 25 | "claims 1" should read --claim 1-- |
| 58 (Claim 5, Line 4) | 27 | before "a pharmaceutically" insert --(b)-- |

Signed and Sealed this
Tenth Day of July, 2018

Andrei Iancu
*Director of the United States Patent and Trademark Office*